United States Patent
Casuscelli et al.

(10) Patent No.: US 9,145,418 B2
(45) Date of Patent: *Sep. 29, 2015

(54) SUBSTITUTED 3,4-DIHYDROPYRROLO[1,2-A]PYRAZIN-1(2H)-ONES AS PROTEIN KINASE INHIBITORS

(71) Applicant: NERVIANO MEDICAL SCIENCES S.R.L., Nerviano (IT)

(72) Inventors: Francesco Casuscelli, Dairago (IT); Elena Casale, Somma Lombardo (IT); Marisa Montemartini, Nerviano (IT); Claudia Piutti, Nerviano (IT)

(73) Assignee: NERVIANO MEDICAL SCIENCES S.R.L., Nerviano (MI) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/349,516

(22) PCT Filed: Oct. 4, 2012

(86) PCT No.: PCT/EP2012/069586
§ 371 (c)(1),
(2) Date: Apr. 3, 2014

(87) PCT Pub. No.: WO2013/050446
PCT Pub. Date: Apr. 11, 2013

(65) Prior Publication Data
US 2014/0243347 A1 Aug. 28, 2014

(30) Foreign Application Priority Data
Oct. 7, 2011 (EP) .................................. 11184337

(51) Int. Cl.
*A61K 31/4985* (2006.01)
*C07D 487/04* (2006.01)
*A61K 45/06* (2006.01)
*A61N 5/10* (2006.01)

(52) U.S. Cl.
CPC .......... *C07D 487/04* (2013.01); *A61K 31/4985* (2013.01); *A61K 45/06* (2013.01); *A61N 5/10* (2013.01)

(58) Field of Classification Search
CPC .......................... A61K 31/4985; C07D 487/04
USPC .................... 514/249; 544/349, 373; 546/200
See application file for complete search history.

(56) References Cited

FOREIGN PATENT DOCUMENTS

WO  WO 2007/042784 A2  4/2007
WO  WO 2010/031816 A1  3/2010

OTHER PUBLICATIONS

Jordan, V. C. Nature Reviews: Drug Discovery, 2, 2003, 205.*
Hackam, et al. JAMA, 296(14), 2006, 1731-1732.*
Amaravadi R. et al., "The Survival Kinases Akt and Pim as Potential Pharmacological Targets", The Journal of Clinical Investigation 115(10):2618-2624 (Oct. 2005).
Beharry Z. et al., "The Pim Protein Kinases Regulate Energy Metabolism and Cell Growth", PNAS 108(2):528-533 (Jan. 11, 2011).
Blanco-Aparicio C. et al., "Pim 1 Kinase Inhibitor ETP-45299 Suppresses Cellular Proliferation and Synergizes With PI3K Inhibition", Cancer Letters 300(2):145-153 (2010).
Brault L. et al., "PIM Serine/Threonine Kinases in the Pathogenesis and Therapy of Hematologic Malignancies and Solid Cancers", Haematologica 95(6):1004-1015 (2010).
Choudhary C. et al., "Mislocalized Activation of Oncogenic RTKs Switches Downstream Signaling Outcomes", Molecular Cell 36:326-339 (Oct. 23, 2009).
Cohen A.M. et al., "Increased Expression of the hPim-2 Gene in Human Chronic Lymphocytic Leukemia and Non-Hodgkin Lymphoma", Leukemia & Lymphoma 45(5):951-955 (May 2004).
Cohen P., "Protein Kinases—The Major Drug Targets of the Twenty-First Century?", Nature Reviews-Drug Discovery 1:309-315 (Apr. 2002).
Cohen P., "The Development and Therapeutic Potential of Protein Kinase Inhibitors", Current Opinion in Chemical Biology 3:459-465 (1999).
Huttmann A. et al., "Gene Expression Signatures Separate B-Cell Chronic Lymphocytic Leukaemia Prognostic Subgroups Defined by ZAP-70 and CD38 Expression Status", Leukemia 20:1774-1782 (2006).

(Continued)

*Primary Examiner* — Douglas M Willis
(74) *Attorney, Agent, or Firm* — Scully, Scott, Murphy & Presser, P.C.

(57) ABSTRACT

The present invention relates to substituted 3,4-dihydropyrrolo[1,2-a]pyrazin-1(2H)-one derivatives, of formula (I)

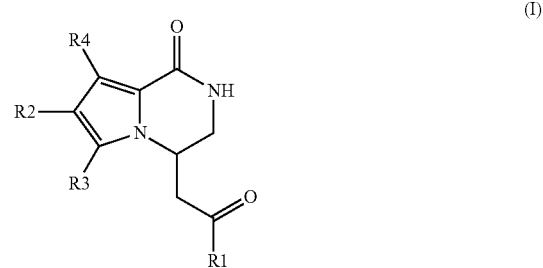

which modulate the activity of protein kinases and are therefore useful in treating diseases caused by dysregulated protein kinase activity. The present invention also provides methods for preparing these compounds, pharmaceutical compositions comprising these compounds, and methods of treating diseases utilizing such compounds or the pharmaceutical compositions containing them.

13 Claims, No Drawings

(56) References Cited

OTHER PUBLICATIONS

Kim K-T et al., "Pim-1 is Up-Regulated by Constitutively Activated FLT3 and Plays a Role in FLT3-Mediated Cell Survival", Blood 105(4):1759-1767 (Feb. 15, 2005).
Kumar A. et al., "Crystal Structures of Proto-Oncogene Kinase Pim1: A Target of Aberrant Somatic Hypermutations in Diffuse Large Cell Lymphoma", J. Mol. Biol. 348:183-193 (2005).
Nihira K. et al., "Pim-1 Controls NF-kB Signalling by Stabilizing RelA/p65", Cell Death and Differentiation 17:689-698 (2010).
Shah N. et al., "Potential Roles for the PIMI1 Kinase in Human Cancer-A Molecular and Therapeutic Appraisal", European Journal of Cancer 44:2144-2151 (2008).
Tamburini J. et al., "Protein Synthesis is Resistant to Rapamycin and Constitutes a Promising Therapeutic Target in Acute Myeloid Leukemia", Blood 114(8):1618-1627 (Aug. 20, 2009).
Velculescu V.E., "Defining the Blueprint of the Cancer Genome", Carcinogenesis 29(6):1087-1091 (2008).
Wang J. et al., "Pim1 Kinase Synergizes With c-MYC to Induce Advanced Prostate Carcinoma", Oncogene 29:2477-2487 (2010).
Weissman S.A. et al., "Ligand-Free Palladium-Catalyzed Cyanation of Aryl Halides", J. Org. Chem. 70:1508-1510 (2005).
Yeung P Y et al., "A Mild and Efficient Palladium-Catalyzed Cyanation of Aryl Chlorides With K4[Fe(CN)6]", Organic Letters 13(4):648-651 (2011).
International Search Report dated Dec. 12, 2012 issued in PCT/EP2012/069586.

\* cited by examiner

SUBSTITUTED 3,4-DIHYDROPYRROLO[1,2-A]PYRAZIN-1(2H)-ONES AS PROTEIN KINASE INHIBITORS

BACKGROUND OF THE DISCLOSURE

The present invention relates to substituted 3,4-dihydropyrrolo[1,2-a]pyrazin-1(2H)-one derivatives, to a process for their preparation, to pharmaceutical compositions comprising them, and to their use as therapeutic agents, particularly in the treatment of diseases caused by dysregulated protein kinase activity, such as cancer, cell proliferative disorders, viral infections, immune disorders, neurodegenerative disorders and cardiovascular diseases. The malfunctioning of protein kinases (PKs) is the hallmark of numerous diseases. A large share of the oncogenes and proto-oncogenes involved in human cancers encode for PKs. The enhanced activities of PKs are also implicated in many non-malignant diseases, such as benign prostate hyperplasia, familial adenomatosis, polyposis, neurofibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or deregulation see, for instance, Current Opinion in Chemical Biology, 1999, 3, 459 465; Nature Rev. Drug Discov. 2002; and Carcinogenesis, 2008, 29, 1087-1091.

Originally identified as activated genes by proviral mutagenesis in a lymphoma mouse model, PIMs (PIM1, PIM2 and/or PIM3 throughout this application) are protein-serine/threonine kinases. PIM kinases are poorly expressed in normal tissues, and overexpressed or even mutated in a discrete number of human cancers, including Lymphoma, Leukaemia, Prostate, Pancreas and Gastric cancers [Shah et al. Eur. J. Cancer, 44, 2144-51, (2008)].

PIM kinases are constitutively active and their activity supports in vitro and in vivo tumor cell growth and survival through modification of an increasing number of common as well as isoform-specific substrates including several cell cycle regulators and apoptosis mediators. PIM1, but not PIM2, seems also to mediate homing and migration of normal and malignant hematopoietic cells by regulating chemokine receptor surface expression [Brault et al. Haematologica, 95, 1004-1015 (2010)].

There is increasing evidence that PIM1 and PIM2 kinases may be involved in mediating the oncogenic effects of some acute myelogenous leukemias (AML)-associated oncogenes, in particular, the oncogenic role of FLT3-mutations (ITD and KD mut., present in 30% of AMLs) and/or translocations involving the MLL gene (occurring in 20% of AMLs)), [Kumar, et al. J. Mol. Biol. 348, 183-193, (2005)]. PIM1 is more expressed in FLT3-ITD-transformed AML cells than in WT bone marrow cells. Data suggest that PIM1 as well as PIM2 inhibition may mediate FLT3-ITD-dependent death of AML cells. Interestingly, cells transformed by FLT3 mutations that confer resistance to small-molecule tyrosine kinase inhibitors were still sensitive to knockdown of PIM2, or PIM1 and PIM2, by RNAi, [Kim et al., Blood, 105, 1759-67, (2005)].

Moreover, PIM2 has been reported being over-expressed and associated with progression of several malignancies that originate from the B-cell lineage such as chronic lymphocytic (CLL), diffuse large B-cell lymphoma (DLBCL), mantle cell lymphoma (MCL) or myeloma [Cohen et al., Leukemia & Lymphoma 45(5) 951-955 (2004), Huttmann et al. Leukemia 20 1774 (2006)].

In recent studies, it was demonstrated that both NE-κB and Pim kinases are implicated in tumorigenesis, in particular, PIM1 phosphorylation of RelA/p65 at Ser276 is believed to allow defense against ubiquitin-mediated degradation and whereby exerted activation of NF-κB signalling, [Nihira K. et al. Cell Death & Differentiation 2010, 17, 689-698].

In prostate cancers, oncogenic PIM1 kinase is implicated with c-Myc in carcinogenesis, and the c-MYC/Pim1 synergy is critically dependent on PIM1 kinase activity. PIM1 cooperativity with c-MYC in vivo, is explained not only on the c MYC activity by S62 phosphorylation, but also on the evidence of neuroendocrine (NE) differentiation [Wang J. et al. Oncogene (2010) 29, 2477-2487].

Interestingly, PIM and AKT/PKB seem to play partly redundant roles in mediating growth and survival of hematopoietic cells, most probably due to overlapping substrates like BAD, p21WAF1/CIP1, p27KIP1, or Cot/Tpl-2 [Choudhary et al., Mol Cell. 36, 326-39 (2009)].

PIM kinases have been shown to control mTOR inhibition (rapamycin) resistanceresistant, proliferation and survival. Therefore, a combination of small molecule inhibitors targeting several survival kinases might be essential for a powerful cancer therapeutic platform [Amaravadi R., et al. J. Clin. Invest. 2005, 115 (10), 2618-24]. Oncogenic protein synthesis through eIF4E binding protein 1 (4E-BP1) seems to be mTOR-indipendent and controlled by PIM2. This observations suggest that the oncogenic eIF4F translation-initiating complex could be blocked with small molecules PIM2 inhibitors [Tamburini J. et al. Blood 2009, 114 (8), 1618-27 and; Brault L. et al. Haematologica 2010, 95 (6), 1004-1015 and Beharry Z. PNAS 2011, 108, 528-533].

Recently, two differents research groups have reported the successful combination of PIM and PI3K inhibitors. Blanco-Aparicio, C. et al. [Cancer Lett. 2011, 300(2):145-53] combined the PI3K inhibitor GDC-0941 with a PIM1 inhibitor and found a strongly synergistic effect in AML cells. Ebens et al. during the 52$^{nd}$ ASH annual meeting, reported that a pan-PIM inhibition suppressed growth in myeloma cell lines, xenografts, and primary patient samples, both as a single-agent as well acting synergistically in combination with GDC-0941.

3,4-Dihydro-2h-pyrrolo[1,2-a]pyrazin-1-one derivatives possessing kinase inhibitory activity have been disclosed in WO2010/031816, in the name of the Applicant itself.

Despite these developments, there is still need for effective agents for said diseases.

BRIEF SUMMARY OF THE DISCLOSURE

A new class of substituted 3,4-dihydropyrrolo[1,2-a]pyrazin-1(2H)-one compounds has now been identified endowed with an activity both on PIM1 and PIM2, higher than previously achieved in the prior art. These compounds were found able to prevent the proliferation of human tumour cells at a remarkably low concentration, thereby maximizing the antitumour efficacy while simultaneously reducing risk of the side effects linked to the administration of higher amounts of drugs.

The new compounds have the structure shown in formula (I)

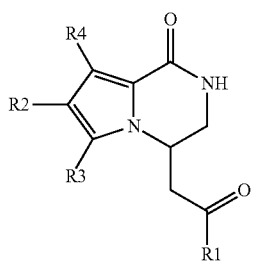

wherein
R1 is NR5R6
wherein R5 and R6 are each independently hydrogen, an optionally substituted group selected from straight or branched $C_1$-$C_6$ alkyl, $C_2$-$C_6$ alkenyl, $C_2$-$C_6$ alkynyl, $C_3$-$C_7$ cycloalkyl, cycloalkyl-alkyl, aryl, arylalkyl, heterocyclyl and heterocyclylalkyl; or R5 and R6 together with the nitrogen atom to which they are bound, form a 5 to 7 membered heterocyclyl group optionally containing one additional heteroatom selected from N, O and S;

R2 is aryl, arylalkyl, heterocyclyl or heterocyclylalkyl;

R3 and R4 are each independently hydrogen, halogen, cyano, or an optionally substituted group selected from straight or branched $C_1$-$C_6$ alkyl, $C_2$-$C_6$ alkenyl, $C_2$-$C_6$ alkynyl, $C_3$-$C_7$ cycloalkyl, cycloalkyl-alkyl, aryl, arylalkyl, heterocyclyl and heterocyclylalkyl;

and a pharmaceutically acceptable salt thereof, provided that when R3 and R4 are hydrogen, R5 is a group of formula

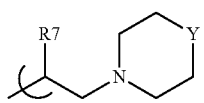

wherein R7 is an optionally substituted group selected from straight or branched $C_1$-$C_6$ alkyl, $C_3$-$C_7$ cycloalkyl, and cycloalkyl-alkyl; and Y is N—R' or CH—NR'R'', wherein R' and R'' are each independently, hydrogen or an optionally substituted group selected from straight or branched $C_1$-$C_6$ alkyl, $C_3$-$C_7$ cycloalkyl, cycloalkylalkyl, heterocyclyl and heterocyclylalkyl.

The present invention also provides methods of synthesizing the substituted derivatives, represented by the formula (I), prepared through a process consisting of standard synthetic transformations and isomers, tautomers, hydrates, solvates, complexes, metabolites, prodrugs, carriers, N-oxides and pharmaceutically acceptable salts.

The present invention also provides a method for treating diseases caused by and/or associated with dysregulated protein kinase activity, particularly ABL, ACK1, AKT1, ALK, AUR1, AUR2, BRK, BUB1, CDC7/DBF4, CDK2/CYCA, CHK1, CK2, EEF2K, EGFR1, EphA2, EphB4, ERK2, FAK, FGFR1, FLT3, GSK3beta, Haspin, IGFR1, IKK2, IR, JAK1, JAK2, JAK3, KIT, LCK, LYN, MAPKAPK2, MELK, MET, MNK2, MPS1, MST4, NEK6, NIM1, P38alpha, PAK4, PDGFR, PDK1, PERK, PIM1, PIM2, PIM3, PKAalpha, PKCbeta, PLK1, RET, ROS1, SULU1, Syk, TLK2, TRKA, TRKb TYK, VEGFR2, VEGFR3, ZAP70; more particularly PIM1, PIM2, PIM3 which comprises administering to a mammal in need thereof an effective amount of a compound of formula (I) as defined above.

A preferred method of the present invention is to treat a disease caused by and/or associated with dysregulated protein kinase activity selected from the group consisting of cancer, cell proliferative disorders, viral infections, immune cell-associated diseases and disorders, neurodegenerative disorders and cardiovascular diseases.

Another preferred method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer, Kaposi's sarcoma and mesothelioma, highly aneuploid tumors and tumors which do overexpress mitotic checkpoint.

Another preferred method of the present invention is to treat specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

Another preferred method of the present invention is to treat immune cell-associated diseases and disorders, such as inflammatory and autoimmune diseases, for examples multiple sclerosis, systemic lupus erythematosis, inflammatory bowel diseases (IBD), Crohn's disease, irritable bowel syndrome, pancreatitis, ulcerative colitis, diverticulosis, myasthenia gravis, vasculitis, psoriasis, scleroderma, asthma, allergy, systemic sclerosis, vitiligo, arthritis such as osteoarthritis, juvenile rheumatoid arthritis, ankylosing spondylitis.

Another preferred method of the present invention is to treat viral infections, in particular the prevention of AIDS development in HIV-infected individuals.

The methods defined above may further comprise subjecting the mammal in need thereof to a radiation therapy or chemotherapeutic regimen in combination with at least one cytostatic or cytotoxic agent.

In addition, the method of the present invention also provides tumor angiogenesis and metastasis inhibition as well as the treatment of organ transplant rejection and host versus graft disease.

The present invention further provides an in vitro method for inhibiting PIM-1, PIM-2, PIM-3 protein kinase activity which comprises contacting the said protein with an effective amount of a compound of formula (I) as defined above.

The present invention also provides a pharmaceutical composition comprising a therapeutically effective amount of a compound of formula (I) or a pharmaceutically acceptable salt thereof, as defined above, and at least one pharmaceutically acceptable excipient, carrier and/or diluent.

In addition to a compound of formula (I), the pharmaceutical composition of the present invention may further comprise one or more chemotherapeutic—e.g. cytostatic or cytotoxic—agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), famesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

In another aspect the invention provides a compound of formula (I) or a pharmaceutically acceptable salt thereof, as defined above, for use as a medicament.

Moreover the invention provides a compound of formula (I) or a pharmaceutically acceptable salt thereof, as defined above, for use in a method of treating cancer.

Finally, the invention provides the use of a compound of formula (I) or a pharmaceutically acceptable salt thereof, as defined above, in the manufacture of a medicament with anticancer activity.

DETAILED DESCRIPTION OF THE DISCLOSURE

Unless otherwise specified, when referring to the compounds of the formula (I) per se as well as to any pharmaceutical composition thereof or to any therapeutic treatment comprising them, the present invention includes all of the hydrates, solvates, complexes, metabolites, prodrugs, carriers, N-oxides and pharmaceutically acceptable salts of the compounds of this invention.

In other words, if easily obtainable from the compounds of the formula (I) as defined above, also their isomers, tautomers, hydrates, solvates, complexes, metabolites, prodrugs, carriers and N-oxides are object of the present invention.

A metabolite of a compound of the formula (I) is any compound into which this same compound of the formula (I) is converted in vivo, for instance upon administration to a mammal in need thereof. Typically, without however representing a limiting example, upon administration of a compound of the formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of the formula (I).

Prodrugs are any covalently bonded compounds, which release in vivo the active parent drug according to the formula (I).

N-oxides are compounds of the formula (I) wherein nitrogen and oxygen are tethered through a dative bond. If a stereogenic center or another form of an isomeric center is present in a compound of the present invention, all forms of such isomer or isomers, including enantiomers and diastereomers, are intended to be covered herein. Compounds containing a stereogenic center may be used as a racemic mixture, an enantiomerically enriched mixture, or the racemic mixture may be separated using well-known techniques and an individual enantiomer may be used alone. In cases in which compounds may have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form. The term aryl includes carbocyclic or heterocyclic hydrocarbons with from 1 to 2 ring moieties, either fused or linked to each other by single bonds, wherein at least one of the rings is aromatic; if present, any aromatic heterocyclic hydrocarbon also referred to as heteroaryl group, comprises a 5 to 6 membered-ring with from 1 to 3 heteroatoms selected from N, O and S.

Examples of aryl groups according to the invention are, for instance, phenyl, biphenyl, α- or β-naphthyl, dihydronaphthyl, thienyl, benzothienyl, furyl, benzofuranyl, pyrrolyl, imidazolyl, pyrazolyl, thiazolyl, isothiazolyl, oxazolyl, isoxazolyl, pyridyl, pyrazinyl, pyrimidinyl, pyridazinyl, indolyl, isoindolyl, purinyl, quinolyl, isoquinolyl, dihydroquinolinyl, quinoxalinyl, benzodioxolyl, indanyl, indenyl, triazolyl, and the like.

With the term "heterocyclyl" (also known as "heterocycloalkyl") we intend a 3- to 7-membered, saturated or partially unsaturated carbocyclic ring where one or more carbon atoms are replaced by heteroatoms such as nitrogen, oxygen and sulfur. Not limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

With the term "$C_3$-$C_7$ cycloalkyl", we intend, unless otherwise provided, 3- to 7-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene, cyclohexadiene, cycloeptane, cycloeptene, cycloeptadiene.

With the term "straight or branched $C_1$-$C_6$ alkyl", hence comprehensive of $C_1$-$C_4$ alkyl, we intend any of the groups such as, for instance, methyl, ethyl, n-propyl, isopropyl, n-butyl, isobutyl, tert-butyl, sec-butyl, n-pentyl, n-hexyl, and the like.

With the term "straight or branched $C_2$-$C_6$ alkenyl" we intend any of the groups such as, for instance, vinyl, allyl, 1-propenyl, isopropenyl, 1-butenyl, 2-butenyl, 3-butenyl, 2-pentenyl, 1-hexenyl, and the like.

With the term "straight or branched $C_2$-$C_6$ alkynyl" we intend any of the groups such as, for instance, ethynyl, 2-propynyl, 4-pentynyl, and the like.

According to the present invention and unless otherwise provided, any of the above R1, R2, R3, R4, R5, R6, R7, R8, R' and R" group may be optionally substituted, in any of their free positions, by one or more groups, for instance 1 to 6 groups, independently selected from: halogen atom, nitro, oxo groups (═O), cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocydylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate.

In their turn, whenever appropriate, each of the above substituent may be further substituted by one or more of the aforementioned groups.

In this respect, with the term halogen atom we intend a fluorine, chlorine, bromine or iodine atom.

With the term cyano we intend a —CN residue.

With the term nitro we intend a —NO$_2$ group.

With the term alkenyl or alkynyl we intend any of the aforementioned straight or branched C$_2$-C$_6$ alkyl groups further bearing a double or triple bond. Non limiting examples of alkenyl or alkynyl groups of the invention are, for instance, vinyl, allyl, 1-propenyl, isopropenyl, 1-butenyl, 2-butenyl, 3-butenyl, 2-pentenyl, 1-hexenyl, ethynyl, 2-propynyl, 4-pentynyl, and the like.

With the term polyfluorinated alkyl or alkoxy we intend any of the above straight or branched C$_1$-C$_6$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term alkoxy, aryloxy, heterocyclyloxy and derivatives thereof we intend any of the above C$_1$-C$_6$ alkyl, aryl or heterocyclyl groups linked to the rest of the molecule through an oxygen atom (—O—).

From all of the above, it is clear to the skilled person that any group which name is a composite name such as, for instance, arylamino has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocydylcarbonylamino, cycloalkyloxycarbonyl and the like, include groups wherein the alkyl, alkoxy, aryl, C$_3$-C$_7$ cycloalkyl and heterocyclyl moieties are as above defined.

Pharmaceutically acceptable salts of the compounds of the formula (I) include the acid addition salts with inorganic or organic acids, e.g., nitric, hydrochloric, hydrobromic, sulfuric, perchloric, phosphoric, acetic, trifluoroacetic, propionic, glycolic, fumaric, lactic, oxalic, malonic, malic, maleic, tartaric, citric, benzoic, cinnamic, mandelic, methanesulphonic, isethionic and salicylic acid. Preferably, the acid addition salt of the compounds of the invention is selected between the hydrochloride or mesylate salt.

Pharmaceutically acceptable salts of the compounds of the formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines, preferably methylamine, ethylamine, diethylamine, triethylamine, piperidine and the like.

Preferred compounds of the formula (I) are the compounds wherein:

R1 is NR5R6 wherein R5 and R6 are each independently hydrogen or an optionally substituted group selected from straight or branched C$_1$-C$_6$ alkyl, C$_3$-C$_7$ cycloalkyl, cycloalkyl-alkyl, aryl, arylalkyl, heterocyclyl and heterocyclylalkyl, or, together with the nitrogen atom to which they are bound, R5 and R6 may form a 5 to 7 membered heterocyclyl group optionally containing one additional heteroatom selected from N, O and S; and R2 R3 and R4 are as defined above.

Another preferred class of compounds of formula (I) are the compounds wherein:

R1 is NR5R6 wherein R5 and R6 are each independently hydrogen or an optionally substituted group selected from straight or branched C$_1$-C$_6$ alkyl, C$_3$-C$_7$ cycloalkyl, cycloalkyl-alkyl, arylalkyl, heterocyclyl and heterocyclylalkyl, or, together with the nitrogen atom to which they are bound, R5 and R6 may form a 5 to 7 membered heterocyclyl group optionally containing one additional heteroatom selected from N, O and S; and R2 R3 and R4 are as defined above.

Another preferred class of compounds of formula (I) are the compounds wherein:

R3 and R4 are each independently hydrogen, halogen, cyano, or an optionally substituted group selected from straight or branched C$_1$-C$_6$ alkyl, C$_2$-C$_6$ alkynyl, C$_3$-C$_7$ cycloalkyl, arylalkyl, heterocyclyl and heterocyclylalkyl; and R1 and R2 are as defined above.

Preferred specific compounds of the formula (I) or a salt thereof are the compounds listed below:

1. 2-[(4R)-7-(3-chlorophenyl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide,
2. 2-[(4S)-7-(3-chlorophenyl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide,
3. N-[(1S)-1-cyclohexyl-2-(4-methylpiperazin-1-yl)ethyl]-2-[(4R)-7-(3-fluorophenyl)-1-oxo-1,2,3,4-tetrahydropyrrolo[1,2-a]pyrazin-4-yl]acetamide,
4. N-[(1S)-1-cyclohexyl-2-(4-methylpiperazin-1-yl)ethyl]-2-[(4S)-7-(3-fluorophenyl)-1-oxo-1,2,3,4-tetrahydropyrrolo[1,2-a]pyrazin-4-yl]acetamide,
5. N-{(1S)-1-cyclohexyl-2-[4-(dimethylamino)piperidin-1-yl]ethyl}-2-[(4R)-7-(3,4-difluorophenyl)-1-oxo-1,2,3,4-tetrahydropyrrolo[1,2-a]pyrazin-4-yl]acetamide,
6. N-{(1S)-1-cyclohexyl-2-[4-(dimethylamino)piperidin-1-yl]ethyl}-2-[(4S)-7-(3,4-difluorophenyl)-1-oxo-1,2,3,4-tetrahydropyrrolo[1,2-a]pyrazin-4-yl]acetamide,
7. N-[(1S)-1-cyclohexyl-2-(4-methylpiperazin-1-yl)ethyl]-2-[(4R)-7-(3,4-difluorophenyl)-1-oxo-1,2,3,4-tetrahydropyrrolo[1,2-a]pyrazin-4-yl]acetamide,
8. N-[(1S)-1-cyclohexyl-2-(4-methylpiperazin-1-yl)ethyl]-2-[(4S)-7-(3,4-difluorophenyl)-1-oxo-1,2,3,4-tetrahydropyrrolo[1,2-a]pyrazin-4-yl]acetamide,
9. N-{(1S)-1-cyclohexyl-2-[4-(dimethylamino)piperidin-1-yl]ethyl}-2-[(4R)-7-(2-fluoropyridin-4-yl)-1-oxo-1,2,3,4-tetrahydropyrrolo[1,2-a]pyrazin-4-yl]acetamide,
10. N-{(1S)-1-cyclohexyl-2-[4-(dimethylamino)piperidin-1-yl]ethyl}-2-[(4S)-7-(2-fluoropyridin-4-yl)-1-oxo-1,2,3,4-tetrahydropyrrolo[1,2-a]pyrazin-4-yl]acetamide,
11. N-[(1S)-1-cyclohexyl-2-(4-methylpiperazin-1-yl)ethyl]-2-[(4R)-7-(2-fluoropyridin-4-yl)-1-oxo-1,2,3,4-tetrahydropyrrolo[1,2-a]pyrazin-4-yl]acetamide,
12. N-[(1S)-1-cyclohexyl-2-(4-methylpiperazin-1-yl)ethyl]-2-[(4S)-7-(2-fluoropyridin-4-yl)-1-oxo-1,2,3,4-tetrahydropyrrolo[1,2-a]pyrazin-4-yl]acetamide,
13. N-[(1S)-1-cyclohexyl-2-(4-methylpiperazin-1-yl)ethyl]-2-[(4R)-7-(3-hydroxyphenyl)-1-oxo-1,2,3,4-tetrahydropyrrolo[1,2-a]pyrazin-4-yl]acetamide,
14. N-{(1S)-1-cyclohexyl-2-[4-(dimethylamino)piperidin-1-yl]ethyl}-2-[7-(3-hydroxyphenyl)-1-oxo-1,2,3,4-tetrahydropyrrolo[1,2-a]pyrazin-4-yl]acetamide,
15. N-{(1S)-1-cyclohexyl-2-[4-(dimethylamino)piperidin-1-yl]ethyl}-2-{(4R)-1-oxo-7-[3-(trifluoromethyl)phenyl]-1,2,3,4-tetrahydropyrrolo[1,2-a]pyrazin-4-yl}acetamide,
16. N-{(1S)-1-cyclohexyl-2-[4-(dimethylamino)piperidin-1-yl]ethyl}-2-{(4S)-1-oxo-7-[3-(trifluoromethyl)phenyl]-1,2,3,4-tetrahydropyrrolo[1,2-a]pyrazin-4-yl}acetamide,
17. N-[(1S)-1-cyclohexyl-2-(4-methylpiperazin-1-yl)ethyl]-2-{(4R)-1-oxo-7-[3-(trifluoromethyl)phenyl]-1,2,3,4-tetrahydropyrrolo[1,2-a]pyrazin-4-yl}acetamide, 18. N-[(1S)-1-cyclohexyl-2-(4-methylpiperazin-1-yl)ethyl]-2-{(4S)-1-oxo-7-[3-(trifluoromethyl)phenyl]-1,2,3,4-tetrahydropyrrolo[1,2-a]pyrazin-4-yl}acetamide,
19. N-[(1S)-1-cyclohexyl-2-(4-methylpiperazin-1-yl)ethyl]-2-[(4S)-1-oxo-7-(1H-pyrazol-4-yl)-1,2,3,4-tetrahydropyrrolo[1,2-a]pyrazin-4-yl]acetamide,
20. 2-[(4R)-7-(3-chlorophenyl)-1-oxo-1,2,3,4-tetrahydropyrrolo[1,2-a]pyrazin-4-yl]-N-[(2S)-3,3-dimethyl-1-(4-methylpiperazin-1-yl)butan-2-yl]acetamide,
21. 2-[(4S)-7-(3-chlorophenyl)-1-oxo-1,2,3,4-tetrahydropyrrolo[1,2-a]pyrazin-4-yl]-N-[(2S)-3,3-dimethyl-1-(4-methylpiperazin-1-yl)butan-2-yl]acetamide,
22. 2-[(4R)-7-(3-chlorophenyl)-1-oxo-1,2,3,4-tetrahydropyrrolo[1,2-a]pyrazin-4-yl]-N-{(1S)-1-cyclohexyl-2-[4-(dimethylamino)piperidin-1-yl]ethyl}acetamide,
23. 2-[(4S)-7-(3-chlorophenyl)-1-oxo-1,2,3,4-tetrahydropyrrolo[1,2-a]pyrazin-4-yl]-N-{(1S)-1-cyclohexyl-2-[4-(dimethylamino)piperidin-1-yl]ethyl}acetamide,
24. 2-[(4R)-7-(3-chlorophenyl)-1-oxo-1,2,3,4-tetrahydropyrrolo[1,2-a]pyrazin-4-yl]-N-[(2S)-1-(4-methylpiperazin-1-yl)propan-2-yl]acetamide,
25. 2-[(4S)-7-(3-chlorophenyl)-1-oxo-1,2,3,4-tetrahydropyrrolo[1,2-a]pyrazin-4-yl]-N-[(2S)-1-(4-methylpiperazin-1-yl)propan-2-yl]acetamide,
26. 2-[(4S)-7-(5-chloro-2-fluorophenyl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide,
27. 2-[(4R)-7-(5-chloro-2-fluorophenyl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide,
28. 2-[(4R)-7-(3-chloro-4-hydroxyphenyl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide,
29. 2-[(4S)-7-(3-chloro-4-hydroxyphenyl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide,
30. 2-[(4S)-6-bromo-7-(3-chloro-4-hydroxyphenyl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide,
31. 2-[(4R)-7-(2-aminopyrimidin-4-yl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide,
32. 2-[(4S)-7-(2-aminopyrimidin-4-yl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide,
33. 2-[(4R)-7-(3-chlorophenyl)-6-iodo-1-oxo-1,2,3,4-tetrahydropyrrolo[1,2-a]pyrazin-4-yl]-N-[(2S)-1-(4-methylpiperazin-1-yl)propan-2-yl]acetamide,
34. 2-[(4S)-7-(3-chlorophenyl)-6-iodo-1-oxo-1,2,3,4-tetrahydropyrrolo[1,2-a]pyrazin-4-yl]-N-[(2S)-1-(4-methylpiperazin-1-yl)propan-2-yl]acetamide,
35. 2-[(4R)-7-(3-fluorophenyl)-6-iodo-1-oxo-1,2,3,4-tetrahydropyrrolo[1,2-a]pyrazin-4-yl]-N-[(2S)-1-(4-methylpiperazin-1-yl)propan-2-yl]acetamide,
36. 2-[(4S)-7-(3-fluorophenyl)-6-iodo-1-oxo-1,2,3,4-tetrahydropyrrolo[1,2-a]pyrazin-4-yl]-N-[(2S)-1-(4-methylpiperazin-1-yl)propan-2-yl]acetamide,
37. 2-[(4R)-6-bromo-7-(3-fluorophenyl)-1-oxo-1,2,3,4-tetrahydropyrrolo[1,2-a]pyrazin-4-yl]-N-[(2S)-1-(4-methylpiperazin-1-yl)propan-2-yl]acetamide,
38. 2-[(4S)-6-bromo-7-(3-fluorophenyl)-1-oxo-1,2,3,4-tetrahydropyrrolo[1,2-a]pyrazin-4-yl]-N-[(2S)-1-(4-methylpiperazin-1-yl)propan-2-yl]acetamide,
39. 2-[(4R)-6-bromo-7-(3-fluorophenyl)-1-oxo-1,2,3,4-tetrahydropyrrolo[1,2-a]pyrazin-4-yl]-N-[(2S)-1-hydroxypropan-2-yl]acetamide,
40. 2-[(4S)-7-(3-fluorophenyl)-1-oxo-1,2,3,4-tetrahydropyrrolo[1,2-a]pyrazin-4-yl]-N-[(2R)-1-hydroxypropan-2-yl]acetamide,
41. 2-[6-bromo-7-(3-fluorophenyl)-1-oxo-1,2,3,4-tetrahydropyrrolo[1,2-a]pyrazin-4-yl]acetamide,
42. 2-[(4R)-7-(3-chlorophenyl)-1-oxo-6-phenyl-1,2,3,4-tetrahydropyrrolo[1,2-a]pyrazin-4-yl]-N-[(2S)-1-(4-methylpiperazin-1-yl)propan-2-yl]acetamide,
43. 2-[(4S)-7-(3-chlorophenyl)-1-oxo-6-phenyl-1,2,3,4-tetrahydropyrrolo[1,2-a]pyrazin-4-yl]-N-[(2S)-1-(4-methylpiperazin-1-yl)propan-2-yl]acetamide and
44. 2-[(4S)-7-(3-chlorophenyl)-1-oxo-6-phenyl-1,2,3,4-tetrahydropyrrolo[1,2-a]pyrazin-4-yl]-N-[(3R)-piperidin-3-yl]acetamide.

For a reference to any specific compound of the formula (I) of the invention, optionally in the form of a pharmaceutically acceptable salt, see the experimental section and claims.

The present invention also provides a process for the preparation of a compound of formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by modifications apparent to those skilled in the art, for instance by appropriately protecting interfering groups, by changing to other suitable reagents known in the art, or by making routine modifications of reaction conditions. Alternatively, other reactions referred to herein or known in the art will be recognized as having adaptability for preparing other compounds of the invention.

The reported Scheme 1 shows the preparation of an intermediate compound of formula (IV).

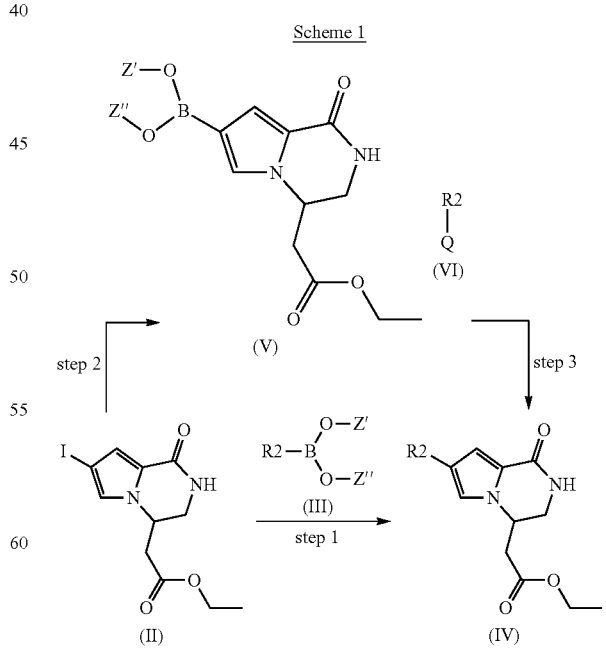

Scheme 1

In the above Scheme 1, R2 is aryl, arylalkyl, heterocyclyl or heterocyclylalkyl; Z' and Z" are either hydrogen, alkyl or, taken together with the oxygen atoms to which they are bonded, may form an optionally substituted 5 to 6 membered heterocycle; Q is a halogen, a triflate, an alkylsulfonyloxy or an arylsulfonyloxy group, such as a mesylate or a tosylate.

Accordingly, a process of the present invention comprises the following steps:

Step 1) mixing the compound of formula (II)

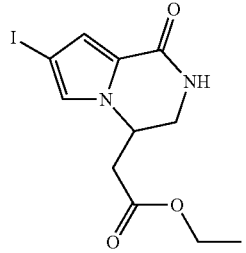

(II)

with an organoboron compound of formula (III):

R2B(OZ')(OZ")      (III)

wherein R2 is aryl, arylalkyl, heterocyclyl or heterocyclylalkyl, and Z' and Z" are either hydrogen, alkyl or, taken together with the oxygen atoms to which they are bonded, may form an optionally substituted 5 to 6 membered heterocycle, to give a compound of formula (IV);

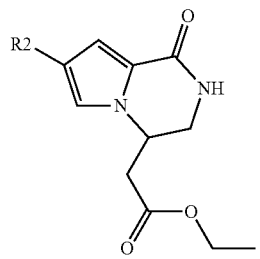

(IV)

wherein R2 is as defined above;
alternatively,
Step 2) reacting the compound of formula (II) with a boronyl reagent;
Step 3) mixing the resultant compound of formula (V)

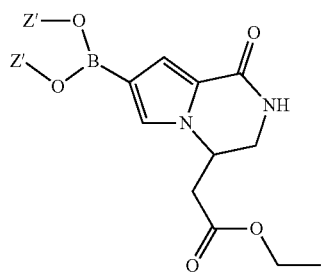

(V)

wherein Z' and Z" are as defined above, with a compound of formula R2-Q (VI) wherein R2 is as defined above and Q is a halogen, a triflate, an alkylsulfonyloxy or an arylsulfonyloxy group, such as a mesylate or a tosylate, to give a compound of formula (IV) as defined above.

The reported Scheme 2 shows the preparation of an intermediate compound of formula (XIV).

Scheme 2

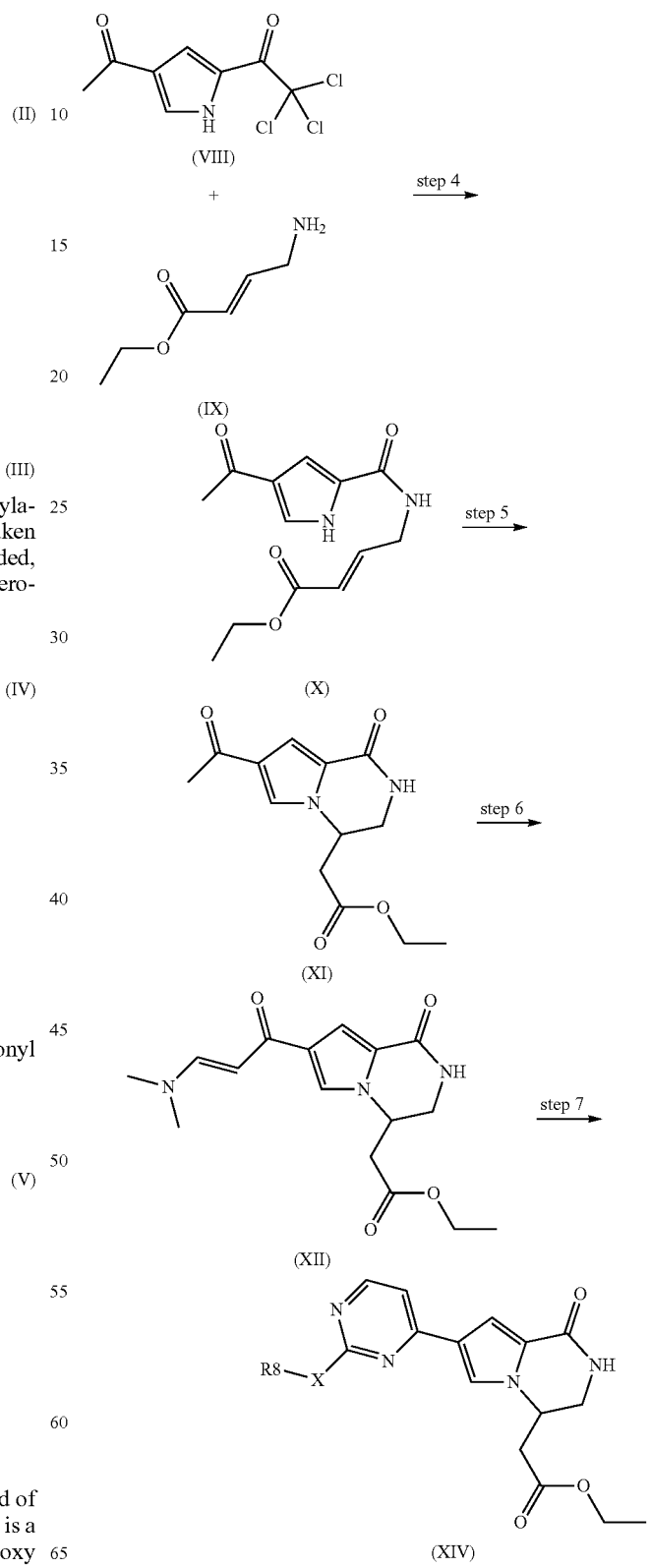

In the above Scheme 2, X is a single bond or a divalent radical selected from —NR', —O— and S, wherein R' is hydrogen or an optionally substituted group selected from straight or branched $C_1$-$C_6$ alkyl, $C_3$-$C_7$ cycloalkyl, cycloalkylalkyl, heterocyclyl and heterocycylalkyl; R8 is hydrogen or an optionally substituted group selected from amino, straight or branched $C_1$-$C_5$ alkyl, $C_3$-$C_7$ cycloalkyl, cycloalkyl-alkyl, aryl, arylalkyl, heterocyclyl and heterocyclylalkyl.

Accordingly, a process of the present invention comprises the following steps:

Step 4) reacting the compound of formula (VIII):

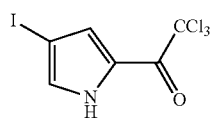
(VIII)

with an ammonium salt of formula (IX):

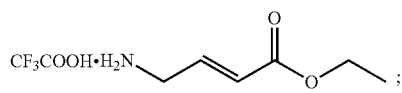
(IX)

Step 5) cyclizing under basic conditions the resultant compound of formula (X):

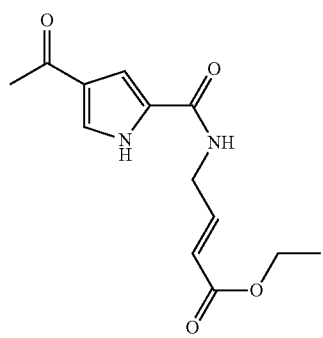
(X)

Step 6) mixing the resultant compound of formula (XI)

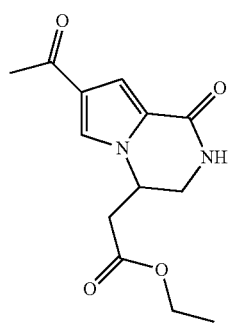
(XI)

with dimethylformamide-dialkylacetale;

Step 7) reacting the resultant compound of formula (XII)

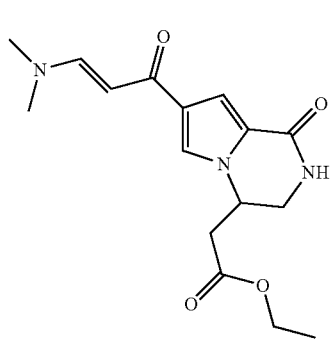
(XII)

with a compound of formula (XIII)

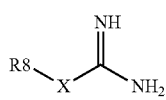
(XIII)

wherein X is a single bond or a divalent radical selected from —NR', —O— and S, wherein R' is hydrogen or an optionally substituted group selected from straight or branched $C_1$-$C_6$ alkyl, $C_3$-$C_7$ cycloalkyl, cycloalkylalkyl, heterocyclyl and heterocyclylalkyl; R8 is hydrogen or an optionally substituted group selected from amino, straight or branched $C_1$-$C_6$ alkyl, $C_3$-$C_7$ cycloalkyl, cycloalkyl-alkyl, aryl, arylalkyl, heterocyclyl and heterocyclylalkyl, to give a compound of formula (XIV)

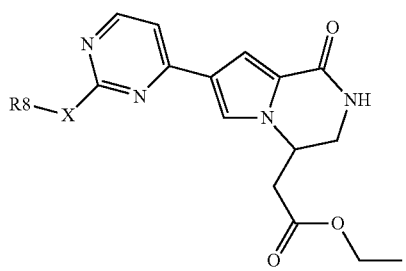
(XIV)

wherein X and R8 are as defined above.

The reported Scheme 3 shows the preparation of an intermediate compound of formula (XVII).

Scheme 3

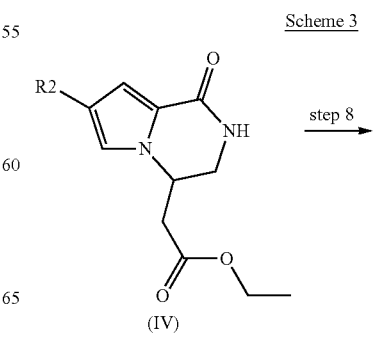
(IV)

-continued

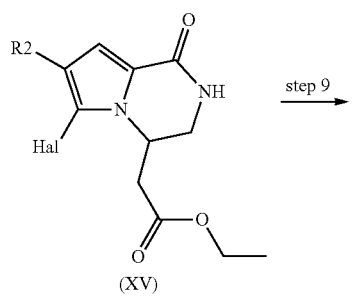

(XV)

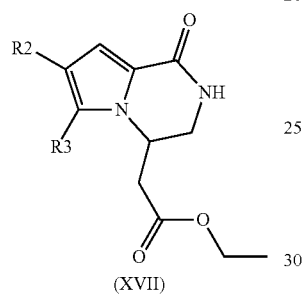

(XVII)

In the above Scheme 3, R2 is aryl, arylalkyl, heterocyclyl or heterocyclylalkyl; Hal is halogen; R3 is an optionally substituted group selected from straight or branched $C_1$-$C_6$ alkyl, $C_3$-$C_7$ cycloalkyl, cycloalkyl-alkyl, $C_2$-$C_6$ alkenyl, $C_2$-$C_6$ alkynyl, aryl, arylalkyl, heterocycyl and heterocycylalkyl.

Accordingly, a process of the present invention comprises the following steps:

Step 8) reacting the compound of formula (IV) as defined above, with an halogenating agent;

Step 9) mixing the resultant compound of formula (XV)

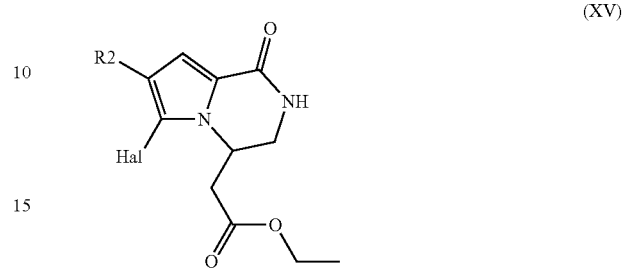

(XV)

wherein R2 is aryl, arylalkyl, heterocyclyl or heterocyclylalkyl, and Hal is halogen, with an organoboron compound of formula R3'-B(OZ)(OZ") (XVI) wherein R3' is an optionally substituted group selected from straight or branched $C_1$-$C_6$ alkyl, $C_2$-$C_6$ alkenyl, $C_2$-$C_6$ alkynyl, $C_3$-$C_7$ cycloalkyl, cycloalkyl-alkyl, aryl, arylalkyl, heterocyclyl and heterocyclylalkyl; and Z' and Z" are as defined above, so as to obtain a compound of formula (XVII)

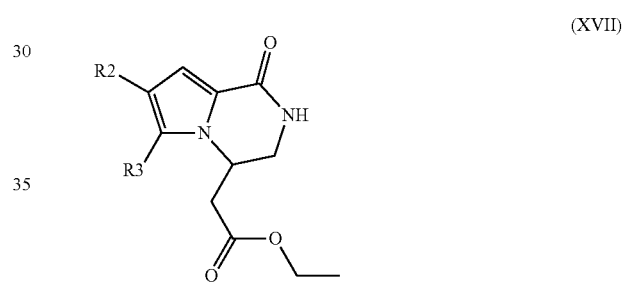

(XVII)

wherein R2 and R3 are as defined above.

The reported Scheme 4 shows the preparation of a compound of formula (I).

Scheme 4

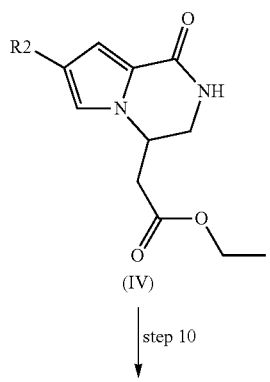

(IV)

↓ step 10

17

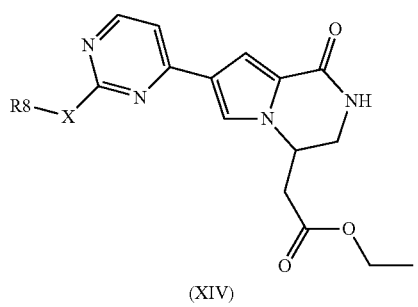

(XIV)

18

-continued

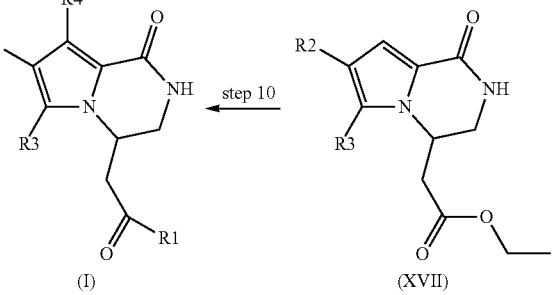

(I)    (XVII)

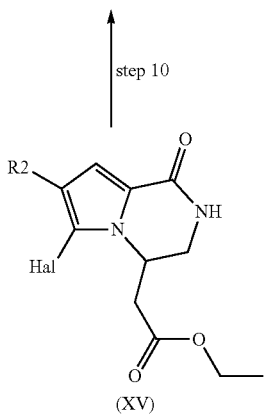

(XV)

In the above Scheme 4, X is a single bond or a divalent radical selected from —NR', —O— and 5, wherein R' is hydrogen or an optionally substituted group selected from straight or branched $C_1$-$C_6$ alkyl, $C_3$-$C_7$ cycloalkyl, cycloalkylalkyl, heterocyclyl and heterocyclylalkyl; R8 is hydrogen or an optionally substituted group selected from amino, straight or branched $C_1$-$C_6$ alkyl, $C_3$-$C_7$ cycloalkyl, cycloalkyl-alkyl, aryl, arylalkyl, heterocyclyl and heterocyclylalkyl; R1 is NR5R6, wherein R5 and R6 are hydrogen, an optionally substituted group selected from straight or branched $C_1$-$C_6$ alkyl, $C_2$-$C_6$ alkenyl, $C_2$-$C_6$ alkynyl, $C_3$-$C_7$ cycloalkyl, cycloalkyl-alkyl, aryl, arylalkyl, heterocyclyl and heterocyclylalkyl; or R5 and R6 together with the nitrogen atom to which they are bound, form a 5 to 7 membered heterocyclyl group optionally containing one additional heteroatom selected from N, O and S; R2 is aryl, arylalkyl, heterocyclyl or heterocyclylalkyl; R3 is hydrogen, halogen, or an optionally substituted group selected from straight or branched $C_1$-$C_6$ alkyl, $C_2$-$C_6$ alkenyl, $C_2$-$C_6$ alkynyl, $C_3$-$C_7$ cycloalkyl, cycloalkyl-alkyl, aryl, arylalkyl, heterocyclyl and heterocyclylalkyl; and R4 is hydrogen.

Accordingly, a process of the present invention comprises the following step:

Step 10) reacting a compound of formula (IV), (XIV), (XV), or (XVII) as defined above, with a compound of formula (VII)

R5R6NH    (VII)

wherein R5 and R6 are hydrogen, an optionally substituted group selected from straight or branched $C_1$-$C_6$ alkyl, $C_2$-$C_6$ alkenyl, $C_2$-$C_6$ alkynyl, $C_3$-$C_7$ cycloalkyl, cycloalkyl-alkyl, aryl, arylalkyl, heterocyclyl and heterocyclylalkyl; or R5 and R6 together with the nitrogen atom to which they are bound, form a 5 to 7 membered heterocyclyl group optionally containing one additional heteroatom selected from N, O and S, to give a compound of the formula (I)

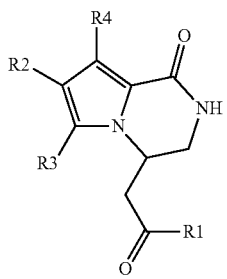

(I)

wherein R1 is NR5R6, wherein R5 and R6 are hydrogen, an optionally substituted group selected from straight or branched $C_1$-$C_6$ alkyl, $C_2$-$C_6$ alkenyl, $C_2$-$C_6$ alkynyl, $C_3$-$C_7$ cycloalkyl, cycloalkyl-alkyl, aryl, arylalkyl, heterocyclyl and heterocyclylalkyl; or R5 and R6 together with the nitrogen atom to which they are bound, form a 5 to 7 membered heterocyclyl group optionally containing one additional heteroatom selected from N, O and S; R2 is aryl, arylalkyl, heterocyclyl and heterocyclylalkyl; R3 is hydrogen, halogen, or an optionally substituted group selected from straight or branched $C_1$-$C_6$ alkyl, $C_2$-$C_6$ alkenyl, $C_2$-$C_6$ alkynyl, $C_3$-$C_7$ cycloalkyl, cycloalkyl-alkyl, aryl, arylalkyl, heterocyclyl and heterocyclylalkyl; and R4 is hydrogen;

optionally converting a compound of the formula (I) into another different compound of the formula (I), and if desired, converting a compound of the formula (I) into a pharmaceutically acceptable salt thereof or converting a salt into the free compound (I).

As said above, the compounds of the formula (I) which are prepared according to the process object of the invention, can be conveniently converted into other compounds of the formula (I) by operating according to well-known synthetic conditions, the following being examples of possible conversions:

Conv. a) converting a compound of formula (I) wherein R3 or R4 is hydrogen into the corresponding compound of formula (I) wherein R3 or R4 is an halogen

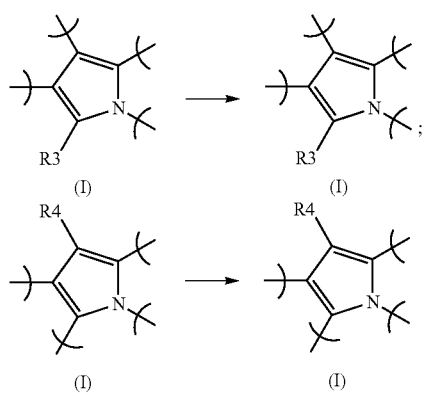

through reaction with an halogenating agent;

Conv. b) converting a compound of formula (I) wherein R3 or R4 is halogen into the corresponding compound of formula (I) wherein R3 or R4 is an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl

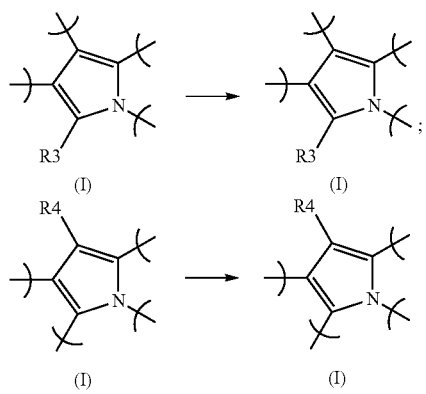

by reaction with a compound of formula (XVIII) or (XX) respectively:

R3''-G (XVIII)

R4'-G (XX)

wherein R3'' or R4' is an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl, and G is a suitable group such as —B(OH)$_2$, —B(OAlk)$_2$, —Sn(Alk)$_4$, ZnHal, or MgHal, under palladium mediated carbon bond formation;

Conv. c) converting a compound of formula (I) wherein R3 or R4 is halogen into the corresponding compound of formula (I) wherein R3 or R4 is an alkyne

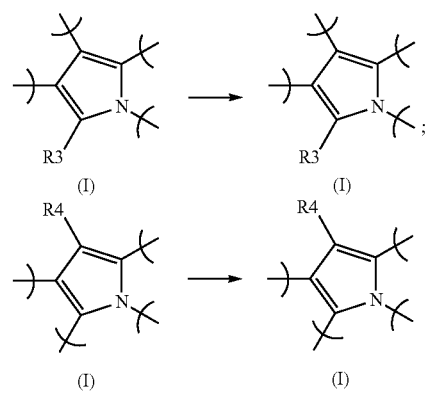

by reaction with a terminal alkyne of formula (XIX):

$$R^aC\equiv CH \quad (XIX)$$

wherein $R^a$ is hydrogen, or an optionally substituted group selected from straight or branched $C_1$-$C_6$ alkyl, $C_2$-$C_6$ alkenyl, $C_2$-$C_6$ alkynyl, $C_3$-$C_7$ cycloalkyl, cycloalkyl-alkyl, aryl, arylalkyl, heterocyclyl and heterocyclylalkyl, under palladium mediated carbon bond formation;

Conv. d) converting a compound of formula (I) wherein R3 or R4 is halogen into the corresponding compound of formula (I) wherein R3 or R4 is cyano

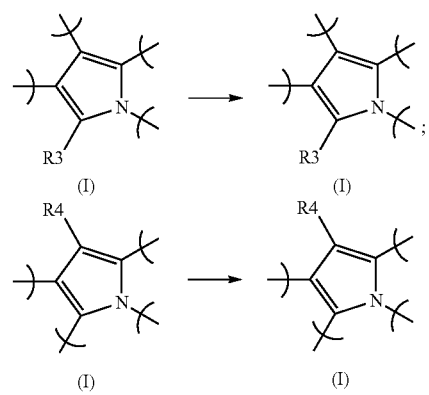

following the condition known in the art for palladium-catalyzed cyanation of aryl halides;

Conv. e) removing any protecting group or groups and, if desired, forming a salt.

According to Step 1 of the process, the compound of the formula (II) is coupled with a derivative of formula (III) exploiting any of the cross-coupling reactions suitable for the formation of carbon-carbon bonds. Said reactions, which are well known in the art, imply coupling with a suitable organometal reagent such as for instance organoboron (Suzuki reaction), organotin (Stille reaction), organomagnesium (Kumada reaction), or organozinc (Negishi reaction) and the like. Preferred reaction is the Suzuki reaction where the appropriate aryl or heteroharylboronic derivative is used in the presence of a palladium based catalyst such as PdCl$_2$(dppf)$_2$CH$_2$Cl$_2$ or Pd$_2$(dba)$_3$ or Pd(PPh$_3$)$_4$. Convenient solvents include aprotic solvents such as DMF, DCM, MeOH, CH$_3$CN, or in a mixture of solvents, such as dimethoxyethane and water, optionally in the presence of a base such as sodium, cesium carbonate or cesium fluoride, at a temperature ranging from room temperature to 100° C.

According to Step 2 of the process, a compound of formula (II) is transformed into an organometal derivative of formula (V) such as an organoboron or the like. Preferred organometal are organonboron compounds that can be obtained for instance reacting a compound of formula (II) with a suitable boron compound, such as bis(pinacolato)diboron, pinacolborane, or the like in the presence of a suitable palladium catalyst such as palladium acetate, $PdCl_2(dppf)_2$ and a suitable base, such as KOAc, triethylamine and the like, in solvents such as DMF, 1,4-dioxane, dimethoxyethane, THF or the like, at temperature ranging from 20° C. to reflux and for a time ranging from 30 minutes to about 24 hours.

According to Step 3 of the process, a compound of formula (V) is reacted with an appropriate electrophile of formula R2-Q (VI), wherein Q is an halide or a trifluoromethansulfonate (triflate), a methansulfonate (mesylate) or a p-toluenesulfonate (tosylate) in the presence of a palladium or nickel-based catalyst, such as for instance, tetrakis(triphenylphosphine)palladium, or $PdCl_2(dppf)_2CH_2Cl_2$, and a suitable base, such as $Cs_2CO_3$, $K_2CO_3$, CsF, and the like. Convenient solvents include aprotic solvents such as 1,4-dioxane, dimethoxyethane, THF or the like, at temperature ranging from 20° C. to reflux and for a time ranging from 1 hour to about 24 hours, to give a compound of formula (IV).

According to Step 4 of the process, the compound of formula (IX) can be transformed into the corresponding amido derivative of formula (X), in a variety of ways according to conventional methods for obtaining amido derivatives from the corresponding $\alpha,\alpha,\alpha$-trichloroketones. Preferably the reaction is carried out by reaction of an amine of formula (IX) with a trichloroketone derivative of formula (VIII) in the presence of N,N-diisopropylethylamine, using dichloromethane as the solvent, for a time varying from about 2 hours to 48 hours.

According to Step 5 of the process, the cyclization of the compound of formula (X) into the corresponding derivative of formula (XI) can be carried out in a variety of ways according to conventional methods. Preferably, the reaction is carried out using a base such as diaza(1,3)bicyclo[5.4.0]undecane and acetonitrile as the solvent.

According to Step 6 of the process, the synthesis of the enaminone derivative of formula (XII) is accomplished using a N,N-dimethylformamide dialkyl acetal, such as, for instance dimethylformamide-di-tert-butylacetale, dimethylformamide-diethylacetale and the like in a suitable solvent such as DMF, DMA, toluene, or the like at a temperature ranging from room temperature to 150° C., and for a time ranging from 30 minutes to about 24 hours.

According to Step 7 of the process, the compound of the formula (XII) is reacted with a derivative of formula (XIII) so to obtain a compound of the formula (XIV) through pyrimidine ring formation in the presence of a base such as AcOK, $K_2CO_3$ or $Na_2CO_3$ in a suitable solvent such as, for instance, DMF, EtOH or toluene, at a temperature ranging from room temperature to reflux, and for a time ranging from about 1 to about 48 hours. Preferably, the reaction is carried out in DMF at 120° C., for 18 hours.

According to Step 8 of the process, the compound of formula (IV) can be transformed into the corresponding compound of formula (XV) by reaction with a halogenating agent. The said reaction is performed with a halogenating reagent such as NBS or NIS, in a suitable solvent such as DCM or DMF, from −10° C. to room temperature in a period of time varying from 2 hours to about 18 hours. Preferably, the reaction is carried out under neutral conditions in the presence of iodine and silver trifluoroacetate, in DCM at a temperature ranging from 0° C. to room temperature and for a time varying from 2 hours to overnight.

According to Step 9 of the process, a compound of formula (XV) is reacted with an organoboron of formula R3'-B(OZ'Z")$_2$ (XVI) in a suitable solvent such as DMF, 1,4-dioxane, DME or $CH_3CN$, in the presence of $Pd_2(dba)_3$, $PdCl_2$(dppf) or $Pd(PPh_3)_4$, optionally in the presence of cesium fluoride or cesium carbonate, at a temperature ranging from room temperature to 100° C. for a time ranging from 2 hours to 6 hours.

According to Step 10 of the process, a compound of formula (IV), (XIV), (XV) or (XVII) is first hydrolyzed into the corresponding carboxylic acid derivative or its corresponding salt through basic or acidic hydrolysis conditions, widely known in the art. Preferably, the reaction is carried out with aqueous alkaline solutions such as aqueous lithium, sodium or potassium hydroxide in the presence of a suitable solvent such as a lower alcohol, THF, DMF or mixtures thereof; preferably the reaction is carried out with potassium hydroxide in ethanol, at a temperature ranging from about room temperature to about 80° C. According to the operative conditions being employed, the carboxylic acid derivative could be obtained either in its acidic form or, alternatively, as a salt. Then the amidation of the carboxylic acid derivative to give the compound of formula (I), is carried out in the presence of ammonium chloride or a suitable primary or secondary amine of formula R5R6NH (VII), under basic conditions, preferably with DIPEA or TEA, in a suitable solvent such as DCM, DMF, THF, 1,4-dioxane, or DMA, in the presence of a suitable condensing agent, for instance dicyclohexylcarbodiimide (DCC), 1-ethyl-3-(3'-dimethylaminopropyl)carbodiimide (EDC), 3,4-dihydro-3-hydroxy-4-oxo-1,2,3-benzotriazine (DHBT), 0-benzotriazolyltetramethylisouronium tetrafluoroborate (TBTU), benzotriazol-1-yloxytripyrrolidinophosphonium hexafluorophosphate (PyBOP), or 2-(1H-Benzotriazole-1-yl)-1,1,3,3-tetramethyluronium hexafluorophosphate (HBTU). The said reaction is optionally carried out in the presence of a suitable catalyst such as the 4-dimethylaminopyridine, or in the presence of a further coupling reagent such as N-hydroxybenzotriazole.

Alternatively, the direct transformation of compounds of formula (IV), (XIV), (XV) or (XVII) into a compound of formula (I), can be performed according to methods well-known in the art to convert carboxyester groups (—COOEt) into carboxamides (—$CONH_2$), N-substituted carboxamides (—CONHR5), N,N-disubstituted carboxamides (—CONR5R6. Preferably the reaction is carried out with ammonia in methanol, at a temperature ranging from about 50° C. to about 100° C. Analogous operative conditions are applied in the preparation of N-substituted carboxamides or N,N-disubstituted carboxamides wherein a suitable primary or secondary amine are used in place of ammonia or ammonium hydroxide.

According to conversion (conv. a) of the process, a compound of the formula (I) wherein R3 or R4 is hydrogen is converted into the corresponding compound of formula (I) wherein R3 or R4 is halogen. The said reaction is performed with halogenating reagent such as NCS, NBS, NIS, in a suitable solvent such as DCM, THF, MeOH, DMF or a mixture thereof, from 0° C. to room temperature within 2 to about 18 hours. Preferably, the reaction is carried out under neutral conditions in the presence of iodine and silver trifluoroacetate, in DCM at a temperature ranging from 0° C. to room temperature and for a time from 2 hours to overnight.

According to conversion (cow b) of the process, a compound of the formula (I) wherein R3 or R4 is halogen is converted into the corresponding compound of formula (I) wherein R3 or R4 is an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl, by exploiting any of the cross-coupling reactions suitable for the formation of carbon-carbon bonds.

Said reactions, which are well known in the art, imply coupling with a suitable organometal reagent such as for instance organoboron (Suzuki reaction), organotin (Stille reaction), organomagnesium (Kumada reaction), organozinc, or organoalluminium, or organozirconium (Negishi reaction) and the like. Preferred reaction is the Suzuki reaction where the appropriate organoboron derivative is used in the presence of a palladium based catalyst such as $PdCl_2(dppf)_2CH_2Cl_2$ and a base such as sodium or potassium or cesium carbonate, in a mixture of solvents, such as dimethoxyethane or 1,4-dioxane and water, at a temperature varying from room temperature to 80° C. and for a time between 2 hours to overnight.

According to conversion (conv. c) of the process, a compound of formula (I) wherein R3 or R4 is halogen, is converted into the corresponding compound of formula (I) wherein R3 or R4 is an alkyne by reaction with compound of formula (XIX). The reaction is carried out through the Sonogashira coupling to give the corresponding compound of formula (I) in the presence of suitable Pd-catalysts include $Pd(PPh_3)_4$, $Pd(PPh_3)_2Cl_2$, suitable ligands include tryphenylphosphine, and an additive such as copper(I) iodide, using N,N-dimethylformamide as the solvent, at a temperature varying from room temperature to reflux and for a time ranging between 4 hours and overnight. According to conversion (conv. d) of the process, a compound of formula (I) wherein R3 or R4 is Br or iodine can be converted into the corresponding compound of formula (I) wherein R3 or R4 is CN, following the condition reported for palladium-catalyzed cyanation of aryl halides. The said reaction is performed by using ZnCN or potassium hexacyanoferrate$^{(II)}$ as a source of cyanide in the presence of palladium$^{(II)}$ acetate as catalyst, sodium carbonate, potassium carbonate or cesium carbonate as base, in a suitable solvent such as DMF, N-methylpyrrolidone, or DMA, from 80° C. to reflux, for a time ranging from 4 to about 24 hours (J. Org. Chem. 2005, 70, 1508-1510, Org. Lett., 2011, 13(4), pp 648-651).

According to conversion (conv. e) of the process, a compound of formula (I) wherein R' is a protecting group can be converted into the corresponding compound of formula (I) wherein R' is hydrogen, by deprotection of the nitrogen atom according to conventional methods enabling the selective hydrolysis of tert-butoxycarbonyl, benzyl, 4-methoxybenzyl, 2,4-dimethoxybenzyl, and triphenylmethylprotective groups. Preferably this reaction is run under acidic conditions, for instance in the presence of an inorganic or organic acid such as hydrochloric, trifluoroacetic or methansulfonic acid, in a suitable solvent such as DCM, 1,4-dioxane, a lower alcohol, such as methanol or ethanol, at a temperature ranging from room temperature to reflux and for a period of time ranging from about 1 hour to about 48 hours.

From all of the above, it is clear to the skilled person that any compound of formula (I) bearing a functional group which can be further derivatized to another functional group, by working according to methods well known in the art thus leading to other compounds of the formula (I), is intended to be comprised within the scope of the present invention.

It is known to the skilled person that conversion of a chemical function into another may require that one or more reactive centers in the compound containing this function be protected in order to avoid undesired side reactions. Protection of such reactive centers, and subsequent deprotection at the end of the synthetic transformations, can be accomplished following standard procedures described, for instance, in: Green, Theodora W. and Wuts, Peter G. M.—Protective Groups in Organic Synthesis, Third Edition, John Wiley & Sons Inc., New York (N.Y.), 1999.

According to any variant of the process for preparing the compounds of formula (I), the starting materials and any other reactants are known or easily prepared according to known methods.

The compounds of formula (II), (VIII) and (IX), can be prepared as described in WO2010/031816.

The compounds of formula (III), (VI), (VII), (XIII), (XVI), (XVIII), (XIX) and (XX) are either commercially available or can be prepared with known methods.

From all of the above, it is clear to the skilled person that, when preparing the compounds of formula (I) according to any one of the aforementioned process variants, optional functional groups within the starting materials or the intermediates thereof that could give rise to unwanted side reactions, need to be properly protected according to conventional techniques. Likewise, the conversion of these latter into the free deprotected compounds may be carried out according to known procedures.

As it will be readily appreciated, if the compounds of formula (I) prepared according to the process described above are obtained as mixture of isomers, their separation using conventional techniques into the single isomers of formula (I), is within the scope of the present invention.

Conventional techniques for racemate resolution include, for instance, partitioned crystallization of diastereoisomeric salt derivatives or preparative chiral HPLC.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of formula (I) may range from about 10 to about 1000 Mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose, saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example; the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim of better illustrating the present invention, without posing any limitation to it, the following examples are now given.

EXAMPLES

The synthetic preparation of some compounds of formula (I) of the invention is described in the following examples. The compounds of the present invention, as prepared according to the following examples, were also characterized by $^1$H NMR or by HPLC/MS analytical data; HPLC/MS data were collected following any one of methods 1, 2, 3 and 4.

HPLC/MS Analytic Method 1

The HPLC equipment consisted of a Waters Acquity™ UPLC system equipped with a Waters 2996 PDA detector, a Waters Acquity ELSD™ detector and Waters mod. SQD single quadrupole mass spectrometer, equipped with an electrospray (ESI) ion source. Instrument control, data acquisition and data processing were provided by Empower 2 and MassLynx 4.1 softwares.

HPLC was carried out at 45° C. at a flow rate of 0.7 mL/min using a Waters Acquity™ BEH C18, 1.7 μm, 50×2.1 mm column. Mobile phase A was 0.1% trifluoro acetic acid in water/acetonitrile (95:5), and mobile phase B was $H_2O$/acetonitrile (5:95); the gradient was from 5 to 95% B in 2 minutes then hold 95% B 0.1 minutes. The injection volume was 0.8 μL. The mass spectrometer was operated in positive and in negative ion mode, the capillary voltage was set up at 3 KV ($ES^+$ and $ES^-$); cone was 30 V ($ES^+$ and $ES^-$); the source temperature was 120° C.; full scan, mass range from 100 to 800 amu was set up.

HPLC/MS Analytic Method 2

HPLC/MS analyses were performed on a Finnigan MAT mod. LCQ ion trap mass spectrometer, equipped with an ESI (Electrospray) ion source, the mass spectrometer is directly connected to a HPLC SSP4000 (Thermo Separation) equipped with an autosampler Lc Pal (CTC Analytics) and an UV6000LP PDA detector.

HPLC was carried out at 40° C. at a flow rate of 1.0 mL/min using a Phenomenex Gemini C18, 3 μm, 50×4.6 mm column. Mobile phase A was Acetate Buffer 5 mM pH 4.5:acetonitrile 95:5 (v:v), and mobile phase B was Acetate Buffer 5 mM pH 4.5:acetonitrile 5:95 (v:v) the gradient was from 0 to 100% B in 7 minutes then hold 100% B for 2 minutes before requilibration. Total LC time was 10 minutes. The injection volume was 10 μl.

MS conditions: the LCQ mass spectrometer operates with electrospray ionization (ESI) interface in positive and negative ion mode. ESI sprayer voltage 4.0 kV, heated capillary temperature 255° C., sheath gas nitrogen with a pressure of 5.0 Bar. A full scan detection mode (from 50 to 1000 amu) was used.

MS/MS experiments were performed on the most intense ion of each scan automatically by Excalibur software. 45% collision energy was used for the fragmentation of the precursor ions.

HPLC/MS Analytic Method 3

The HPLC equipment consisted of a Waters Alliance™ HT 2795 system equipped with a Waters 2996 PDA detector and Waters mod. ZQ 2000 single quadrupole mass spectrometer, equipped with an electrospray (ESI) ion source. Instrument control, data acquisition and data processing were provided by Empower 2 and MassLynx 4.1 softwares. HPLC was carried out at 25° C. at a flow rate of 1.0 mL/min using a Phenomenex Gemini C18, 3 μm, 50×4.6 mm column. Mobile phase A was ammonium acetate 5 mM pH=5.2 buffer with acetonitrile (95:5), and mobile phase B was $H_2O$/acetonitrile (5:95); the gradient was from 10 to 90% B in 8 minutes then ramp to 100% B in 0.1 minutes. The injection volume was 10 μL. The mass spectrometer was operated in positive and in negative ion mode, the capillary voltage was set up at 3.5 kV ($ES^+$) and 2.8 kV ($ES^-$); cone voltage was 14 V ($ES^+$) and 28 V ($ES^-$); the source temperature was 120° C.; full scan, mass range from 100 to 800 amu was set up.

HPLC/MS analytic Method 4

The HPLC equipment consisted of a Waters Alliance™ HT 2795 system equipped with a Waters 2996 PDA detector and Waters mod. ZQ 2000 single quadrupole mass spectrometer, equipped with an electrospray (ESI) ion source. Instrument control, data acquisition and data processing were provided by Empower 2 and MassLynx 4.1 softwares. HPLC was carried out at 25° C. at a flow rate of 1.2 mL/min using a Waters X-Terra RP18, 3.5 μm, 20×3.0 mm column. Mobile phase A was ammonium hydroxide 0.05% pH=10 buffer with acetonitrile (95:5), and mobile phase B was H₂O/acetonitrile (5:95); the gradient was from 10 to 90% B in 4 minutes then ramp to 100% B in 0.1 minutes. The injection volume was 10 μL. The mass spectrometer was operated in positive and in negative ion mode, the capillary voltage was set up at 3.5 kV (ES⁺) and 2.8 kV (ES⁻); cone voltage was 14 V (ES⁺) and 28 V (ES⁻); the source temperature was 120° C.; full scan, mass range from 100 to 800 amu was set up.

Several compounds of the invention of the formula (I), as prepared according to the following examples, were purified by preparative HPLC. The operative conditions are defined below:

HPLC/MS Preparative Method 1

The HPLC equipment consisted of a Waters FractionLynx™ system equipped with a Waters 2996 PDA detector and Waters mod. ZQ 2000 single quadrupole mass spectrometer, equipped with an electrospray (ESI) ion source. Instrument control, data acquisition and data processing were provided by MassLynx4.1 software.

HPLC was carried out at 25° C. at a flow rate of 20 mL/min using a Waters X-Terra Prep RP18, 10 μm, 250×19 mm column. Mobile phase A was 0.1% trifluoro acetic acid in water/acetonitrile (95:5), and mobile phase B was acetonitrile; the gradient was from 10 to 90% B in 15 minutes. The injection volume was 500 μL.

The mass spectrometer was operated in positive and in negative ion mode, the capillary voltage was set up at 3.25 kV (ES⁺) and 2.75 kV (ES⁻); cone voltage was 18 V (ES⁺) and 25 V (ES⁻); the source temperature was 120° C.; full scan, mass range from 100 to 800 amu was set up.

HPLC preparative Method 2

The HPLC equipment consisted of a Shimadzu HPLC system equipped with SCL-8A System Controller, two LC-8A Pumps, SPD-6A UV Spectrophotometric Detector and manual Rheodyne injection system. Data acquisition (analogic signal) and data processing were provided by Empower 2 software.

HPLC was carded out at 25° C. at a flow rate of 40 mL/min using a Waters X-Terra MS RP18, 10 μm, 150×30 mm column. Mobile phase A was 0.1% trifluoro acetic acid in water/acetonitrile (95:5), and mobile phase B was H₂O/acetonitrile (5:95); the gradient was from 10 to 90% B in 15 minutes then ramp to 100% B in 0.1 minutes. The injection volume was 500 μL.

Exact Mass

Exact mass data ESI(+) were obtained on a Waters Q-Tof Ultima directly connected with micro HPLC 1100 Agilent as previously described (M. Colombo, F. Riccardi-Sirtori, V. Rizzo, *Rapid Commun. Mass Spectrom.* 2004, 18, 511-517).

¹H-NMR spectrometry was performed on a Bruker AVANCE 400 MHz single bay instrument with gradients. It was equipped with a QNP probe (interchangeable 4 nuclei probe—¹H, ¹³C, ¹⁹F and ³¹P) (NMR method 1) or on a Mercury VX 400 operating at 400.45 MHz equipped with a 5 mm double resonance probe 5 mm ¹H{¹⁵N-³¹P}z-axis-PFG indirect detection probe.

¹H-NMR spectrometry was performed on a Varian INOVA 599.88 MHz equipped with a ¹H, ¹⁹F z-axis-PFG probe.

Preparation A

Ethyl [7-(3-chlorophenyl)-1-oxo-1,2,3,4-tetrahydropyrrolo[1,2-a]pyrazin-4-yl]acetate [(IV) R2=3-chlorophenyl]

Step 1

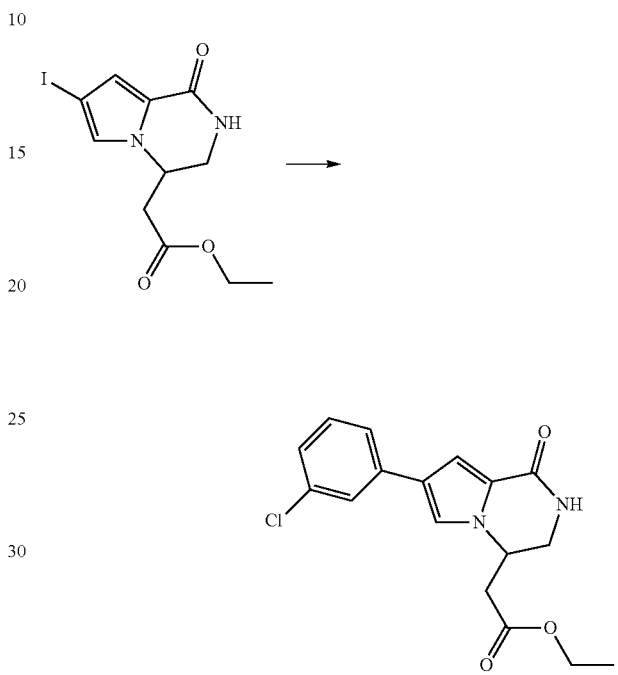

To a solution of ethyl (7-iodo-1-oxo-1,2,3,4-tetrahydropyrrolo[1,2-a]pyrazin-4-yl)acetate (1.00 g, 2.87 mmol) in a degassed (with Ar stream) mixture of 1,4-dioxane/H₂O (25/5 mL) 3-chloro-phenylboronic acid (898 mg, 5.74 mmol), cesium carbonate (2.807 g, 8.61 mmol), and at the end 1,1'-bis(diphenylphosphino)ferrocenepalladium(II) dichloride, complex with dichloromethane (1:1) (234 mg 0.287 mmol) were added. The reaction mixture was capped under argon atmosphere and stirred at 80° for 2 h. The solvent was evaporated under vacuum and the residue partitioned between ethyl acetate and water. The organic phase was dried on Na₂SO₄ and concentrated to dryness. The crude was purified by chromatography on a silica gel column (eluent: DCM/EtOAc/EtOH: 60/35/5) to afford 0.573 g (60% yield) as a light brown solid.

¹H NMR (400 MHz, DMSO-d6) δ 7.71 (d, J=1.22 Hz, 1H), 7.64 (t, J=1.83 Hz, 1H), 7.58 (d, J=1.83 Hz, 1H), 7.51-7.56 (m, 1H), 7.35 (t, J=7.93 Hz, 1H), 7.20 (ddd, J=0.98, 2.08, 7.93 Hz, 1H), 7.10 (d, J=1.83 Hz, 1H), 4.60-4.69 (m, 1H), 4.11 (dq, J=1.16, 7.10 Hz, 2H), 3.71 (ddd, J=1.89, 4.18, 13.09 Hz; 1H), 3.35-3.42 (m, 1H), 2.89 (dd, J=5.13, 6.84 Hz, 2H), 1.18 (t, J=7.08 Hz, 3H)

HRMS (ESI) calcd for C₁₇H₁₈ClN₂O₃ [M+H]⁺ 333.1001 found 333.1005.

Preparation B

Ethyl [1-oxo-7-(4,4,5,5-tetramethyl-1,3,2-dioxaborolan-2-yl)-1,2,3,4-tetrahydropyrrolo[1,2-a]pyrazin-4-yl]acetate [(V), Z',Z''=—C(Me)$_2$-C(Me)$_2$-]

Step 2

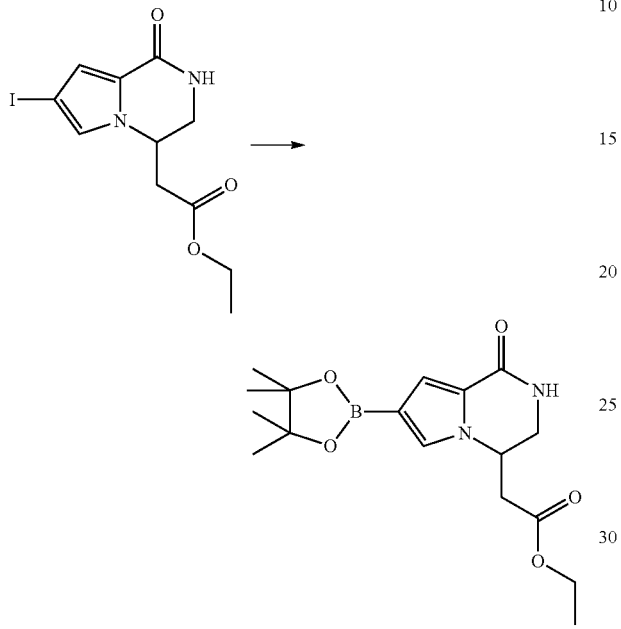

Ethyl (7-iodo-1-oxo-1,2,3,4-tetrahydropyrrolo[1,2-a]pyrazin-4-yl)acetate (200 mg, 0.57 mmol) was reacted with Bis(pinacolato)diboron (729 mg, 2.8 mmol) in the presence of potassium acetate (170 mg, 1.7 mmol) and [1,1'-Bis(diphenylphosphino)ferrocene]dichloropalladium(II), complex with dichloromethane (28 mg, 0.034 mmol) in dry DMF (18 ml) for 3 hours at 70° C. The crude was worked up with water and AcOEt, filtered, evaporated and finally purified on silica gel (eluent: AcOEt/Hex 9/1) to give the wanted compound as a clear oil in 40% yield.

$^1$H NMR (400 MHz, DMSO-d$_6$) δ 7.67 (d, J=2.32 Hz, 1H), 7.24 (d, J=1.46 Hz, 1H), 6.76 (d, J=1.59 Hz, 1H), 4.59-4.70 (m, 1H), 4.04-4.14 (m, 2H), 3.63 (ddd, J=1.65, 4.18, 12.97 Hz, 1H), 3.34-3-39 (m, 1H), 2.83 (d, J=7.20 Hz, 2H), 1.24 (s, 12H), 1.13-1.19 (m, 3H).

LCMS (HPLC Method 2): m/z 348 [M+H]$^+$ @ r.t. 5.31 min.

HRMS (ESI) calcd for C$_{17}$H$_{25}$BN$_2$O$_5$ [M+H]$^+$ 348.1966. found 348.1953

Example 1

2-[(4R)-7-(3-chlorophenyl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide [(I) R2=3-chlorophenyl, R3=R4=H, R1=—NH—R5, R5=-(1S)-1-cyclohexyl-2-(4-methylpiperazin-1-yl)ethyl](cpd 1) and 2-[(4S)-7-(3-chlorophenyl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide [(I) R2=3-chlorophenyl, R3=R4=H, R1=—NH—R5, R5=-(1S)-1-cyclohexyl-2-(4-methylpiperazin-1-yl)ethyl](cpd 2)

Step 10

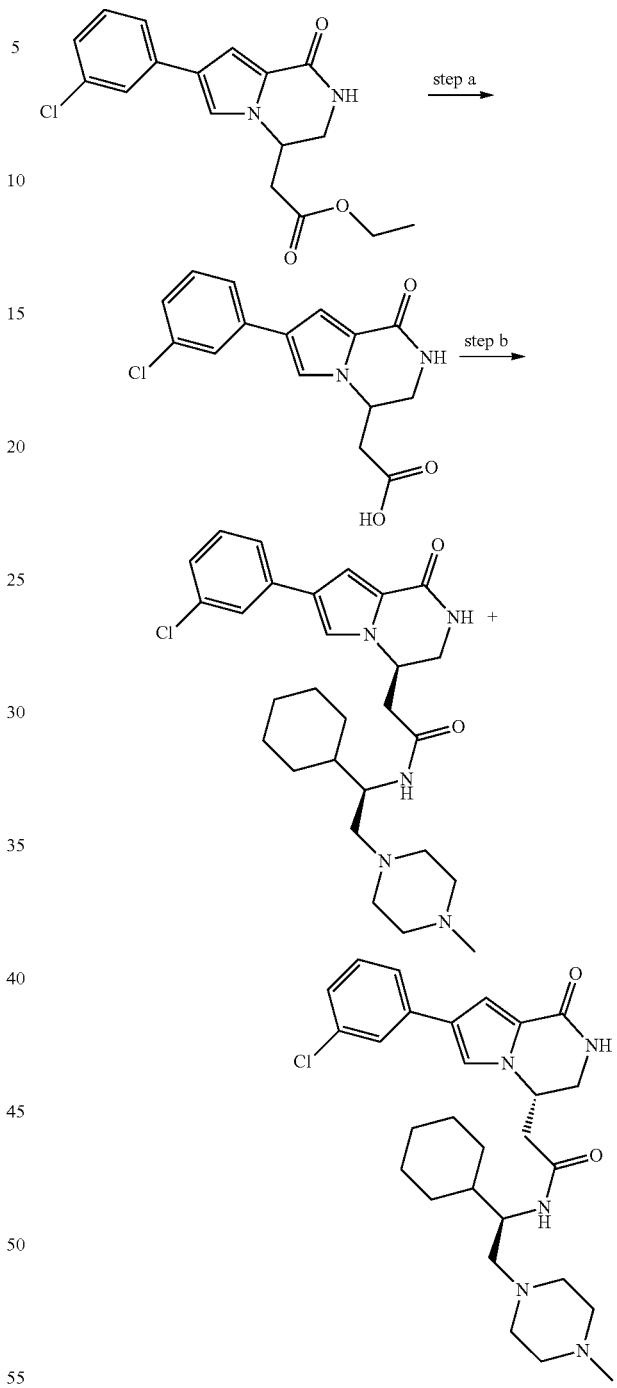

Step a. Preparation of [7-(3-chlorophenyl)-1-oxo-1,2,3,4-tetrahydropyrrolo[1,2-a]pyrazin-4-yl]acetic acid To a solution of ethyl [7-(3-chlorophenyl)-1-oxo-1,2,3,4-tetrahydropyrrolo[1,2-a]pyrazin-4-yl]acetate (0.573 g, 1.72 mmol) in a mixture tetrahydrofuran-water (5:1, 10 mL), lithium hydroxide (144 mg, 3.44 mmol) was added and the reaction mixture was stirred at room temperature for 18 h. The THF was evaporated and the aqueous residue diluted with H$_2$O. The aqueous phase was acidified with hydrochloric acid (1 M) until pH<1 and a precipitation occurred; the solid was filtered, washed with water and dried under vacuum to obtain the title compound as an off-white solid (450 mg, 85% yield).

LCMS (HPLC Method 2): m/z 305 [M+H]+ @ r.t. 4.11 min.

HRMS (ESI) calcd for $C_{15}H_{14}ClN_2O_3$ [M+H]+ 305.0688 found 305.0691.

Step b. A solution of 7-(3-chlorophenyl)-1-oxo-1,2,3,4-tetrahydropyrrolo[1,2-a]pyrazin-4-yl]acetic acid (63 mg, 0.207 mmol), N,N-diisopropylethylamine (DIPEA) (0.361 ml, 2.067 mmol) and HBTU (94 mg, 0.248 mmol) in dry dioxane (25 ml) was stirred for 15 min, then was added to (1S)-1-cyclohexyl-2-(4-methylpiperazin-1-yl)ethanamine trihydrochloride (83 mg, 0.248 mmol) and the final suspension was stirred for 2 h at 70° C. The solvent was removed in vacuo. The crude was then portioned between ethyl acetate and water, the organic layer dried over sodium sulphate and the solvent removed in vacuo. Purification by flash chromatography on silica gel column (DCM/MeOH/NH4OH 90110/0.5 and 80/20/0.5) gave as first eluted peak the compound 2-[(4R)-7-(3-chlorophenyl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide as a light yellow foam 45 mg 42% Y.

$^1$H NMR (400 MHz, DMSO-d6) δ 7.74 (d, J=2.56 Hz, 1H), 7.68 (d, J=9.15 Hz, 1H), 7.60 (t, J=1.89 Hz, 1H), 7.52 (td, J=1.22, 8.06 Hz, 1H), 7.47 (d, J=1.83 Hz, 1H), 7.34 (t, J=7.87 Hz, 1H), 7.19 (ddd, J=0.85, 2.07, 7.93 Hz, 1H), 7.08 (d, J=1.83 Hz, 1H), 4.58-4.71 (m, 1H), 3.82 (td, J=7.28, 14.37 Hz, 1H), 3.62-3.69 (m, 1H), 2.77 (dd, J=7.26, 14.95 Hz, 1H), 2.63 (dd, J=6.35, 14.89 Hz, 1H), 2.33-2.10 (m, 10H), 2.02 (s, 3H), 1.58 (m, 4H), 1:36 (m, 1H), 1.15-0.90 (m, 5H).

LCMS (HPLC Method 2): m/z 512 [M+H]+ @ r.t. 5.17 min.

HRMS (ESI) calcd for $C_{28}H_{39}ClN_5O_2$ [M+H]+ 512.2787 found 512.2778.

and gave as second eluted peak the compound 2-[(4S)-7-(3-chlorophenyl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide as a light yellow foam 45 mg 42% Y.

$^1$H NMR (400 MHz, DMSO-d6) δ 7.72 (d, J=2.93 Hz, 1H), 7.62 (d, J=9.40 Hz, 1H), 7.58 (t, J=1.83 Hz, 1H), 7.49-7.53 (m, 1H), 7.39 (d, J=1.83 Hz, 1H), 7.33 (t, J=7.87 Hz, 1H), 7.18 (ddd, J=0.98, 2.08, 7.93 Hz, 1H), 7.09 (d, J=1.83 Hz, 1H), 4.59-4.74 (m, J=5.86 Hz, 1H), 3.75-3.89 (m, J=5.49 Hz, 1H), 3.70 (ddd, J=1.53, 4.27, 13.00 Hz, 1H), 3.39 (m, 2H), 2.77 (dd, J=8.12, 14.59 Hz, 1H), 2.56 (dd, J=5.68, 14.59 Hz, 1H), 2.40-2.17 (m, 10H), 2.11 (s, 3H), 1.68 (m, 1H), 1.51-1.35 (m, 4H), 1.28-1.20 (m, 1H), 1.10-0.75 (m, 5H).

LCMS (HPLC Method 2): m/z 512 [M+H]+ @ r.t. 5.34 min.

HRMS (ESI) calcd for $C_{26}H_{39}ClN_5O_2$ [M+H]+ 512.2787 found 512.2776.

According to this same methodology, but employing suitable substituted derivatives, the following compounds were prepared:

N-[(1S)-1-cyclohexyl-2-(4-methylpiperazin-1-yl)ethyl]-2-[(4R)-7-(3-fluorophenyl)-1-oxo-1,2,3,4-tetrahydropyrrolo[1,2-a]pyrazin-4-yl]acetamide [(I) R2=3-fluorophenyl, R3=R4=H, R1=—NH—R5, R5=-(1S)-1-cyclohexyl-2-(4-methylpiperazin-1-yl)ethyl](cpd 3)

1H NMR (400 MHz, DMSO-d6) δ 7.65-7.77 (m, 3H), 7.46 (d, J=1.83 Hz, 1H), 7.29-7.43 (m, 4H), 7.09 (d, J=1.71 Hz, 1H), 6.90-7.04 (m, J=2.44 Hz, 1H), 4.58-4.69 (m, 1H), 3.75-3.91 (m, 4H), 3.66 (dd, J=4.21, 14.22 Hz, 2H), 2.72-2.85 (m, J=8.06, 8.06 Hz, 1H), 2.58-2.68 (m, J=1.83 Hz, 2H), 2.39-2.17 (m, 10H), 2.10 (s, 3H), 1.68 (m, 1H), 1.49-1.35 (m, 4H), 1.28-1.20 (m, 1H), 1.09-0.75 (m, 5H).

LCMS (HPLC Method 2): m/z 496 [M+H]+ @ r.t. 4.85 min.

HRMS (ESI) calcd for $C_{28}H_{39}FN_5O_2$ [M+H]+ 496.3083 found 496.3092.

N-[(1S)-1-cyclohexyl-2-(4-methylpiperazin-1-yl)ethyl]-2-[(4S)-7-(3-fluorophenyl)-1-oxo-1,2,3,4-tetrahydropyrrolo[1,2-a]pyrazin-4-yl]acetamide trifluoroacetate [(I) R2=3-fluorophenyl, R3=R4=H, R1=—NH—R5, R5=-(1S)-1-cyclohexyl-2-(4-methylpiperazin-1-yl)ethyl](cpd 4)

$^1$H NMR (400 MHz, DMSO-d6) δ 7.59-7.85 (m, 2H), 7.24-7.43 (m, 4H), 7.11 (d, J=1.83 Hz, 1H), 6.88-7.02 (m, 1H), 4.60-4.76 (m, J=1.10 Hz, 1H), 3.80-3.90 (m, 2H), 3.69-3.77 (m, J=17.21 Hz, 1H), 3.32-3.41 (m, J=3.84, 12.76 Hz, 1H), 2.78-2.84 (m, 1H), 2.76 (s, 3H), 2.59 (dd, J=5.80, 14.71 Hz, 2H), 1.35-1.55 (m, J=12.57, 12.57 Hz, 5H), 1.24 (br. s., 1H), 0.89-1.04 (m, J=11.35 Hz, 2H), 0.71-0.89 (m, 3H).

LCMS (HPLC Method 2): m/z 496 [M+H]+ @ r.t. 4.95 min.

HRMS (ESI) calcd for $C_{28}H_{39}FN_5O_2$ [M+H]+ 496.3083 found 496.3085.

N-{(1S)-1-cyclohexyl-2-[4-(dimethylamino)piperidin-1-yl]ethyl}-2-[(4R)-7-(3,4-difluorophenyl)-1-oxo-1,2,3,4-tetrahydropyrrolo[1,2-a]pyrazin-4-yl]acetamide [(I) R2=3,4-difluorophenyl, R3=R4=H, R1=—NH—R5, R5=-(1S)-1-cyclohexyl-2-[4-(dimethylamino)piperidin-1-yl](cpd 5)

$^1$H NMR (400 MHz, DMSO-d6) δ 7.73 (d, J=2.20 Hz, 1H), 7.67 (d, J=9.15 Hz, 1H), 7.55-7.66 (m, 1H), 7.42 (d, J=1.83 Hz, 1H), 7.33-7.41 (m, 2H), 7.08 (d, J=1.83 Hz, 1H), 4.58-4.73 (m, 1H), 3.73-3.91 (m, J=5.86 Hz, 1H), 3.59-3.73 (m, J=1.59 Hz, 1H), 2.76 (dd, J=7.38, 14.59 Hz, 2H), 2.60 (dd, J=6.41, 14.46 Hz, 1H), 2.24 (br. s., 8H), 2.02-2.12 (m, 3H), 1.48-1.70 (m, J=6.71 Hz, 8H), 1.30-1.43 (m, 1H), 0.80-1.30 (m, 8H).

LCMS (HPLC Method 2): m/z 542 [M+H]+ @ r.t. 5.07 min.

HRMS (ESI) calcd for $C_{30}H_{42}F_2N_5O_2$ [M+H]+ 542.3301 found 542.3307.

N-{(1S)-1-cyclohexyl-2-[4-(dimethylamino)piperidin-1-yl]ethyl}-2-[(4S)-7-(3,4-difluorophenyl)-1-oxo-1,2,3,4-tetrahydropyrrolo[1,2-a]pyrazin-4-yl]acetamide [(I) R2=3,4-difluorophenyl, R3=R4=H, R1=—NH—R5, R5=-(1S)-1-cyclohexyl-2-[4-(dimethylamino)piperidin-1-yl](cpd 6)

$^1$H NMR (400 MHz, DMSO-d6) δ 7.71 (d, J=3.17 Hz, 1H), 7.54-7.66 (m, J=9.89 Hz, 2H), 7.29-7.43 (m, 3H), 7.09 (d, J=1.71 Hz, 1H), 4.60-4.72 (m, 1H), 3.75-3.84 (m, 1H), 3.70 (dd, J=4.39, 13.06 Hz, 1H), 3.35-3.43 (m, J=3.78 Hz, 1H), 2.86-2.95 (m, J=11.35 Hz, 0H), 2.70-2.84 (m, 2H), 2.57 (dd, J=6.23, 14.89 Hz, 1H), 2.09-2.42 (m, 9H), 1.85-1.98 (m, J=3.78 Hz, 1H), 1.81 (t, J=10.74 Hz, 1H), 1.66-1.76 (m, J=6.47 Hz, 2H), 1.16-1.54 (m, 8H), 0.89-1.06 (m, J=4.27 Hz, 2H), 0.69-0.88 (m, J=12.57 Hz, 3H).

LCMS (HPLC Method 2): m/z 542 [M+H]+ @ r.t. 5.22 min.

HRMS (ESI) calcd for $C_{30}H_{42}F_2N_5O_2$ [M+H]+ 542.3301 found 542.3309.

N-[(1S)-1-cyclohexyl-2-(4-methylpiperazin-1-yl)ethyl]-2-[(4R)-7-(3,4-difluorophenyl)-1-oxo-1,2,3,4-tetrahydropyrrolo[1,2-a]pyrazin-4-yl]acetamide [(I) R2=3,4-difluorophenyl, R3=R4=H, R1=—NH—R5, R5=-(1S)-1-cyclohexyl-2-(4-methylpiperazin-1-yl)](cpd 7)

$^1$H NMR (400 MHz, DMSO-d6) δ 7.70 (br. s., 1H), 7.57-7.67 (m, 2H), 7.30-7.40 (m, 3H), 7.05 (d, J=1.71 Hz, 1H), 4.61 (td, J=3.67, 6.83 Hz, 1H), 3.77-3.83 (m, 1H), 3.60-3.66 (m, 1H), 3.36 (m, 2H), 2.70-2.76 (m, 1H), 2.56-2.63 (m, 1H), 2.0.5-2.28 (m, 9H), 1.50-1.66 (m, 7H), 1.32 (m, 1H), 0.89-1.25 (m, 6H).

LCMS (HPLC Method 2): m/z 514 [M+H]+ @ r.t. 5.0 min.

HRMS (ESI) calcd for $C_{28}H_{38}F_2N_5O_2$ [M+H]$^+$ 514.2988 found 514.2985.

N-[(1S)-1-cyclohexyl-2-(4-methylpiperazin-1-yl)ethyl]-2-[(4S)-7-(3,4-difluorophenyl)-1-oxo-1,2,3,4-tetrahydropyrrolo[1,2-a]pyrazin-4-yl]acetamide [(I) R2=3,4-difluorophenyl, R3=R4=H, R1=—NH—R5, R5=-(1S)-1-cyclohexyl-2-(4-methylpiperazin-1-yl)(cpd 8)

$^1$H NMR (400 MHz, DMSO-d6) δ 7.73 (br. s., 1H), 7.57-7.67 (m, 2H), 7.31-7.41 (m, 3H), 7.09 (d, J=1.71 Hz, 1H), 4.65 (td, J=3.66, 6.84 Hz, 1H), 3.76-3.86 (m, 1H), 3.65-3.74 (m, 1H), 3.40 (m, 2H), 2.77 (m, 1H), 2.58 (m, 1H), 2.45-2.28 (m, 11H), 1.42 (m, 4H), 1.24 (m, 1H), 0.97 (m, 1H), 0.81 (m, 4H).

LCMS (HPLC Method 2): m/z 514 [M+H]$^+$ @ r.t. 5.09 min.

HRMS (ESI) calcd for $C_{28}H_3F_2N_5O_2$ [M+H]$^+$ 514.2988 found 514.2989.

N-{(1S)-1-cyclohexyl-2-[4-(dimethylamino)piperidin-1-yl]ethyl}-2-[(4R)-7-(2-fluoropyridin-4-yl)-1-oxo-1,2,3,4-tetrahydropyrrolo[1,2-a]pyrazin-4-yl]acetamide [(I) R2=2-fluoropyridin-4-yl, R3=R4=H, R1=—NH—R5, R5=-(1S)-1-cyclohexyl-2-(4-(dimethylamino)piperidin-1-yl)](cpd 9)

$^1$H NMR (400 MHz, DMSO-d6) δ 8.13 (d, J=5.37 Hz, 1H), 7.84 (br. s., 1H), 7.67-7.80 (m, 2H), 7.54 (d, J=5.25 Hz, 1H), 7.37 (s, 1H), 7.30 (d, J=1.71 Hz, 1H), 4.62-4.75 (m, 1H), 4.00-4.15 (m, J=5.00 Hz, 1H), 3.80 (br. s., 1H), 3.61-3.74 (m, J=5.13 Hz, 1H), 3.41 (m, 2H), 2.85-2.60 (m, 7H), 2.62 (s, 6H), 2.26 (m, 4H), 1.84-0.93 (m, 11H).

LCMS (HPLC Method 2): m/z 525 [M+H]$^+$ @ r.t. 4.37 min.

HRMS (ESI) calcd for $C_{29}H_{42}FN_5O_2$ [M+H]$^+$ 525.3348 found 525.3333.

N-{(1S)-1-cyclohexyl-2-[4-(dimethylamino)piperidin-1-yl]ethyl}-2-[(4S)-7-(2-fluoropyridin-4-yl)-1-oxo-1,2,3,4-tetrahydropyrrolo[1,2-a]pyrazin-4-yl]acetamide [(I) R2=2-fluoropyridin-4-yl, R3=R4=H, R1=—NH—R5, R5=-(1S)-1-cyclohexyl-2-(4-(dimethylamino)piperidin-1-yl)](cpd 10)

$^1$H NMR (400 MHz, DMSO-d6) δ 8.07 (d, J=5.37 Hz, 1H), 7.78 (d, J=3.42 Hz, 1H), 7.59 (d, J=1.83 Hz, 1H), 7.57 (d, J=9.15 Hz, 1H), 7.49 (dd, J=1.77, 5.31 Hz, 1H), 7.30 (s, 1H), 7.26 (d, J=1.83 Hz, 1H), 4.59-4.72 (m, 1H), 3.72-3.83 (m, 1H), 3.69 (dd, J=4.39, 12.33 Hz, 1H), 3.33-3.42 (m, 1H), 2.83 (d, J=10.13 Hz, 1H), 2.67-2.79 (m, 2H), 2.55 (dd, J=5.61, 14.65 Hz, 1H), 2.12-2.23 (m, 2H), 2.10 (s, 6H), 1.89-1.97 (m, 1H), 1.81-1.89 (m, 1H), 1.69-1.79 (m, 1H), 1.61 (d, J=10.62 Hz, 2H), 1.11-1.48 (m, 7H), 0.62-1.00 (m, 1H).

LCMS (HPLC Method 2): m/z 525 [M+H]$^+$ @ r.t. 4.37 min.

HRMS (ESI) calcd for $C_{29}H_{42}FN_6O_2$ [M+H]$^+$ 525.3348 found 525.3340.

N-[(1S)-1-cyclohexyl-2-(4-methylpiperazin-1-yl)ethyl]-2-[(4R)-7-(2-fluoropyridin-4-yl)-1-oxo-1,2,3,4-tetrahydropyrrolo[1,2-a]pyrazin-4-yl]acetamide [(I) R2=2-fluoropyridin-4-yl, R3=R4=H, R1=—NH—R5, R5=-(1S)-1-cyclohexyl-2-(4-methylpiperazin-1-yl)(cpd 11)

$^1$H NMR (400 MHz, DMSO-d6) δ 8.11 (d, J=5.25 Hz, 1H), 7.83 (br. s., 1H), 7.71 (d, J=1.71 Hz, 1H), 7.68 (d, J=9.15 Hz, 1H), 7.53 (td, J=1.65, 3.54 Hz, 1H), 7.34 (s, 1H), 7.28 (d, J=1.71 Hz, 1H), 4.64-4.73 (m, 1H), 3.76-3.88 (m, 1H), 3.68 (dd, J=3.54, 12.45 Hz, 1H), 2.78 (dd, J=7.63, 15.07 Hz, 1H), 2.66 (m, 1H), 2.18 (m, 13H), 1.64 (m, 4H), 1.35 (m, 1H), 1.12 (m, 4H), 0.95 (m, 2H).

LCMS (HPLC Method 2): m/z 497 [M+H]$^+$ @ r.t. 4.29 min.

HRMS (ESI) calcd for $C_{27}H_{38}FN_6O_2$ [M+H]$^+$ 497.3035 found 497.3029.

N-[(1S)-1-cyclohexyl-2-(4-methylpiperazin-1-yl)ethyl]-2-[(4S)-7-(2-fluoropyridin-4-yl)-1-oxo-1,2,3,4-tetrahydropyrrolo[1,2-a]pyrazin-4-yl]acetamide [(I) R2=2-fluoropyridin-4-yl, R3=R4=H, R1=—NH—R5, R5=-(1S)-1-cyclohexyl-2-(4-methylpiperazin-1-yl)(cpd 12)

$^1$H NMR (400 MHz, DMSO-d6) δ 9.53 (br. s., 1H), 8.10 (d, J=5.37 Hz, 1H), 7.84 (d, J=3.42 Hz, 1H), 7.67 (d, J=9.03 Hz, 1H), 7.63 (s, 1H), 7.52 (d, J=5.25 Hz, 1H), 7.34 (s, 1H), 7.30 (d, J=1.71 Hz, 1H), 4.67-4.75 (m, 1H), 3.64-3.84 (m, 2H), 3.39 (m, 2H), 2.82-2.66 (m, 7H), 2.36-2.25 (m, 8H), 1.49-1.35 (m, 4H), 1.24 (m, 1H), 0.99-0.87 (m, 2H), 0.85-0.70 (m, 5H).

LCMS (HPLC Method 2): m/z 497 [M+H]$^+$ @ r.t. 4.24 min.

HRMS (ESI) calcd for $C_2H_{38}FN_6O_2$ [M+H]$^+$ 497.3035 found 497.302.

N-[(1S)-1-cyclohexyl-2-(4-methylpiperazin-1-yl)ethyl]-2-[(4R)-7-(3-hydroxyphenyl)-1-oxo-1,2,3,4-tetrahydropyrrolo[1,2-a]pyrazin-4-yl]acetamide [(I) R2=3-hydroxyphenyl, R3=R4=H, R1=—NH—R5, R5=-(1S)-1-cyclohexyl-2-(4-methylpiperazin-1-yl)(cpd 13)

$^1$H NMR (400 MHz, DMSO-d6) δ 9.27 (br. s., 1H), 7.68 (d, J=2.69 Hz, 1H), 7.62 (d, J=9.28 Hz, 1H), 7.23 (d, J=1.71 Hz, 1H), 7.03-7.15 (m, 1H), 6.82-7.01 (m, 3H), 6.56 (dd, J=2.26, 7.75 Hz, 1H), 4.57-4.71 (m, 1H), 3.74-3.88 (m, 1H), 3.68 (dd, J=4.27, 12.45 Hz, 1H), 2.74 (dd, J=8.18, 14.40 Hz, 1H), 2.56 (dd, J=8.18, 14.40 Hz, 1H), 2.37-2.18 (m, 10H), 2.11 (s, 3H) 1.47 (m, 4H), 1.26 (m, 1H), 1.01-0.80 (m, 5H).

LCMS (HPLC Method 2): m/z 494 [M+H]$^+$ @ r.t. 4.23 min.

HRMS (ESI) calcd for $C_2H_{40}N_5O_3$ [M+H]$^+$ 494.3126 found 494.3108.

N-{(1S)-1-cyclohexyl-2-[4-(dimethylamino)piperidin-1-yl]ethyl}-2-[7-(3-hydroxyphenyl)-1-oxo-1,2,3,4-tetrahydropyrrolo[1,2-a]pyrazin-4-yl]acetamide [(I) R2=3-hydroxyphenyl, R3=R4=H, R1=—NH—R5, R5=-(1S)-1-cyclohexyl-2-(4-methylpiperazin-1-yl)(cpd 14)

LCMS (HPLC Method 2): m/z 522 [M+H]$^+$ @ r.t. 4.27 min.

HRMS (ESI) calcd for $C_{30}H_{44}N_5O_3$ [M+H]$^+$ 522.34396 found 522.3428.

N-{(1S)-1-cyclohexyl-2-[4-(dimethylamino)piperidin-1-yl]ethyl}-2-{(4R)-1-oxo-7-[3-(trifluoromethyl)phenyl]-1,2,3,4-tetrahydropyrrolo[1,2-a]pyrazin-4-yl}acetamide [(I) R2=3-(trifluoromethyl)phenyl, R3=R4=H, R1=—NH—R5, R5=-(1S)-1-cyclohexyl-2-[4-(dimethylamino)piperidin-1-yl]](cpd 15)

$^1$H NMR (400 MHz, DMSO-d6) δ 7.84-7.91 (m, 2H), 7.76 (br. s., 1H), 7.69 (d, J=9.15 Hz, 1H), 7.53-7.60 (m, 2H), 7.48-7.51 (m, 1H), 7.16 (d, J=1.83 Hz, 1H), 4.64 (t, J=4.33 Hz, 1H), 3.79 (br. s., 1H), 3.63-3.71 (m, 1H), 3.37-3.43 (m, 2H), 2.73-2.85 (m, 4H), 2.58-2.66 (m, 1H), 2.33 (dd, J=1.77, 3.60 Hz, 6H), 2.22 (d, J=10.01 Hz, 1H), 2.04-2.13 (m, 1H), 1.65-1.73 (m, 8H), 1.35-0.93 (m, 8H)

LCMS (HPLC Method 2): m/z 574 [M+H]$^+$ @ r.t. 5.41 min.

HRMS (ESI) calcd for $C_{31}H_{43}F_3N_5O_2$ [M+H]$^+$ 574.3364 found 574.3344.

N-{(1S)-1-cyclohexyl-2-[4-(dimethylamino)piperidin-1-yl]ethyl}-2-{(4S)-1-oxo-7-[3-(trifluoromethyl)phenyl]-1,2,3,4-tetrahydropyrrolo[1,2-a]pyrazin-4-yl}acetamide [(I) R2=3-(trifluoromethyl)phenyl, R3=R4=H, R1=—NH—R5, R5=-(1S)-1-cyclohexyl-2-[4-(dimethylamino)piperidin-1-yl]](cpd 16)

¹H NMR (400 MHz, DMSO-d6) δ 7.82-7.88 (m, 2H), 7.74 (d, J=3.05 Hz, 1H), 7.60 (d, J=9.40 Hz, 1H), 7.51-7.57 (m, 1H), 7.45-7.50 (m, 2H), 7.16 (d, J=1.83 Hz, 1H), 4.68 (dd, J=4.70, 8.61 Hz, 1H), 3.75-3.83 (m, 1H), 3.71 (dd, J=4.33, 12.02 Hz, 1H), 3.35-3.45 (m, 2H), 2.86 (d, J=9.76 Hz, 1H), 2.71-2.81 (m, 2H), 2.57 (dd, J=5.55, 14.59 Hz, 1H); 2.16-2.27 (m, 2H), 2.10-2.16 (m, 6H), 1.96 (br. s., 1H), 1.72-1.90 (m, 2H), 1.65 (m, 2H), 1.20-1.47 (m, 8H), 0.75-0.93 (m, 4H).

LCMS (HPLC Method 2): m/z 574 [M+H]⁺ @ r.t. 5.55 min.

HRMS (ESI) calcd for $C_{31}H_{43}F_3N_5O_2$ [M+H]⁺ 574.3364 found 574.3343.

N-[(1S)-1-cyclohexyl-2-(4-methylpiperazin-1-yl)ethyl]-2-{(4R)-1-oxo-7-[3-(trifluoromethyl)phenyl]-1,2,3,4-tetrahydropyrrolo[1,2-a]pyrazin-4-yl}acetamide [(I) R2=3-(trifluoromethyl)phenyl, R3=R4=H, R1=—NH—R5, R5=-(1S)-1-cyclohexyl-2-(4-methylpiperazin-1-yl)ethyl] (cpd 17)

¹H NMR (400 MHz, DMSO-d6) δ 7.87 (br. s., 2H), 7.76 (br. s., 1H), 7.70 (d, J=9.15 Hz, 1H), 7.53-7.59 (m, 2H), 7.46-7.51 (m, 1H), 7.16 (d, J=1.71 Hz, 1H), 4.60-4.70 (m, 1H), 3.75-3.86 (m, 1H), 3.64-3.72 (m, 1H), 3.39 (bin, 2H), 2.79 (dd, J=7.08, 14.77 Hz, 1H), 2.62-2.68 (m, 1H), 2.07-2.34 (m, 11H), 1.56-1.65 (m, 8H), 0.92-1.24 (m, 6H).

LCMS (HPLC Method 2): m/z 546 [M+H]⁺ @ r.t. 5.32 min.

HRMS (ESI) calcd for $C_2H_{39}F_3N_5O_2$ [M+H]⁺ 546.3051 found 546.3034.

N-[(1S)-1-cyclohexyl-2-(4-methylpiperazin-1-yl)ethyl]-2-{(4S)-1-oxo-7-[3-(trifluoromethyl)phenyl]-1,2,3,4-tetrahydropyrrolo[1,2-a]pyrazin-4-yl}acetamide hydrochloride [(I) R2=3-(trifluoromethyl)phenyl, R3=R4=H, R1=—NH—R5, R5=-(1S)-1-cyclohexyl-2-(4-methylpiperazin-1-yl)ethyl](cpd 18)

¹H NMR (400 MHz, DMSO-d6) δ 9.27 (br. s., 1H), 7.83-7.88 (m, 2H), 7.76 (d, J=3.78 Hz, 1H), 7.66 (d, J=9.15 Hz, 1H), 7.51-7.58 (m, 1H), 7.44-7.51 (m, 2H), 7.18 (d, J=1.71 Hz, 1H), 4.65-4.75 (m, 1H), 3.80 (d, J=9.28 Hz, 1H), 3.74 (dd, J=4.09, 12.76 Hz, 1H), 3.39 (bm, 2H), 2.73-2.80 (m, 3H), 2.18-2.34 (m, 8H), 1.24-1.48 (m, 6H), 0.75-0.97 (m, 4H).

LCMS (HPLC Method 2): m/z 546 [M+H]⁺ @ r.t. 5.41 min.

HRMS (ESI) calcd for $C_{29}H_{39}F_3N_5O_2$ [M+H]⁺ 546.3051 found 546.3051.

N-[(1S)-1-cyclohexyl-2-(4-methylpiperazin-1-yl)ethyl]-2-[(4S)-1-oxo-7-(1H-pyrazol-4-yl)-1,2,3,4-tetrahydropyrrolo[1,2-a]pyrazin-4-yl]acetamide [(I) R2=1H-pyrazol-4-yl, R3=R4=H, R1=—NH—R5, R5=-(1S)-1-cyclohexyl-2-(4-methylpiperazin-1-yl)ethyl](cpd 19)

¹H NMR (400 MHz, DMSO-d6) δ 8.01 (d, J=1.59 Hz, 1H), 7.74 (d, J=8.79 Hz, 2H), 7.12 (d, J=1.71 Hz, 1H), 6.82 (d, J=1.83 Hz, 1H), 4.58 (m, 1H), 3-77-3.90 (m, 2H), 3.62-3.67 (m, 1H), 3.53 (m, 1H), 2.66-2.74 (m, 1H), 2.21-2.44 (m, 8H), 1.58-1.68 (m, 6H), 1.33-1.40 (m, 2H), 1.07-1.24 (m, 4H), 0.95-1.01 (m, 2H).

LCMS (HPLC Method 2): m/z 468 [M+H]⁺ @ r.t. 3.78 min.

HRMS (ESI) calcd for $C_{25}H_{38}N_7O_2$ [M+H]⁺ 468.3082 found 468.3068.

2-[(4R)-7-(3-chlorophenyl)-1-oxo-1,2,3,4-tetrahydropyrrolo[1,2-a]pyrazin-4-yl]-N-[(2S)-3,3-dimethyl-1-(4-methylpiperazin-1-yl)butan-2-yl]acetamide [(I) R2=3-chlorophenyl, R3=R4=H, R1=—NH—R5, R5=-(2S)-3,3-dimethyl-1-(4-methylpiperazin-1-yl)butan-2-yl](cpd 20)

¹H NMR (400 MHz, DMSO-d6) δ 7.75 (br. s., 1H), 7.69 (d, J=9.64 Hz, 1H), 7.62 (t, J=1.65 Hz, 1H), 7.50-7.57 (m, 2H), 7.31-7.37 (m, 1H), 7.19 (dd, J=1.34, 7.81 Hz, 1H), 7.09 (d, J=1.71 Hz, 1H), 4.57-4.70 (m, 1H), 3.77 (dt, J=2.81, 9.83 Hz, 1H), 3.58-3.69 (m, J=3.72, 12.02 Hz, 1H), 3.38 (bm, 2H), 2.81 (dd, J=6.84, 15.14 Hz, 1H), 2.61-2.70 (m, 1H), 2.13-2.33 (m, 10H), 1.99 (br. s., 3H), 0.84 (s, 9H)

LCMS (HPLC Method 2): m/z 486 [M+H]⁺ @ r.t. 4.6 min.

HRMS (ESI) calcd for $C_{26}H_{37}ClN_5O_2$ [M+H]⁺ 486.2631 found 486.2617.

2-[(4S)-7-(3-chlorophenyl)-1-oxo-1,2,3,4-tetrahydropyrrolo[1,2-a]pyrazin-4-yl]-N-[(2S)-3,3-dimethyl-1-(4-methylpiperazin-1-yl)butan-2-yl]acetamide hydrochloride [(I) R2=3-chlorophenyl, R3=R4=H, R1=—NH—R5, R5=-(2S)-3,3-dimethyl-1-(4-methylpiperazin-1-yl)butan-2-yl] (cpd 21)

¹H NMR (400 MHz, DMSO-d6) δ 9.36 (br. s., 1H), 7.79 (br. s., 1H), 7.70 (d, J=9.76 Hz, 1H), 7.59 (t, J=1.77 Hz, 1H), 7.47-7.53 (m, 2H), 7.34 (t, J=7.93 Hz, 1H), 7.16-7.23 (m, 1H), 7.05-7.13 (m, 1H), 4.56-4.77 (m, 1H), 3.65-3.85 (m, 2H), 3.39 (bm, 2H), 3.04 (m, 1H), 2.81 (m, 1H), 2.77 (s, 3H), 2.67 (m, 1H), 2.46 (m, 1H), 2.15-2.36 (m, 8H), 0.79 (s, 9H).

LCMS (HPLC Method 2): m/z 486 [M+H]⁺ @ r.t. 4.89 min.

HRMS-(ESI) calcd for $C_{26}H_{37}ClN_5O_2$ [M+H]⁺ 486.2631 found 486.2624.

2-[(4R)-7-(3-chlorophenyl)-1-oxo-1,2,3,4-tetrahydropyrrolo[1,2-a]pyrazin-4-yl]-N-{(1S)-1-cyclohexyl-2-[4-(dimethylamino)piperidin-1-yl]ethyl}acetamide [(I) R2=3-chlorophenyl, R3=R4=H, R1=—NH—R5, R5=-(1S)-1-cyclohexyl-2-[4-(dimethylamino)piperidin-1-yl] (cpd 22)

¹H NMR (400 MHz, DMSO-d6) δ 7.73 (d, J=2.20 Hz, 1H), 7.66 (d, J=9.03 Hz, 1H), 7.59 (t, J=1.83 Hz, 1H), 7.52 (d, J=7.93 Hz, 1H), 7.44 (d, J=1.71 Hz, 1H), 7.34 (t, J=7.93 Hz, 1H), 7.19 (dd, J=1.65, 7.63 Hz, 1H), 7.08 (d, J=1.83 Hz, 1H), 4.56-4.75 (m, 1H), 3.79 (td, J=6.91, 13.88 Hz, 1H), 3.62-3.73 (m, 1H), 2.74-2.85 (m, 1H), 2.68-2.74 (m, 1H), 2.59 (dd, J=6.16, 14.59 Hz, 1H), 2.17 (dd, J=6.41, 12.51 Hz, 1H), 1.95-2.09 (m, 7H), 1.81 (tt, J=3.65, 11.12 Hz, 1H), 1.44-1.72 (m, 10H), 1.29-1.44 (m, 1H), 0.71-1.27 (m, 8H).

LCMS (HPLC Method 2): m/z 540 [M+H]⁺ @ r.t. 5.38 min.

HRMS (ESI) calcd for $C_{30}H_{43}ClN_5O_2$ [M+H]⁺ 540.31 found 540.3102.

2-[(4S)-7-(3-chlorophenyl)-1-oxo-1,2,3,4-tetrahydropyrrolo[1,2-a]pyrazin-4-yl]-N-{(1S)-1-cyclohexyl-2-[4-(dimethylamino)piperidin-1-yl]ethyl}acetamide [(I) R2=3-chlorophenyl, R3=R4=H, R1=—NH—R5, R5=-(1S)-1-cyclohexyl-2-[4-(dimethylamino)piperidin-1-yl](cpd 23)

¹H NMR (400 MHz, DMSO-d6) δ 7.72 (d, J=2.81 Hz, 1H), 7.61 (d, J=9.40 Hz, 1H), 7.58 (t, J=1.89 Hz, 1H), 7.47-7.54 (m, 1H), 7.39 (d, J=1.83 Hz, 1H), 7.33 (t, J=7.87 Hz, 1H), 7.18 (ddd, J=0.92, 1.98, 7.96 Hz, 1H), 7.09 (d, J=1.83 Hz, 1H), 4.56-4.77 (m, J=7.20 Hz, 1H), 3.74-3.89 (m, 1H), 3.62-3.73 (m, J=1.59, 4.03 Hz, 1H), 2.80-2.92 (m, J=9.76 Hz, 1H), 2.70-2.80 (m, 2H), 2.54-2.60 (m, 1H), 2.16-2.27 (m, 2H), 2.12 (s, 6H), 1.83-1.98 (m, 2H), 1.72-1.81 (m, 1H), 1.56-1.68 (m, J=11.47 Hz, 2H), 1.35-1.53 (m, 4H), 1.15-1.34 (m, 4H), 0.88-1.08 (m, 2H), 0.67-0.90 (m, J=9.89 Hz, 3H).

LCMS (HPLC Method 2): m/z 540 [M+H]⁺ @ r.t. 6.02 min.

HRMS (ESI) calcd for $C_{30}H_{43}ClN_5O_2$ [M+H]⁺ 540.31 found 540.3111.

2-[(4R)-7-(3-chlorophenyl)-1-oxo-1,2,3,4-tetrahydropyrrolo[1,2-a]pyrazin-4-yl]-N-[(2S)-1-(4-methylpiperazin-1-yl)propan-2-yl]acetamide [(I) R2=3-chlorophenyl, R3=R4=H, R1=—NH—R5, R5=-(2S)-1-(4-methylpiperazin-1-yl)propan-2-yl](cpd 24)

$^1$H NMR (400 MHz, DMSO-d6) δ 7.82 (d, J=7.69 Hz, 1H), 7.70 (d, J=3.05 Hz, 1H), 7.60 (s, 1H), 7.52 (d, J=8.30 Hz, 1H), 7.42 (s, 1H), 7.34 (t, J=7.87 Hz, 1H), 7.20 (d, J=8.18 Hz, 1H), 7.09 (d, J=1.34 Hz, 1H), 4.57-4.75 (m, 1H), 3.84-3.97 (m, 1H), 3.68 (dd, J=3.60, 12.88 Hz, 1H), 3.39 (m, 2H), 2.65-2.74 (m, 1H), 2.52-2.59 (m, 2H), 2.02-2.33 (m, 11H) 1.00 (d, J=6.47 Hz, 3H).

LCMS (HPLC Method 2): m/z 444 [M+H]$^+$ @ r.t. 4.11 min.

HRMS (ESI) calcd for $C_{23}H_{31}ClN_5O_2$ [M+H]$^+$ 444.2161 found 444.2151.

2-[(4S)-7-(3-chlorophenyl)-1-oxo-1,2,3,4-tetrahydropyrrolo[1,2-a]pyrazin-4-yl]-N-[(2S)-1-(4-methylpiperazin-1-yl)propan-2-yl]acetamide hydrochloride [(I) R2=3-chlorophenyl, R3=R4=H, R1=—NH—R5, R5=-(2S)-1-(4-methylpiperazin-1-yl)propan-2-yl](cpd 25)

$^1$H NMR (400 MHz, DMSO-d6) δ 9.53 (br. s., 1H), 7.88 (d, J=8.54 Hz, 1H), 7.74 (d, J=2.69 Hz, 1H), 7.61 (t, J=1.71 Hz, 1H), 7.52 (d, J=7.69 Hz, 1H), 7.47-7.50 (m, 1H), 7.35 (t, J=7.87 Hz, 1H), 7.20 (dd, J=1.10, 7.93 Hz, 1H), 4.57-4.68 (m, 1H), 3.87-4.00 (m, 1H), 3.70 (dd, J=3.60, 12.39 Hz, 1H), 2.80-3.07 (m, 5H), 2.75 (br. s., 3H), 2.62-2.70 (m, 1H), 2.53-2.61 (m, 1H), 2.13-2.35 (m, 5H), 0.95 (d, J=6.59 Hz, 3H).

LCMS (HPLC Method 2): m/z 444 [M+H]$^+$ @ r.t. 4.38 min.

HRMS (ESI) calcd for $C_{23}H_{31}ClN_5O_2$ [M+H]$^+$ 444.2161 found 444.2152.

2-[(4S)-7-(5-chloro-2-fluorophenyl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide [(I) R2=5-chloro-2-fluorophenyl, R3=R4=H, R1=—NH—R5, R5=(1S)-1-cyclohexyl-2-(4-methylpiperazin-1-yl)ethyl](cpd 26)

$^1$H NMR (400 MHz, DMSO-d6) δ 7.79 (d, J=4.03 Hz, 1H), 7.72-7.77 (m, 0.1H), 7.57-7.68 (m, 1H), 7.38 (s, 1H), 7.22-7.29 (m, 2H), 7.16 (s, 1H), 4.65-4.79 (m, J=3.42 Hz, 1H), 3.75 (dd, J=4.09, 12.88 Hz, 2H), 3.38 (m, 1H), 2.75-2.83 (m, J=8.91 Hz, 1H), 2.74 (br. s., 4H), 2.53-2.59 (m, J=4.76 Hz, 1H), 2.15-2.40 (m, 4H), 1.10-1.56 (m, 8H), 0.64-1.01 (m, 6H)

LCMS (HPLC Method 2): m/z 530 [M+H]$^+$ @ r.t. 5.17 min.

HRMS (ESI) calcd for $C_{28}H_3ClFN_5O_2$ [M+H]$^+$ 530.2693 found 530.2704.

2-[(4R)-7-(5-chloro-2-fluorophenyl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide [(I) R2=5-chloro-2-fluorophenyl, R3=R4=H, R1=—NH—R5, R5=(1S)-1-cyclohexyl-2-(4-methylpiperazin-1-yl)ethyl](cpd 27)

$^1$H NMR (400 MHz, DMSO-d6) δ 7.77 (dt, J=2.62, 6.62 Hz, 2H), 7.66 (d, J=9.28 Hz, 1H), 7.41-7.47 (m, 1H), 7.18-7.30 (m, 2H), 7.14 (s, 1H), 4.62-4.78 (m, 1H), 3.81 (td, J=7.08, 13.91 Hz, 1H), 3.69 (dd, J=3.60, 12.76 Hz, 1H), 3.35-3.42 (m, 2H), 2.77 (dd, J=8.06, 15.01 Hz, 1H), 2.62 (dd, J=5.74, 15.01 Hz, 1H), 2.01-2.31 (m, 10H), 1.98 (s, 3H), 1.50-1.73 (m, 6H), 1.28-1.42 (m, 1H), 0.80-1.20 (m, 6H)

LCMS (HPLC Method 2): m/z 530 [M+H]$^+$ @ r.t. 5.02 min.

HRMS (ESI) calcd for $C_{28}H_{38}ClFN_5O_2$ [M+H]$^+$ 530.2693 found 530.2709.

2-[(4R)-7-(3-chloro-4-hydroxyphenyl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide dihydrobromide [(I) R2=3-chloro-4-hydroxyphenyl, R3=R4=H, R1=—NH—R5, R5=(1S)-1-cyclohexyl-2-(4-methylpiperazin-1-yl)ethyl](cpd 28)

$^1$H NMR (400 MHz, DMSO-d6) δ 9.96 (br. s., 1H), 7.60-7.78 (m, 2H), 7.49 (d, J=2.20 Hz, 1H), 7.26-7.35 (m, 2H), 6.86-6.99 (m, 2H), 4.55-4.67 (m, 1H), 3.76-3.89 (m, 1H), 3.64 (dd, J=3.42, 11.96 Hz, 1H), 2.70-2.79 (m, 1H), 2.57-2.65 (m, 1H), 2.12-2.33 (m, 13H), 1.50-1.71 (m, 5H), 1.29-1.43 (m, 1H), 0.83-1.26 (m, 5H).

LCMS (HPLC Method 2): m/z 528 [M+H]$^+$ @ r.t. 4.34 min.

HRMS (ESI) calcd for $C_{28}H_{39}ClN_5O_3$ [M+H]$^+$ 528.2736 found 528.2719.

2-[(4S)-7-(3-chloro-4-hydroxyphenyl)-1-oxo-1,2,3,4-tetrahydropyrrolo[2-a]pyrazin-4-yl]-N-[(1S)-1-cyclohexyl-2-(4-methylpiperazin-1-yl)ethyl]acetamide dihydrobromide [(I) R2=3-chloro-4-hydroxyphenyl, R3=R4=H, R1=—NH—R5, R5=(1S)-1-cyclohexyl-2-(4-methylpiperazin-1-yl)ethyl](cpd 29)

LCMS (HPLC Method 2): m/z 528 [M+H]$^+$ @ r.t. 4.26 min.

HRMS (ESI) calcd for $C_{28}H_{39}ClN_5O_3$ [M+H]$^+$ 528.2736 found 528.27159.

2-[(4S)-6-bromo-7-(3-chloro-4-hydroxyphenyl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide dihydrobromide [(I) R2=3-chloro-4-hydroxyphenyl, R3=Br, R4=H, R1=—NH—R5, R5=(1S)-1-cyclohexyl-2-(4-methylpiperazin-1-yl)ethyl](cpd 30)

$^1$H NMR (400 MHz, DMSO-d6) δ 7.63-7.71 (m, 2H), 7.28 (d, J=1.71 Hz, 1H), 7.15-7.47 (m, 2H), 7.03 (d, J=8.42 Hz, 1H), 6.74 (s, 1H), 6.46 (d; J=5.37 Hz, 1H), 4.61-4.70 (m, 1H), 3.78-3.88 (m, 1H), 3.73 (dd, J=3.48, 12.39 Hz, 1H), 3.42-3.50 (m, 1H), 2.70-2.79 (m, 1H), 2.57-2.65 (m, 1H), 2.12-2.33 (m, 13H), 1.50-1.71 (m, 5H), 1.29-1.43 (m, 1H), 0.83-1.26 (m, 5H)

LCMS (HPLC Method 2): m/z 606 [M+H]$^+$ @ r.t. 4.84 min.

HRMS (ESI) calcd for $C_{28}H_{38}BrClN_5O_3$ [M+H]$^+$ 606.1841 found 606.1839.

Preparation C

Ethyl (2E)-4-{[(4-acetyl-1H-pyrrol-2-yl)carbonyl]amino}but-2-enoate [(X)]

Step 4

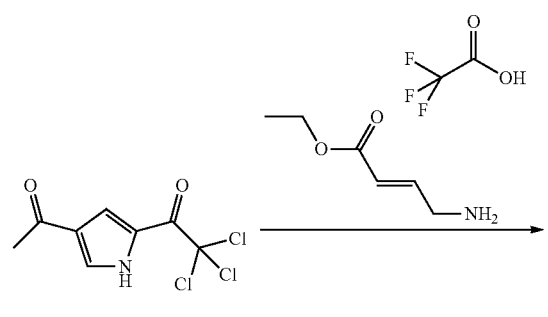

-continued

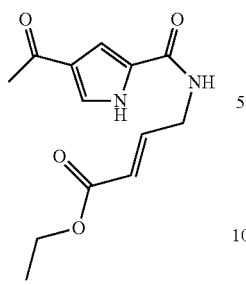

Ethyl (2E)-4-aminobut-2-enoate trifluoroacetate (2.665 g, 10.963 mmol) was added to a solution of 1-(4-acetyl-1H-pyrrol-2-yl)-2,2,2-trichloroethanone (1.8 g, 7.07 mmol) and N,N-diisopropylethylamine (DIPEA) (5.4 mL, 32 mmol) in dichloromethane (20 mL) and the reaction mixture was stirred at room temperature overnight. The solvent was evaporated under vacuum and the residue purified by flash chromatography (SiO$_2$, hexane-EtOAc 1:1) to obtain the title compound as an off-white solid (1.2 g, 65% yield).

$^1$H NMR (400 MHz, DMSO-d$_6$) δ 12.12 (br. s., 1H), 8.55 (t, J=5.61 Hz, 1H), 7.63 (dd, J=1.59, 3.17 Hz, 1H), 7.24 (t, J=1.95 Hz, 1H), 6.90 (td, J=4.71, 15.72 Hz, 1H), 5.88 (td, J=1.83, 15.75 Hz, 1H), 4.11 (q, J=7.08 Hz, 2H), 4.01-4.05 (m, 2H), 2.32-2.35 (m, 3H), 1.20 (t, J=7.08 Hz, 3H).

LCMS (HPLC Method 2): m/z 265 [M+H]$^+$ @ r.t. 4.7 min.

Preparation D

Ethyl (7-acetyl-1-oxo-1,2,3,4-tetrahydropyrrolo[1,2-a]pyrazin-4-yl)acetate [(XI)]

Step 5

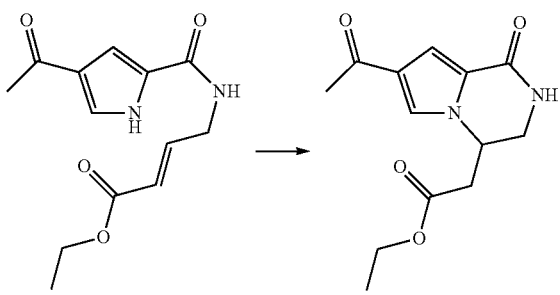 [SMILES: CCOC(=O)/C=C/CNC(=O)c1cc(C(C)=O)c[nH]1 ; CCOC(=O)CC1CNC(=O)c2cc(C(C)=O)cn21]

Diaza(1,3)bicyclo[5.4.0]undecane (DBU) (0.04 mL, 0.3 mmol) was added to a solution of ethyl (2E)-4-{[(4-acetyl-1H-pyrrol-2-yl)carbonyl]amino}but-2-enoate (0.343 g, 1.3 mmol) in acetonitrile (8 mL) and the reaction mixture was stirred at room temperature for 30 min. The solvent was evaporated under vacuum and the residue purified by flash chromatography (SiO$_2$, hexane-EtOAc 1:1) to obtain the title compound as an off-white solid (0.24 g, 70% yield).

LCMS (HPLC Method 2): m/z 265 [M+H]$^+$ @ r.t. 4.15 min

Preparation E

Ethyl {7-[(2E)-3-(dimethylamino)prop-2-enoyl]-1-oxo-1,2,3,4-tetrahydropyrrolo[1,2-a]pyrazin-4-yl}acetate [(XII)]

Step 6

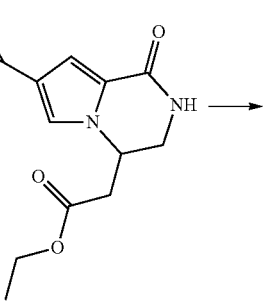

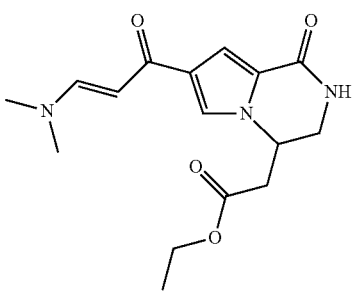

The intermediate ethyl (7-acetyl-1-oxo-1,2,3,4-tetrahydropyrrolo[1,2-a]pyrazin-4-yl)acetate 1 g (3.78 mmol) was dissolved in 5 ml of N,N-dimethylformamide ditert butyl acetal and stirred at 110° C. for 6 hours. The reaction mixture was concentrated and then partitioned between H$_2$O and DCM. The organic layer was washed with brine, dried over Na$_2$SO$_4$, filtered and concentrated under reduced pressure to afford the title compound in quantitative yield.

LC/MS (254 nm) HPLC method 4 m/z 320 [M+H]$^+$@ Rt 3.85 min.

Preparation F

Ethyl [7-(2-aminopyrimidin-4-yl)-1-oxo-1,2,3,4-tetrahydropyrrolo[1,2-a]pyrazin-4-yl]acetate [(XIV)]

Step 7

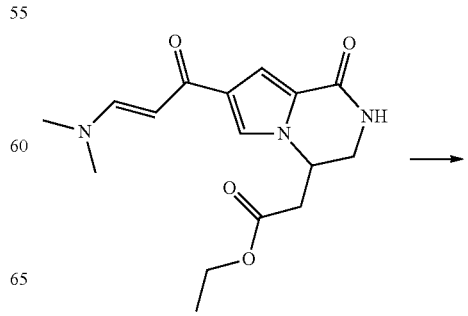

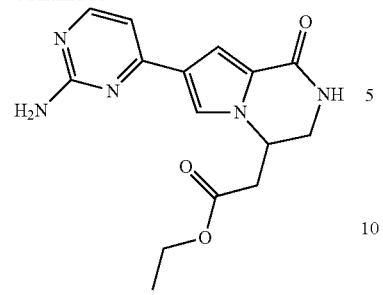

To a suspension of ethyl {7-[(2E)-3-(dimethylamino)prop-2-enoyl]-1-oxo-1,2,3,4-tetrahydropyrrolo[1,2-a]pyrazin-4-yl}acetate (1.21 g, 3.78 mmol) in ethanol (5 mL) guanidine carbonate (915 mg, 7.56 mmol) was added. The mixture was heated under microwave irradiation at 120° C. for 1 hour. The resulting mixture was cooled at room temperature and dried to dryness. The crude solid was purified by flash chromatography on silica gel (eluant: DCM/EtOAc/EtOH 7/2.5/0.5) to afford 357 mg (yield: 30%) of the title compound as an off white solid.

$^1$H NMR (400 MHz, DMSO-ds) δ 8.13 (d, J=5.13 Hz, 1H), 7.76 (d, J=2.20 Hz, 1H), 7.64 (d, J=1.71 Hz, 1H), 7.19 (d, J=1.59 Hz, 1H), 6.84 (d, J=5.25 Hz, 1H), 6.38 (s, 2H), 4.61-4.79 (m, 1H), 4.09 (q, J=7.16 Hz, 2H), 3.71 (dd, J=3.48, 12.51 Hz, 1H), 3.38 (td, J=3.94, 13.37 Hz, 1H), 2.79-2.95 (m, 2H), 1.17 (t, J=7.14 Hz, 3H).

LC/MS (254 nm) HPLC method 2 m/z 316 [M+H]$^+$ @ Rt 3.62 min.

HRMS (ESI) calcd for $C_{15}H_{18}N_5O_3$ [M+H]$^+$ 316.1404 found 316.1400.

Example 2

2-[(4R)-7-(2-aminopyrimidin-4-yl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide [(I) R2=2-aminopyrimidin-4-yl, R3=R4=H, R1=—NHR5, R5=-(1S)-1-cyclohexyl-2-(4-methylpiperazin-1-yl)ethyl](cpd 31)

and

2-[(4S)-7-(2-aminopyrimidin-4-yl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide [(I) R2=2-aminopyrimidin-4-yl, R3=R4=H, R1=—NHR5, R5=-(1S)-1-cyclohexyl-2-(4-methylpiperazin-1-yl)ethyl](cpd 32)

Step 10

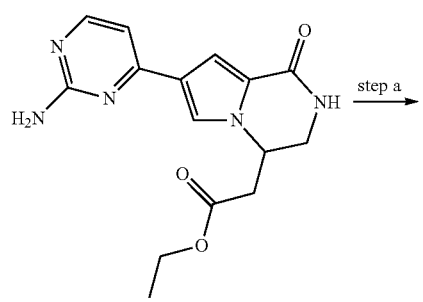

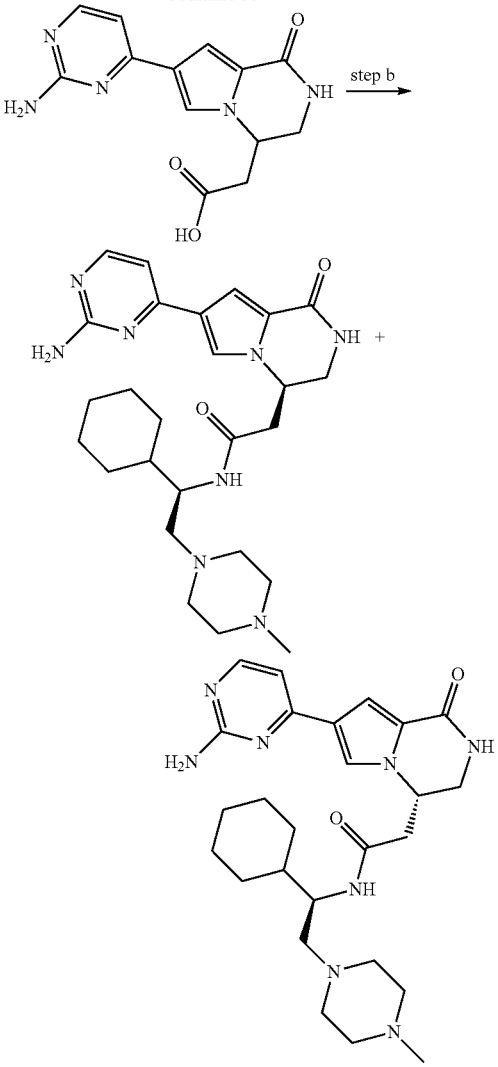

Step a. Preparation of [7-(2-aminopyrimidin-4-yl)-1-oxo-1,2,3,4-tetrahydropyrrolo[1,2-a]pyrazin-4-yl]acetic acid To a solution of ethyl [7-(2-aminopyrimidin-4-yl)-1-oxo-1,2,3,4-tetrahydropyrrolo[1,2-a]pyrazin-4-yl]acetate (350 mg, 1.10 mmol) in a mixture tetrahydrofuran-water (5:1, 5 mL) lithium hydroxide (92 mg, 2.2 mmol) was added and the reaction mixture was stirred at room temperature for 18 h. The THF was evaporated and the aqueous residue diluted with H$_2$O. The aqueous phase was acidified with hydrochloric acid (1 M) until pH<1 and a precipitation occurred; the solid was filtered, washed with water and dried under vacuum. To obtain the title compound as an off-white solid (268 mg, 85% yield)

$^1$H NMR (400 MHz, DMSO-ds) δ 12.62 (br. s., 1H), 8.13 (d, J=5.13 Hz, 1H), 7.76 (d, J=2.32 Hz, 1H), 7.64 (d, J=1.59 Hz, 1H), 7.19 (s, 1H), 6.84 (d, J=5.13 Hz, 1H), 6.39 (s, 2H), 4.57-4.83 (m, 1H), 3.61-3.77 (m, 1H), 3.35-3.45 (m, 2H), 2.73-2.91 (m, 2H).

LCMS (HPLC Method 2): m/z 288 [M+H]$^+$ @ r.t. 2.10 min.

HRMS (ESI) calcd for $C_{13}H_{14}N_5O_3$ [M+H]$^+$ 288.1091 found 288.109.

Step b. A solution of 7-(3-chlorophenyl)-1-oxo-1,2,3,4-tetrahydropyrrolo[1,2-a]pyrazin-4-yl]acetic acid (60 mg, 0.197 mmol), N,N-diisopropylethylamine (DIPEA) (0.250 ml, 1.96 mmol) and HBTU (89 mg, 0.236 mmol) in dry dioxane (10 ml) was stirred for 15 min, then (1S)-1-cyclohexyl-2-(4-methylpiperazin-1-yl)ethanamine trihydrochloride (75.8 mg, 0.226 mmol) was added and the final suspension was stirred for 2 h at 70° C. The solvent was removed in vacuo. The crude was then portioned between ethyl acetate and water, the organic layer dried over sodium sulphate and the solvent removed in vacuo. Purification by flash chromatography on silica gel column (DCM/MeOH/NH$_4$OH 90/10/0.5) gave as first eluted peak the compound 2-[(4R)-7-(2-aminopyrimidin-4-yl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide as a light yellow foam (5 mg 5% yield).

LCMS (HPLC Method 2): m/z 495 [M+H]$^+$ @ r.t. 3.50 min.

HRMS (ESI) calcd for $C_2H_{39}N_8O_2$ [M+H]$^+$ 495.3191 found 495.3190.

and gave as second eluted peak the compound 2-[(4S)-7-(2-aminopyrimidin-4-yl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide as a light yellow foam (15 mg 15% yield).

$^1$H NMR (400 MHz, DMSO-d$_6$) δ 8.10 (d, J=5.13 Hz, 1H), 7.77 (d, J=3.42 Hz, 1H), 7.60 (d, J=9.15 Hz, 1H), 7.52 (d, J=1.71 Hz, 1H), 7.21-7.31 (m, 1H), 7.17 (d, J=1.71 Hz, 1H), 6.79 (d, J=5.13 Hz, 1H), 6.33 (s, 2H), 4.62-4.75 (m, 1H), 3.76-3.83 (m, 1H), 3.72 (dd, J=4.03, 12.69 Hz, 1H), 2.76 (dd, J=8.97, 14.46 Hz, 2H), 2.55 (m, 2H), 2.45-2.18 (m, 15H), 1.69 (m, 1H), 1.48-1.37 (m, 4H), 0.96-0.73 (m, 5H).

LCMS (HPLC Method 2): m/z 495 [M+H]$^+$ @ r.t. 3.55 min.

HRMS (ESI) calcd for $C_{26}H_{39}N_8O_2$ [M+H]$^+$ 495.3191 found 495.3173.

Preparation G

Ethyl [7-(3-chlorophenyl)-6-iodo-1-oxo-1,2,3,4-tetrahydropyrrolo[1,2-a]pyrazin-4-yl]acetate [(XV) R2=3-chlorophenyl, Hal=iodo]

Step 8

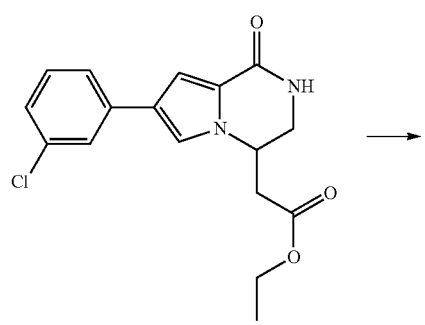

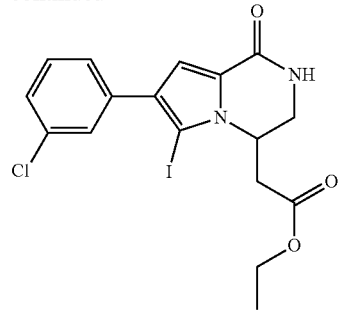

Ethyl [7-(3-chlorophenyl)-1-oxo-1,2,3,4-tetrahydropyrrolo[1,2-a]pyrazin-4-yl]acetate (280 mg, 0.84 mmol) was dissolved in DCM, cooled in an ice bath and CF$_3$COOAg (186 mg, 0.84 mmol) and Iodine (214 mg, 0.84 mmol) were added. The reaction was then warmed up at room temperature and after 1 hour was complete. It was filtered through paper, evaporated and the crude purified by silica chromatography (eluent: Hexane/AcOEt 3/2) to give 228 mg of desired product (59% yield).

$^1$H NMR (400 MHz, DMSO-ds) δ 7.80 (d, J=4.88 Hz, 1H), 7.59 (t, J=1.77 Hz, 1H), 7.48-7.54 (m, 1H), 7.45 (t, J=7.81 Hz, 1H), 7.30-7.41 (m, 1H), 7.00 (s, 1H), 4.65-4.81 (m, 1H), 4.12 (q, J=7.08 Hz, 2H), 3.84 (dd, J=4.21, 13.49 Hz, 1H), 3.36-3.47 (m, 1H), 2.81 (dd, J=10.01, 15.50 Hz, 1H), 2.58 (dd, J=3.60, 15.68 Hz, 1H), 1.21 (t, J=7.08 Hz, 3H).

LCMS (HPLC Method 3): m/z 458 [M+H]$^+$ @ r.t. 3.59 min.

HRMS (ESI) calcd for $C_{17}H_{17}ClIN_2O_3$ [M+H]$^+$ 458.9967 found 458.9963

According to this same methodology, but employing suitable substituted derivatives, the following compound was prepared Ethyl [7-(3-fluorophenyl)-6-iodo-1-oxo-1,2,3,4-tetrahydropyrrolo[1,2-a]pyrazin-4-yl]acetate $^1$H NMR (400 MHz, DMSO-d$_6$) δ 7.80 (d, J=4.88 Hz, 1H), 7.42-7.50 (m, 1H), 7.38-7.42 (m, 1H), 7.32-7.38 (m, 1H), 7.13 (dddd, J=1.16, 2.69, 7.95, 9.08 Hz, 1H), 7.00 (s, 1H), 4.69-4.77 (m, 1H), 4.12 (q, J=7.12 Hz, 2H), 3.84 (dd, J=3.78, 13.30 Hz, 1H), 3.37-3.44 (m, 1H), 2.81 (dd, J=10.13, 15.50 Hz, 1H), 2.58 (dd, J=3.23, 15.93 Hz, 1H), 1.16-1.25 (m, 3H)

LCMS (HPLC Method 2): m/z 443 [M+H]$^+$ @ r.t.=5.64 min

HRMS (ESI) calcd for $C_{17}H_{17}FIN_2O_3$ [M+H]$^+$ 443.0263. found 443.0255

Example 3

2-[(4R)-7-(3-chlorophenyl)-6-iodo-1-oxo-1,2,3,4-tetrahydropyrrolo[1,2-a]pyrazin-4-yl]-N-[(2S)-1-(4-methylpiperazin-1-yl)propan-2-yl]acetamide [(I) R2=3-chlorophenyl, R3=Iodo, R4=H, R1=NHR5 R5=-(2S)-1-(4-methylpiperazin-1-yl)propan-2-yl](cpd 33)

and

2-[(4S)-7-(3-chlorophenyl)-6-iodo-1-oxo-1,2,3,4-tetrahydropyrrolo[1,2-a]pyrazin-4-yl]-N-[(2S)-1-(4-methylpiperazin-1-yl)propan-2-yl]acetamide [(I) R2=3-chlorophenyl, R3=Iodo, R4=H, R1=NHR5 R5=-(2S)-1-(4-methylpiperazin-1-yl)propan-2-yl](cpd 34)

Step 10

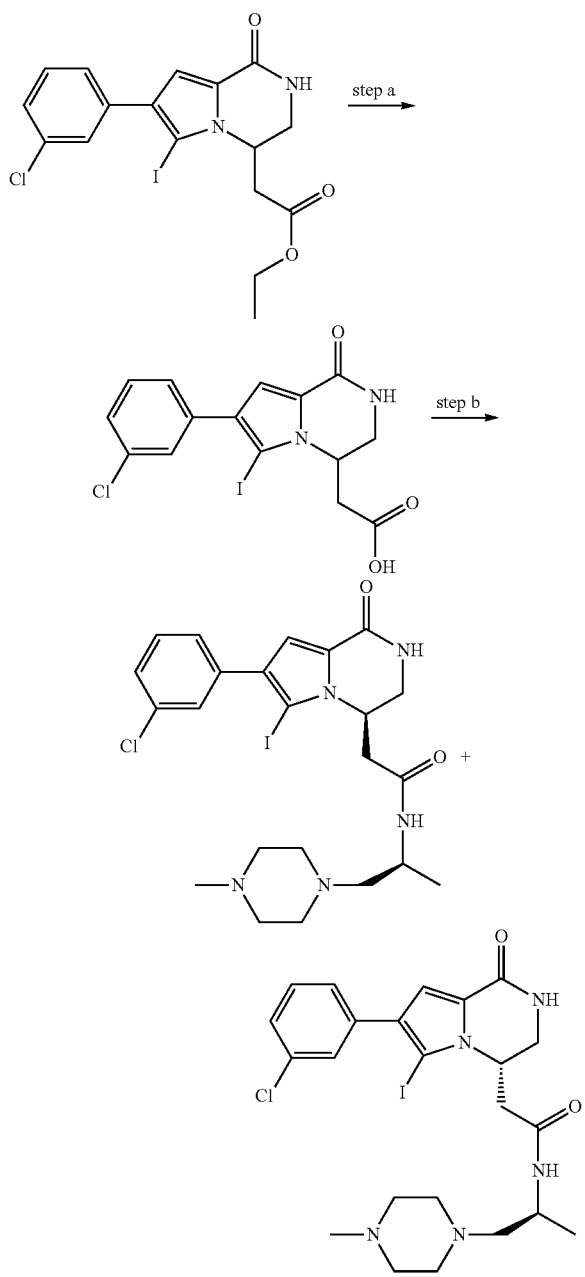

Step a. Preparation of [7-(3-chlorophenyl)-6-iodo-1-oxo-1,2,3,4-tetrahydropyrrolo[1,2-a]pyrazin-4-yl]acetic acid To a solution of ethyl [7-(3-chlorophenyl)-6-iodo-1-oxo-1,2,3,4-tetrahydropyrrolo[1,2-a]pyrazin-4-yl]acetate (0.108 g, 0.23 mmol) in a mixture ethanol-water (5:1, 5 mL) lithium hydroxide (17 mg, 0.71 mmol) was added and the reaction mixture was stirred at room temperature for 2 h. The EtOH was evaporated and the aqueous residue diluted with $H_2O$. The aqueous phase was acidified with hydrochloric acid (1 M) until pH<1 and extracted with Ethyl.Acetate; the organic phase was dried on $Na_2SO_4$, filtered and evaporated to leave the title compound as a clear oil (85% yield) that was submitted to the next step without characterization.

Step b. A solution of [7-(3-chlorophenyl)-6-iodo-1-oxo-1,2,3,4-tetrahydropyrrolo[1,2-a]pyrazin-4-yl]acetic acid (90 mg, 0.21 mmol), N,N-diisopropylethylamine (DIPEA) (0.324 ml, 1.88 mmol) and HBTU (95 mg, 0.25 mmol) in dry dioxane (10 ml) was stirred for 15 min; then (2S)-1-(4-methylpiperazin-1-yl)propan-2-amine trihydrochloride (66 mg, 0.25 mmol) was added and the final suspension was stirred for 3 h at 80° C.

The solvent was removed in vacuo. The crude was then portioned between ethyl acetate and water, the organic layer dried over sodium sulphate and the solvent removed in vacuo. Purification by flash chromatography on silica gel column (DCM/MeOH/$NH_4OH$ 90/10/0.5 and 80/20/0.5) gave as first eluted peak the compound 2-[(4R)-7-(3-chlorophenyl)-6-iodo-1-oxo-1,2,3,4-tetrahydropyrrolo[1,2-a]pyrazin-4-yl]-N-[(2S)-1-(4-methylpiperazin-1-yl)propan-2-yl]acetamide as a white foam 23 mg, 20% Y.

$^1$H NMR (400 MHz, DMSO-$d_6$) δ 7.83 (d, J=8.06 Hz, 1H), 7.78 (d, J=5.13 Hz, 1H), 7.59 (t, J=1.71 Hz, 1H), 7.48-7.55 (m, 1H), 7.44 (t, J=7.81 Hz, 1H), 7.32-7.40 (m, 1H), 6.99 (s, 1H), 4.72 (td, J=3.77, 10.89 Hz, 1H), 3.87-4.03 (m, 1H), 3.79 (dd, J=3.84, 13.00 Hz, 1H), 3.37-3.43 (m, 1H), 2.57-2.69 (m, 1H), 2.19-2.43 (m, 10H), 2.08-2.18 (m, 4H), 1.05 (d, J=6.59 Hz, 3H).

LCMS (HPLC Method 2): m/z 570 [M+H]$^+$ @ r.t. 2.35 min.

HRMS (ESI) calcd for $C_{23}H_{30}ClIN_5O_2$ [M+H]$^+$ 570.1128 found 570.1107

As second eluted peak the compound 2-[(4S)-7-(3-chlorophenyl)-6-iodo-1-oxo-1,2,3,4-tetrahydropyrrolo[1,2-a]pyrazin-4-yl]-N-[(2S)-1-(4-methylpiperazin-1-yl)propan-2-yl]acetamide as a white foam 10 mg, 8% Y.

$^1$H NMR (400 MHz, DMSO-ds) δ 7.86 (d, J=8.18 Hz, 1H), 7.80 (d, J=4.88 Hz, 1H), 7.59 (t, J=1.71 Hz, 1H), 7.49-7.55 (m, 1H), 7.44 (t, J=7.81 Hz, 1H), 7.32-7.40 (m, 1H), 6.99 (s, 1H), 4.63-4.79 (m, 1H), 3.99 (td, J=7.09, 14.49 Hz, 1H), 3.79 (dd, J=3.84, 13.00 Hz, 1H), 3.48 (dd, J=5.00, 13.06 Hz, 1H), 2.61 (dd, J=11.11, 14.65 Hz, 1H), 2.23-2.46 (m, 10H), 2.09-2.19 (m, 4H), 0.93-1.12 (m, 3H).

LCMS (HPLC Method 2): m/z 570 [M+H]$^+$ @ r.t. 2.48 min.

HRMS (ESI) calcd for $C_2H_{30}ClIN_5O_2$ [M+H]$^+$ 570.1128 found 570.1121.

According to this same methodology, but employing suitable substituted derivatives, the following compounds were prepared:

2-[(4R)-7-(3-fluorophenyl)-6-iodo-1-oxo-1,2,3,4-tetrahydropyrrolo[1,2-a]pyrazin-4-yl]-N-[(2S)-1-(4-methylpiperazin-1-yl)propan-2-yl]acetamide acetamide [(I) R2=3-fluorophenyl, R3=Iodo, R4=H, R1=NHR5 R5=-(2S)-1-(4-methylpiperazin-1-yl)propan-2-yl](cpd 35)

$^1$H NMR (400 MHz, DMSO-ds) δ 7.83 (d, J=8.06 Hz, 1H), 7.78 (d, J=4.88 Hz, 1H), 7.32-7.49 (m, 3H), 7.09-7.17 (m, 1H), 6.99 (s, 1H), 4.68-4.73 (m, 1H), 3.89-4.00 (m, 1H), 3.79 (dd, J=4.09, 13.37 Hz, 1H), 3.36-3.43 (m, 1H), 2.62 (dd, J=10.92, 14.95 Hz, 1H), 2.21-2:43 (m, 9H), 2.13-2.18 (m, 1H), 2.11-2.13 (s, 3H), 1.05 (d, J=6.59 Hz, 3H).

LCMS (HPLC Method 4): m/z 554 [M+H]$^+$ @ r.t. 2.33 min.

HRMS (ESI) calcd for $C_{23}H_{30}FIN_5O_2$ [M+H]$^+$ 554.1423 found 554.1412.

2-[(4S)-7-(3-fluorophenyl)-6-iodo-1-oxo-1,2,3,4-tetrahydropyrrolo[1,2-a]pyrazin-4-yl]-N-[(2S)-1-(4-methylpiperazin-1-yl)propan-2-yl]acetamide [(I) R2=3-fluorophenyl, R3=Iodo, R4=H, R1=NHR5 R5=-(2S)-1-(4-methylpiperazin-1-yl)propan-2-yl](cpd 36)

$^1$H NMR (400 MHz, DMSO-ds) δ 7.86 (d, J=8.42 Hz, 1H), 7.80 (d, J=4.76 Hz, 1H), 7.28-7.49 (m, 3H), 7.07-7.19 (m, 1H), 6.99 (s, 1H), 4.61-4.80 (m, 1H), 3.99 (td, J=7.05, 14.46

Hz, 1H), 3.79 (dd, J=4.09, 13.24 Hz, 1H), 3.48 (dd, J=5.07, 13.12 Hz, 1H), 2.61 (dd, J=11.05, 14.59 Hz, 1H); 2.22-2.46 (m, 9H), 2.10-2.18 (m, 4H), 1.03 (d, J=6.47 Hz, 3H)

LCMS (HPLC Method 4): m/z 554 [M+H]+ @ r.t. 2.44 min.

HRMS (ESI) calcd for $C_{23}H_{30}FIN_5O_2$ [M+H]+ 554.1423 found 554.1397.

Preparation H

Ethyl [6-bromo-7-(3-fluorophenyl)-1-oxo-1,2,3,4-tetrahydropyrrolo[1,2-a]pyrazin-4-yl]acetate [(XV) R2=3-chlorophenyl, Hal=Bromo]

Step 8

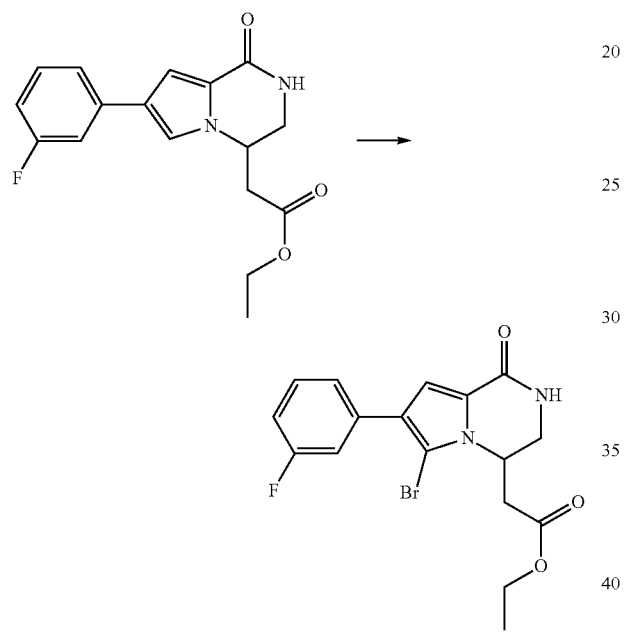

Ethyl [7-(3-fluorophenyl)-1-oxo-1,2,3,4-tetrahydropyrrolo[1,2-a]pyrazin-4-yl]acetate (116 mg, 0.36 mmol) was dissolved in dry dioxane (15 ml) and reacted with N-bromo succinimide (72 mg, 0.40 mmol) overnight at room temperature. The crude was dried under vacuo and purified on silica gel with Ethyl Acetate/Hexane 3/2 to give the wanted compound in quantitative yield.

1H NMR (400 MHz, DMSO-$d_6$) δ 7.83 (d, J=4.88 Hz, 1H), 7.45-7.49 (m, 2H), 7.39-7.44 (m, 1H), 7.14 (ddd, J=3.23, 5.80, 8.91 Hz, 1H), 7.07 (s, 1H), 4.72-4.83 (m, 1H), 4.10 (q, J=7.20 Hz, 2H), 3.85 (dd, J=4.03, 13.43 Hz, 1H), 3.42 (dd, J=5.00, 13.06 Hz, 1H), 2.83 (dd, J=9.58, 15.44 Hz, 1H), 2.61 (dd, J=4.15, 15.26 Hz, 1H), 1.17-1.21 (m, 3H)

LCMS (HPLC Method 2): m/z 395 [M+H]+ @ r.t.=6.02 min

Example 4

2-[(4R)-6-bromo-7-(3-fluorophenyl)-1-oxo-1,2,3,4-tetrahydropyrrolo[1,2-a]pyrazin-4-yl]-N-[(2S)-1-(4-methylpiperazin-1-yl)propan-2-yl]acetamide [(I) R2=3-fluorophenyl, R3=Bromo, R4=H, R1=NHR5 R5=-(2S)-1-(4-methylpiperazin-1-yl)propan-2-yl](cpd 37)

and

2-[(4S)-6-bromo-7-(3-fluorophenyl)-1-oxo-1,2,3,4-tetrahydropyrrolo[1,2-a]pyrazin-4-yl]-N-[(2S)-1-(4-methylpiperazin-1-yl)propan-2-yl]acetamide [(I) R2=3-fluorophenyl, R3=Bromo, R4=H, R1=NHR5 R5=-(2S)-1-(4-methylpiperazin-1-yl)propan-2-yl](cpd 38)

Step 10

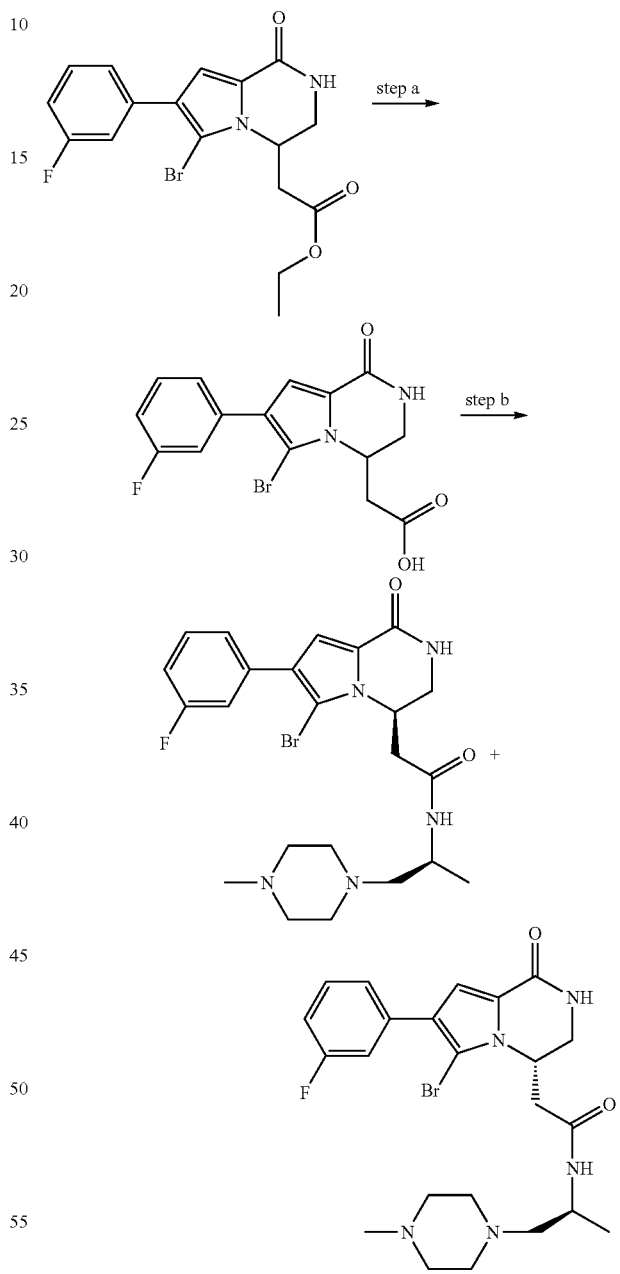

Step a. Preparation of [6-bromo-7-(3-fluorophenyl)-1-oxo-1,2,3,4-tetrahydropyrrolo[1,2-a]pyrazin-4-yl]acetic acid To a solution of Ethyl [6-bromo-7-(3-fluorophenyl)-1-oxo-1,2,3,4-tetrahydropyrrolo[1,2-a]pyrazin-4-yl]acetate (0.095 g, 0.24 mmol) in a mixture of isopropanol-water (1:4, 5 mL) lithium hydroxide (17 mg, 0.72 mmol) was added and the reaction mixture was stirred at room temperature for 2 h. The solvents were evaporated and the aqueous residue was acidified with hydrochloric acid (1 M) until pH<1 and then extracted with ethyl acetate; the organic phase was dried on Na₂SO₄, filtered and evaporated to leave the title compound as a clear oil (85% yield) that was submitted to the next step without characterization.

Step b. A solution of [7-(3-fluorophenyl)-6-bromo-1-oxo-1,2,3,4-tetrahydropyrrolo[1,2-a]pyrazin-4-yl]acetic acid (50 mg, 0.14 mmol), N,N-diisopropylethylamine (DIPEA) (0.211 ml, 1.23 mmol) and HBTU (62 mg, 0.16 mmol) in dry dioxane (5 ml) was stirred for 15 min; then (2S)-1-(4-methylpiperazin-1-yl)propan-2-amine trihydrochloride (43 mg, 0.16 mmol) was added and the final suspension was stirred for 3 h at 80° C.

The solvent was removed in vacuo. The crude was then portioned between ethyl acetate and water, the organic layer dried over sodium sulphate and the solvent removed in vacuo. Purification by flash chromatography on silica gel column (DCM/MeOH/NH₄OH 90/10/0.5 and 80/20/0.5) gave as first eluted peak the compound 2-[(4R)-6-bromo-7-(3-fluorophenyl)-1-oxo-1,2,3,4-tetrahydropyrrolo[1,2-a]pyrazin-4-yl]-N-[(2S)-1-(4-methylpiperazin-1-yl)propan-2-yl]acetamide as a white foam 13 mg.

$^1$H NMR (400 MHz, DMSO-d6) δ 7.79-7.88 (m, 2H), 7.38-7.49 (m, 3H), 7.09-7.19 (m, 1H), 7.06 (s, 1H), 4.72-4.80 (m, 1H), 3.89-4.00 (m, 1H), 3.80 (dd, J=4.03, 13.67 Hz, 1H), 3.40 (dd, J=5.19, 13.00 Hz, 1H), 2.60-2.69 (m, 1H), 2.20-2.42 (m, 10H), 2.06-2.16 (m, 4H), 1.04 (d, J=6.59 Hz, 3H)

LCMS (HPLC Method 2): m/z 506 [M+H]⁺ @ r.t.=4.32 min

HRMS (ESI) calcd for C₂H₃₀BrFN₅O₂ [M+H]⁺ 506.1562 found 506.1574.

As second eluted peak the compound 2-[(4S)-6-bromo-7-(3-fluorophenyl)-1-oxo-1,2,3,4-tetrahydropyrrolo[1,2-a]pyrazin-4-yl]-N-[(2S)-1-(4-methylpiperazin-1-yl)propan-2-yl]acetamide as a white foam 10 mg.

$^1$H NMR (400 MHz, DMSO-d6) δ 7.87 (d, J=8.30 Hz, 1H), 7.84 (d, J=5.00 Hz, 1H), 7.36-7.50 (m, 3H), 7.09-7.17 (m, 1H), 7.06 (s, 1H), 4.72-4.82 (m, 1H), 3.91-4.02 (m, 1H), 3.80 (dd, J=3.78, 13.30 Hz, 1H), 3.48 (dd, J=5.00, 13.18 Hz, 1H), 2.64 (dd, J=10.68, 14.59 Hz, 1H), 2.20-2.45 (m, 10H), 2.09-2.18 (m, 4H), 1.02 (d, J=6.59 Hz, 3H)

LCMS (HPLC Method 2): m/z 506 [M+H]⁺ @ r.t.=4.52 min

HRMS (ESI) calcd for C₂₃H₃₀BrFN₅O₂ [M+H]⁺ 506.1562 found 506.1542.

According to this same methodology, but employing suitable substituted derivatives, the following compounds were prepared:

2-[(4R)-6-bromo-7-(3-fluorophenyl)-1-oxo-1,2,3,4-tetrahydropyrrolo[1,2-a]pyrazin-4-yl]-N-[(2S)-1-hydroxypropan-2-yl]acetamide [(I) R2=3-fluorophenyl, R3=Bromo, R4=H, R1=NHR5 R5=-(2S)-1-hydroxypropan-2-yl](cpd 39)

$^1$H NMR (400 MHz, DMSO-d6) δ 7.87 (d, J=7.81 Hz, 1H), 7.80 (d, J=5.00 Hz, 1H), 7.39-7.48 (m, 3H), 7.09-7.17 (m, 1H), 7.06 (s, 1H), 4.74-4.81 (m, 1H), 4.67 (t, J=5.61 Hz, 1H), 3.74-3.84 (m, 2H), 3.30-3.38 (m, 1H), 3.17-3.24 (m, 2H), 2.61-2.73 (m, 1H), 2.28-2.40 (m, 1H), 1.04 (d, J=6.71 Hz, 3H)

HRMS (ESI) calcd for C₁₈H₂₀BrFN₃O₃ [M+H]⁺ 424.0667 found 424.0656

LCMS (HPLC Method 2): m/z 424 [M+H]⁺ @ r.t.=4.86 min.

2-[(4S)-6-bromo-7-(3-fluorophenyl)-1-oxo-1,2,3,4-tetrahydropyrrolo[1,2-a]pyrazin-4-yl]-N-[(2S)-1-hydroxypropan-2-yl]acetamide [(I) R2=3-fluorophenyl, R3=Bromo, R4=H, R1=NHR5 R5=-(2S)-1-hydroxypropan-2-yl](cpd 40)

$^1$H NMR (400 MHz, DMSO-d₆) δ 7.86 (d, J=7.93 Hz, 1H), 7.78 (d, J=5.00 Hz, 1H), 7.38-7.48 (m, 3H), 7.09-7.17 (m, 1H), 7.06 (s, 1H), 4.73-4.82 (m, 1H), 4.68 (t, J=5.68 Hz, 1H), 3.75-3.84 (m, 2H), 3.38-3.43 (m, 1H), 3.19-3.28 (m, 2H), 2.67 (dd, J=10.44, 14.95 Hz, 1H), 2.32-2.39 (m, 1H), 1.01 (d, J=6.71 Hz, 3H)

HRMS (ESI) calcd for C₁₈H₂₀BrFN₃O₃ [M+H]⁺ 424.0667 found 424.0651

LCMS (HPLC Method 2): m/z 424 [M+H]⁺ @ r.t.=4.99 min

2-[6-bromo-7-(3-fluorophenyl)-1-oxo-1,2,3,4-tetrahydropyrrolo[1,2-a]pyrazin-4-yl]acetamide [(I) R2=3-fluorophenyl, R3=Bromo, R4=H, R1=NH₂](cpd 41)

$^1$H NMR (400 MHz, DMSO-d6) δ 7.81 (d, J=0.5.25 Hz, 1H), 7.52 (br. s., 1H), 7.44-7.49 (m, 2H), 7.39-7.44 (m, 1H), 7.08-7.18 (m, 2H), 7.06 (s, 1H), 4.75 (td, J=3.43, 11.20 Hz, 1H), 3.81 (dd, J=3.42, 13.30 Hz, 1H), 3.41 (dd, J=5.07, 13.37 Hz, 1H), 2.63-2.74 (m, 1H), 2.24-2.38 (m, 1H)

LCMS (HPLC Method 2): m/z 366 [M+H]⁺ @ r.t.=4.75 min

HRMS (ESI) calcd for C₁₅H₁₄BrFN₃O₂ [M+H]366.0248 found 366.0235

Preparation I

Ethyl [7-(3-chlorophenyl)-1-oxo-6-phenyl-1,2,3,4-tetrahydropyrrolo[1,2-a]pyrazin-4-yl]acetate [(XVI) R2=3-chlorophenyl, R3=phenyl]

Step 9

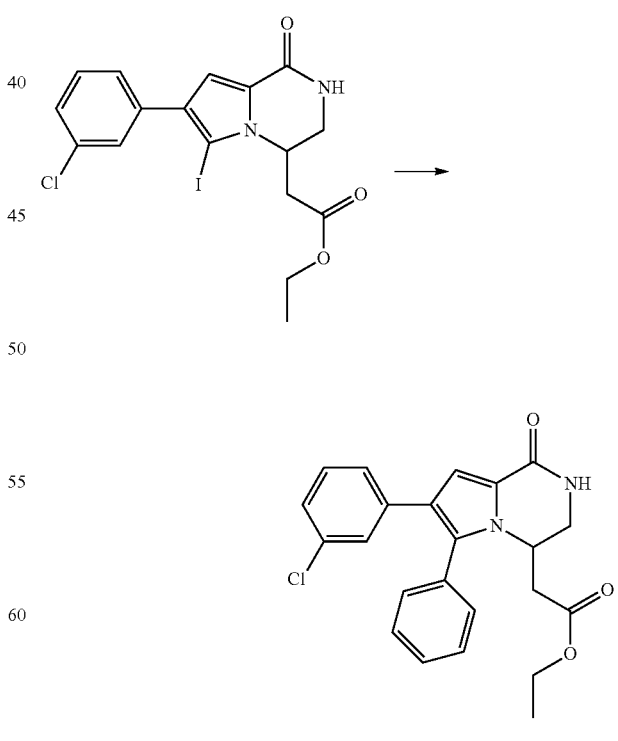

To a solution of ethyl [7-(3-chlorophenyl)-6-iodo-1-oxo-1,2,3,4-tetrahydropyrrolo[1,2-a]pyrazin-4-yl]acetate (123 mg, 0.269 mmol) in 9 ml of 1,4-dioxane and 1 ml of water, under argon atmosphere, phenylboronic acid (130 mg, 1.07 mmol), bis(triphenylphosphine)palladium(II) dichloride (9:4 mg, 0.013 mmol), sodium carbonate (85.0 mg, 0.80 mmol) and lithium chloride (34 mg, 0.81 mmol) were successively added. The mixture was heated at 100° for 4 hour in a sealed vial. The reaction was filtered through a celite pad and the solvent evaporated to dryness. The crude was then portioned between ethyl acetate and water, the organic layer dried over sodium sulphate and the solvent removed in vacuo. Purification by flash chromatography on silica gel column (EtOAc/Hex 3/2) led to the wanted compound in 90% yield.

$^1$H NMR (400 MHz, DMSO-d6) δ 7.75 (d, J=4.76 Hz, 1H), 7.46-7.53 (m, 3H), 7.37-7.42 (m, 2H), 7.18-7.24 (m, 1H), 7.13-7.17 (m, 1H), 7.08-7.11 (m, 2H), 7.07 (s, 1H), 4.49-4.56 (m, 1H), 3.82-3.96 (m, 2H), 3.26-3.34 (m, 2H), 2.69-2.78 (m, 1H), 2.25-2.36 (m, 1H), 1.05 (t, J=7.14 Hz, 3H).

LCMS (HPLC Method 2): m/z 409 [M+H]$^+$ @ r.t. 6.80 min.

HRMS (ESI) calcd for $C_{23}H_{22}ClN_2O_3$ [M+H]$^+$ 409.1314 found 409.1301.

Example 5

2-[(4R)-7-(3-chlorophenyl)-1-oxo-6-phenyl-1,2,3,4-tetrahydropyrrolo[1,2-a]pyrazin-4-yl]-N-[(2S)-1-(4-methylpiperazin-1-yl)propan-2-yl]acetamide [(I) R2=3-chlorophenyl, R3=phenyl, R4=H, R1=NHR5 R5=-(2S)-1-hydroxypropan-2-yl](cpd 42)

and

2-[(4S)-7-(3-chlorophenyl)-1-oxo-6-phenyl-1,2,3,4-tetrahydropyrrolo[1,2-a]pyrazin-4-yl]-N-[(2S)-1-(4-methylpiperazin-1-yl)propan-2-yl]acetamide [(I) R2=3-chlorophenyl, R3=phenyl, R4=H, R1=NHR5 R5=-(2S)-1-hydroxypropan-2-yl](cpd 43)

Step 10

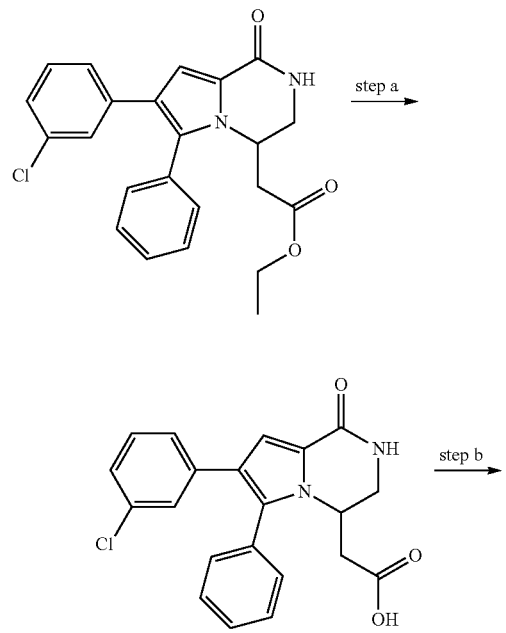

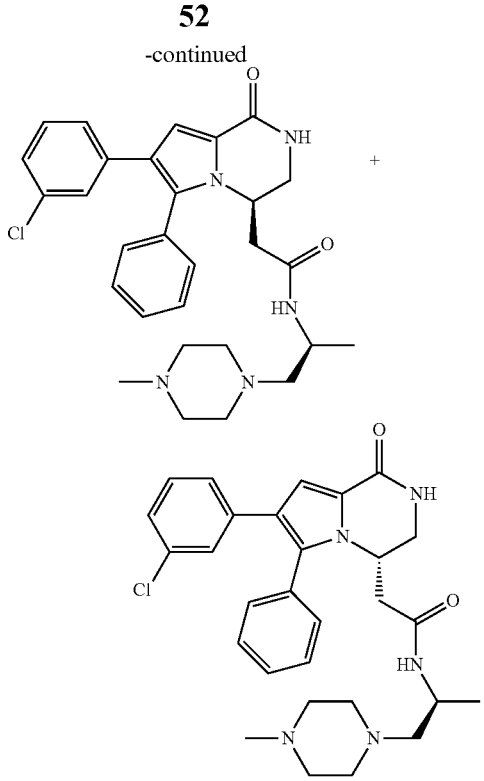

Step a. Preparation of [7-(3-chlorophenyl)-1-oxo-6-phenyl-1,2,3,4-tetrahydropyrrolo[1,2-a]pyrazin-4-yl]acetic acid To a solution of ethyl [7-(3-chlorophenyl)-1-oxo-6-phenyl-1,2,3,4-tetrahydropyrrolo[1,2-a]pyrazin-4-yl]acetate (0.17 g, 0.42 mmol) in a mixture of isopropanol-water (1:4, 5 mL) lithium hydroxide (30 mg, 1.25 mmol) was added and the reaction mixture was stirred at room temperature for 2 h. The solvents were evaporated and the aqueous residue was acidified with hydrochloric acid (1 M) until pH<1 and then extracted with ethyl acetate; the organic phase was dried on Na$_2$SO$_4$, filtered and evaporated to leave the tide compound as a clear oil (85% yield) that was submitted to the next step without characterization.

Step b. A solution of [7-(3-chlorophenyl)-1-oxo-6-phenyl-1,2,3,4-tetrahydropyrrolo[1,2-a]pyrazin-4-yl]acetic acid (90 mg, 0.24 mmol), N,N-diisopropylethylamine (DIPEA) (0.367 ml, 2.13 mmol) and HBTU (107 mg, 0.28 mmol) in dry dioxane (5 ml) was stirred for 15 min; then (2S)-1-(4-methylpiperazin-1-yl)propan-2-amine trihydrochloride (75 mg, 0.28 mmol) was added and the final suspension was stirred for 4 h at 80° C.

The solvent was removed in vacuo. The crude was then portioned between ethyl acetate and water, the organic layer dried over sodium sulphate and the solvent removed in vacuo. Purification by flash chromatography on silica gel column (DCM/MeOH/NH$_4$OH 90/10/0.5 and 0.80/20/0.5) gave as first eluted peak the compound 2-[(4R)-7-(3-chlorophenyl)-1-oxo-6-phenyl-1,2,3,4-tetrahydropyrrolo[1,2-a]pyrazin-4-yl]-N-[(2S)-1-(4-methylpiperazin-1-yl)propan-2-yl]acetamide as a white solid.

$^1$H NMR (400 MHz, DMSO-d$_6$) δ 7.71 (d, J=4.88 Hz, 1H), 7.62 (d, J=8.06 Hz, 1H), 7.44-7.51 (m, 3H), 7.33-7.41 (m, 2H), 7.16-7.23 (m, 1H), 7.12-7.16 (m, 1H), 7.06-7.10 (m, 2H), 7.05 (s, 1H), 4.45-4.59 (m, 1H), 3.68-3.91 (m, 2H), 2.60 (dd, J=10.74, 15.14 Hz, 1H), 2.55-2.65 (m, 1H), 2.15-2.33 (m, 10H), 2.11-2.12 (m, 3H), 1.97-2.10 (m, 3H), 0.96 (d, J=6.59 Hz, 3H)

LCMS (HPLC Method 2): m/z 520 [M+H]$^+$ @ r.t.=5.03 min

HRMS (ESI) calcd for $C_{29}H_{34}ClN_5O_2$ [M+H]$^+$ 520.2474 found 520.2481.

As second eluted peak the compound 2-[(4S)-7-(3-chlorophenyl)-1-oxo-6-phenyl-1,2,3,4-tetrahydropyrrolo[1,2-a]pyrazin-4-yl]-N-[(2S)-1-(4-methylpiperazin-1-yl)propan-2-yl]acetamide as a white foam.

1H NMR (400 MHz, DMSO-$d_6$) δ 7.74 (d, J=4.76 Hz, 1H), 7.70 (d, J=8.30 Hz, 1H), 7.45-7.54 (m, 3H), 7.37-7.42 (m, 2H), 7.17-7.24 (m, 1H), 7.12-7.17 (m, 1H), 7.07-7.11 (m, 2H), 7.05 (s, 1H), 4.41-4.60 (m, 1H), 3.74-3.90 (m, 2H), 3.35-3.40 (m, 1H), 2.61 (dd, J=10.86, 14.65 Hz, 1H), 2.23-2.37 (m, 8H), 2.19 (dd, J=7.38, 12.14 Hz, 1H), 2.12 (s, 3H), 2.03-2.10 (m, 1H), 1.99 (dd, J=2.62, 14.71 Hz, 1H), 0.92 (d, J=6.71 Hz, 3H)

LCMS (HPLC Method 2): m/z 520 [M+H]$^+$ @ r.t.=5.22 min

HRMS (ESI) calcd for $C_{29}H_{35}ClN_5O_2$ [M+H]$^+$ 520.2474 found 520.2493

According to this same methodology, but employing suitable substituted derivatives, the following compound was prepared:

2-[(4S)-7-(3-chlorophenyl)-1-oxo-6-phenyl-1,2,3,4-tetrahydropyrrolo[1,2-a]pyrazin-4-yl]-N-[(3R)-piperidin-3-yl] acetamide hydrochloride [(I) R2=3-chlorophenyl, R3=phenyl, R4=H, R1=NHR5 R5=(3R)-piperidin-3-yl] (cpd 44)

1H NMR (400 MHz, DMSO-d6) δ 8.03 (d, J=7.2 Hz, 1 H) 7.73 (d, J=5.1 Hz, 1 H) 7.34-7.54 (m, 5 H) 7.18-7.23 (m, 1 H) 7.12-7.16 (m, 1 H) 7.00-7.10 (m, 3 H) 4.50-4.54 (m, 1 H) 3.85 (dd, J=12.8, 4.0 Hz, 1 H) 3.68 (m, 1H), 3.50 (m, 2H), 3.18 (m, 1H), 2.60-2.76 (m, 3H), 2.46 (m, 1H), 1.73 (m, 2H), 1.27-1.63 (m, 2H),

LCMS (HPLC Method 2): m/z 463 [M+H]$^+$ @ r.t.=4.89 min

HRMS (ESI) calcd for $C_{25}H_{28}ClN_4O_2$ [M+H]$^+$ 463.1895 found 463.1896

Pharmacology

The compounds of formula (I) are active as protein kinase inhibitors and are therefore useful, for instance, to restrict the unregulated proliferation of tumour cells.

In therapy, they may be used in the treatment of various tumours, such as those formerly defined, as well as in the treatment of other cell proliferative disorders such as benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

The short forms and abbreviations used herein have the following meaning:
Ci Curie
DMSO dimethylsulfoxide
KDa kiloDalton
microCi microCurie
mg milligram
microg microgram
ng nanogram
L liter
mL milliliter
μL microliter
M molar
mM millimolar
μM micromolar
nM nanomolar
Biochemical Assay for Inhibitors of PIM1 Kinase Activity The inhibitory activity of putative kinase inhibitors and the potency of selected compounds were determined using a trans-phosphorylation assay.

Specific peptide or protein substrates are trans-phosphorylated by their specific ser-thr or tyr kinase in the presence of ATP traced with $^{33}$P-γ-ATP, and in the presence of their own optimal buffer and cofactors.

At the end of the phosphorylation reaction, more than 98% unlabeled ATP and radioactive ATP is captured by an excess of the ion exchange Dowex resin; the resin then settles down to the bottom of the reaction plate by gravity. Supernatant is subsequently withdrawn and transferred into a counting plate, then evaluated by β-counting.

Reagents/Assay Conditions
i. Dowex Resin Preparation 500 g of wet resin (SIGMA, custom prepared resin DOWEX 1×8 200-400 mesh, 2.5 Kg) are weighed out and diluted to 2 L in 150 mM sodium formate, pH 3.00.

The resin is allowed to settle down (some hours) and then the supernatant is discarded.

After three washes as above over a couple of days, the resin is allowed to settle and two volumes (wrt the resin volume) of 150 mM sodium formate buffer are added.

The pH is then measured and should be around 3.00.

The washed resin is stable for more than one week; the stock resin is kept at 4° C. before use.

ii. Kinase Buffer (KB)

The buffer for PIM1 assay was composed of HEPES 50 mM, at pH 7.5, with 10 mM MgCl$_2$, 1 mM DTT, 3 μM NaVO$_3$, and 0.2 mg/mL BSA.

Full-length human PIM1 was expressed and purified as described in Bullock A N, et al., J. Biol. Chem. 2005, 280, 41675-82.

The enzyme showed a linear kinetic after a step of pre-activation by auto-phosphorylation in the following conditions: 1.7 μM PIM1 was incubated 1 h at 28° C. in the presence of 125 μM ATP.

iii. Assay Conditions
ATP concentration: 200 μM
$^{33}$P-γ-ATP: 6 nM
Enzyme concentration: 1 nM
Substrate concentration Aktide (Chemical Abstract Service Registry Number 324029-01-8): 25 μM iv. Robotized Dowex Assay
The test mix consisted of:
1) 3× Enzyme mix (done in Kinase Buffer 3×), 5 μL/well
2) 3× substrate and ATP mix (done in ddH$_2$O), together with $^{33}$P-γ-ATP, 5 μL/well
3) 3× test compounds (diluted into ddH$_2$O-3% DMSO)—5 μL/well See below for compound dilution and assay scheme v. Dilution of Compounds For IC$_{50}$ determination, test compounds were received as a 1 mM solution in 100% DMSO and distributed into 96-well plates: compounds were then plated into the first column of a new 96-well plate (A1 to G1), 100 μl/well.

An automated station (Biomek FX, Beckman) was used for serial dilutions, producing 1:3 dilutions in 100% DMSO, from line A1 to A10, for all the compounds in the column. Moreover, 4-5 copies of daughter plates are prepared by reformatting 5 μL of this first set of 100% DMSO dilution plates into 384-deep well plates: one copy of these serial dilution plates with the test compounds is thawed on the day of study, reconstituted at the working concentration (3-fold the final concentration) with 162 μL/well of water and used for IC$_{50}$ determination assays. In a standard experiment, the highest concentration (3×) of compounds is typically 30 μM, while the lowest one is typically 1.5 nM. Each 384-well plate generates at least one curve of the standard inhibitor staurosporine and reference wells (total enzyme activity vs. no enzymatic activity) for evaluation of Z' and signal to background (SIB) ratio.

vi. Assay Scheme 384-well plates, V bottom (test plates) are prepared with 5 µl of compound diluted as previously described (3×) and then placed onto a PlateTrak 12 robotized station (Perkin Elmer; the robot has one 384-tip pipetting head for assay start, plus one 96-tip head for dispensing resin) together with one reservoir for Enzyme mix (3×) and one for ATP mix (3×).

Data are analyzed by an internally customized version of the "Assay Explorer" SW package, which provides sigmoidal fitting of the ten-dilution curves for $IC_{50}$ determination in secondary assay/hit confirmation routines.

Method for PIM2 Kinase Inhibition Assay: Dowex Technique i. Kinase Buffer (KB)

The buffer for PIM2 assay was composed of HEPES 50 mM, at pH 7.5, with 1 mM $MgCl_2$, 1 mM DTT, 3 µM $Na_3VO_4$, and 0.2 mg/mL BSA.

Full-length human PIM2 was expressed and purified as described in Fedorov O, et al., PNAS 2007 104, 51, 20523-28.

ii. Assay Conditions (Final Concentrations)

Enzyme concentration=1.5 nM

Aktide substrate (Chemical Abstract Service Registry Number 324029-01-8)=5 µM

ATP=4 µM $^{33}P\text{-}\gamma\text{-}ATP$=1 nM iii. Robotized Dowex Assay

See above: same procedure as described for PIM1.

In vitro Cell Proliferation Assay

MV-4-11 (biphenotypic B myelomonocytic leukemia) cells (1250 cells/well) were seeded in white 384 well-plates in complete medium (RPMI 1640 or EMEM plus 10% Fetal bovine serum) and treated with compounds dissolved in 0.1% DMSO, 24 h after seeding. The cells were incubated at 37° C. and 5% $CO_2$ and after 72 hours the plates were processed using CellTiter-Glo assay (Promega) following the manufacturer's instruction.

CellTiter-Glo is a homogenous method based on the quantification of the ATP present, an indicator of metabolically active cells. ATP is quantified using a system based on luciferase and D-luciferin resulting into light generation. The luminescent signal is proportional to the number of cells present in culture.

Briefly 25 µl/well reagent solution were added to each wells and after 5 minutes shacking microplates were red by Envision (PerkinElmer) luminometer. The luminescent signal was proportional to the number of cells present in culture.

Inhibitory activity was evaluated comparing treated versus control data using Assay Explorer (MDL) program. $IC_{50}$ was calculated using sigmoidal interpolation curve.

Given the above inhibition assays, the compounds of the formula (I) of the invention resulted to possess a good PIM-1 inhibitory activity, typically with an $IC_{50}$ well below 0.05 microM and a good PIM-2 inhibitory activity, typically with an $IC_{50}$ well below 0.2 microM.

Moreover, the compounds of the formula (I) of the invention show good cellular proliferation inhibitory activity, typically with an $IC_{50}$ in the range of from 1 to 7 microM in MV-4-11 cells.

The following Table A reports the experimental data of some representative compounds of the invention of formula (I) being tested in the specific in vitro kinase assay above described on the PIM-1 and PIM-2 enzyme in comparison with some Ref. compounds of the prior art.

Following Table A also reports the antiproliferative activity of some representative compounds of the invention of formula (I) being tested against MV-4-11 cells in comparison with some Ref. compounds of the prior art.

The Ref. compounds are disclosed in the patent application WO2010/031816 cited above.

TABLE A

| Compound | PIM-1 $IC_{50}$ µM | PIM-2 $IC_{50}$ µM | MV4-11 $IC_{50}$ µM |
|---|---|---|---|
| Ref. comp 1 (A157-M-B65 isomer S) | 0.01 | 0.10 | >10 |
| Ref. comp 2 (A127-M-B65 isomer S) | 0.01 | 0.18 | >10 |
| Ref. comp 3 (A127-M-B61 isomer S) | 0.02 | 0.25 | >10 |
| 2 | 0.001 | 0.037 | 1.53 |
| 6 | 0.008 | 0.171 | 3.15 |
| 10 | 0.006 | 0.057 | 6.75 |
| 23 | 0.001 | 0.036 | 1.13 |
| 26 | 0.002 | 0.132 | 1.16 |

So far, the novel compounds of the invention are unexpectedly endowed with a potent PIM-1 and PIM-2 inhibitory activity resulting in an antiproliferative activity significantly higher than that of the structurally closest prior art compounds. Therefore, the compounds of the invention are particularly advantageous, in therapy, against cancer.

The invention claimed is:

1. A compound of formula (I):

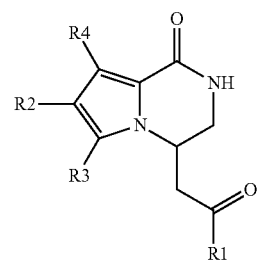

(I)

wherein

R1 is NR5R6 wherein R5 and R6 are each independently hydrogen, an optionally substituted group selected from straight or branched $C_1$-$C_6$ alkyl, $C_2$-$C_6$ alkenyl, $C_2$-$C_6$ alkynyl, $C_3$-$C_7$ cycloalkyl, cycloalkyl-alkyl, aryl, arylalkyl, heterocyclyl and heterocyclylalkyl; or R5 and R6 together with the nitrogen atom to which they are bound, form a 5 to 7 membered heterocyclyl group optionally containing one additional heteroatom selected from N, O and S;

R2 is aryl, arylalkyl, heterocyclyl or heterocyclylalkyl;

R3 and R4 are each independently hydrogen, halogen, cyano, or an optionally substituted group selected from straight or branched $C_1$-$C_6$ alkyl, $C_2$-$C_6$ alkenyl, $C_2$-$C_6$ alkynyl, $C_3$-$C_7$ cycloalkyl, cycloalkyl-alkyl, aryl, arylalkyl, heterocyclyl and heterocyclylalkyl;

and a pharmaceutically acceptable salt thereof, provided that when R3 and R4 are hydrogen, R5 is a group of formula

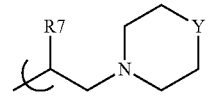

wherein R7 is an optionally substituted group selected from $C_3$-$C_7$ cycloalkyl, and cycloalkyl-alkyl; and Y is N—R' or CH—NR'R", wherein R' and R" are each independently, hydrogen or an optionally substituted group selected from straight or branched $C_1$-$C_6$ alkyl, $C_3$-$C_7$ cycloalkyl, cycloalkylalkyl, heterocyclyl and heterocyclylalkyl, wherein any of the above R1, R2, R3, R4, R5, R6, R7, R' and R" group may be optionally substituted, in any of their free positions, by one or more groups independently selected from: halogen atom, nitro, oxo, cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate.

2. A compound of formula (I) as defined in claim 1 wherein:
R1 is NR5R6 wherein R5 and R6 are each independently hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl, or, together with the nitrogen atom to which they are bound, R5 and R6 may form a 5 to 7 membered heterocyclyl group optionally containing one additional heteroatom selected from N, O and S.

3. A compound of formula (I) as defined in claim 1 wherein:
R3 and R4 are each independently hydrogen, halogen, cyano, or an optionally substituted group selected from straight or branched $C_1$-$C_6$ alkyl, $C_2$-$C_6$ alkynyl, $C_3$-$C_7$ cycloalkyl, arylalkyl, heterocyclyl and heterocyclylalkyl.

4. A compound of formula (I) or a pharmaceutically acceptable salt thereof as defined in claim 1 which is selected from the group consisting of:
2-[(4R)-7-(3-chlorophenyl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide,
2-[(4S)-7-(3-chlorophenyl)-1-oxo-1,2,3,4-tetrahydropyrrolo[1,2-a]pyrazin-4-yl]-N-[1S)-1-cyclohexyl-2-(4-methylpiperazin-1-yl)ethyl]acetamide,
N-[(1S)-1-cyclohexyl-2-(4-methylpiperazin-1-yl)ethyl]-2-[(4R)-7-(3-fluorophenyl)-1-oxo-1,2,3,4-tetrahydropyrrolo[1,2-a]pyrazin-4-yl]acetamide,
N-[(1S)-1-cyclohexyl-2-(4-methylpiperazin-1-yl)ethyl]-2-[(4S)-7-(3-fluorophenyl)-1-oxo-1,2,3,4-tetrahydropyrrolo[1,2-a]pyrazin-4-yl]acetamide,
N-{(1S)-1-cyclohexyl-2-[4-(dimethylamino)piperidin-1-yl]ethyl}-2-[(4R)-7-(3,4-difluorophenyl)-1-oxo-1,2,3,4-tetrahydropyrrolo[1,2-a]pyrazin-4-yl]acetamide,
N-{(1S)-1-cyclohexyl-2-[4-(dimethylamino)piperidin-1-yl]ethyl}-2-[(4S)-7-(3,4-difluorophenyl)-1-oxo-1,2,3,4-tetrahydropyrrolo[1,2-a]pyrazin-4-yl]acetamide,
N-[(1S)-1-cyclohexyl-2-(4-methylpiperazin-1-yl)ethyl]-2-[(4R)-7-(3,4-difluorophenyl)-1-oxo-1,2,3,4-tetrahydropyrrolo[1,2-a]pyrazin-4-yl]acetamide,
N-[(1S)-1-cyclohexyl-2-(4-methylpiperazin-1-yl)ethyl]-2-[(4S)-7-(3,4-difluorophenyl)-1-oxo-1,2,3,4-tetrahydropyrrolo[1,2-a]pyrazin-4-yl]acetamide,
N-{(1S)-1-cyclohexyl-2-[4-(dimethylamino)piperidin-1-yl]ethyl)}-2-[(4R)-7-(2-fluoropyridin-4-yl)-1-oxo-1,2,3,4-tetrahydropyrrolo[1,2-a]pyrazin-4-yl]acetamide,
N-{(1S)-1-cyclohexyl-2-[4-(dimethylamino)piperidin-1-yl]ethyl}-2-[(4S)-7-(2-fluoropyridin-4-yl)-1-oxo-1,2,3,4-tetrahydropyrrolo[1,2-a]pyrazin-4-yl]acetamide,
N-[(1S)-1-cyclohexyl-2-(4-methylpiperazin-1-yl)ethyl]-2-4R)-7-(2-fluoropyridin-4-yl)-1-oxo-1,2,3,4-tetrahydropyrrolo[1,2-a]pyrazin-4-yl]acetamide,
N-[(1S)-1-cyclohexyl-2-(4-methylpiperazin-1-yl)ethyl]-2-[(4S)-7-(2-fluoropyridin-4-yl)-1-oxo-1,2,3,4-tetrahydropyrrolo[1,2-a]pyrazin-4-yl]acetamide,
N-[(1S)-1-cyclohexyl-2-(4-methylpiperazin-1-yl)ethyl]-2-[(4R)-7-(3-hydroxyphenyl)-1-oxo-1,2,3,4-tetrahydropyrrolo[1,2-a]pyrazin-4-yl]acetamide,
N-{(1S)-1-cyclohexyl-2-[4-(dimethylamino)piperidin-1-yl]ethyl}-2-[7-(3-hydroxyphenyl)-1-oxo-1,2,3,4-tetrahydropyrrolo[1,2-a]pyrazin-4-yl]acetamide,
N-{(1S)-1-cyclohexyl-2-[4-(dimethylamino)piperidin-1-yl]ethyl}-2-{(4R)-1-oxo-7-[3-(trifluoromethyl)phenyl]-1,2,3,4-tetrahydropyrrolo[1,2-a]pyrazin-4-yl}acetamide,
N-{(1S)-1-cyclohexyl-2-[4-(dimethylamino)piperidin-1-yl]ethyl}-2-{(4S)-1-oxo-7-[3-(trifluoromethyl)phenyl]-1,2,3,4-tetrahydropyrrolo[1,2-a]pyrazin-4-yl}acetamide,
N-[(1S)-1-cyclohexyl-2-(4-methylpiperazin-1-yl)ethyl]-2-{(4R)-1-oxo-7-[3-(trifluoromethyl)phenyl]-1,2,3,4-tetrahydropyrrolo[1,2-a]pyrazin-4-yl}acetamide,
N-[(1S)-1-cyclohexyl-2-(4-methylpiperazin-1-yl)ethyl]-2-{(4S)-1-oxo-7-[3-(trifluoromethyl)phenyl]-1,2,3,4-tetrahydropyrrolo[1,2-a]pyrazin-4-yl}acetamide,
N-[(1S)-1-cyclohexyl-2-(4-methylpiperazin-1-yl)ethyl]-2-[(4S)-1-oxo-7-(1H-pyrazol-4-yl1)-1,2,3,4-tetrahydropyrrolo[1,2-a]pyrazin-4-yl]acetamide,
2-[(4R)-7-(3-chlorophenyl)-1-oxo-1,2,3,4-tetrahydropyrrolo[1,2-a]pyrazin-4-yl]-N-{(1S)-1-cyclohexyl-2-[4-(dimethylamino)piperidin-1-yl]ethyl}acetamide,
2-[(4S)-7-(3-chlorophenyl)-1-oxo-1,2,3,4-tetrahydropyrrolo[1,2-a]pyrazin-4-yl]-N-{(1S)-1-cyclohexyl-2-[4-(dimethylamino)piperidin-1-yl]ethyl}acetamide,
2-[(4S)-7-(5-chloro-2-fluorophenyl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide,
2-[(4R)-7-(5-chloro-2-fluorophenyl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide,
2-[(4R)-7-(3-chloro-4-hydroxyphenyl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide,
2-[(4S)-7-(3-chloro-4-hydroxyphenyl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide,
2-[(4S)-6-bromo-7-(3-chloro-4-hydroxyphenyl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide, 2-[(4R)-7-(2-aminopyrimidin-4-yl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide, 2-[(4S)-7-(2-aminopyrimidin-4-yl)-1-oxo-1,2,3,4-tetrahydropyrrolo[1,2-a]pyrazin-4-yl]-N-[(1S)-1-cyclohexyl-2-(4-methylpiperazin-1-yl)ethyl]acetamide, and 2-[(4S)-7-(3-fluorophenyl)-1-oxo-1,2,3,4-tetrahydropyrrolo[1,2-a]pyrazin-4-yl]-N-[(2R)-1-hydroxypropan-2-l]acetamide, 2-[6-bromo-7-(3-fluorophenyl)-1-oxo-1,2,3,4-tetrahydropyrrolo[1,2-a]pyrazin-4-yl]acetamide, and 2-[(4S)-7-(3-chlorophenyl)-1-oxo-6-phenyl-1,2,3,4-tetrahydropyrrolo[1,2-a]pyrazin-4-yl]-N-[(3R)-piperidin-3-yl]acetamide.

5. A pharmaceutical composition comprising a therapeutically effective amount of a compound of formula (I) or a pharmaceutically acceptable salt thereof, as defined in claim 1, and at least one pharmaceutically acceptable excipient, carrier and/or diluent.

6. The pharmaceutical composition according to claim 5 further comprising one or more chemotherapeutic agents.

7. A product or kit comprising a compound of formula (I) or a pharmaceutically acceptable salt thereof, as defined in claim 1, or a pharmaceutical composition comprising a therapeutically effective amount of said compound of formula (I) or a pharmaceutically acceptable salt thereof and at least one pharmaceutically acceptable excipient, carrier and/or diluent and one or more chemotherapeutic agents.

8. A method for treating a disease caused by and/or associated with a dysregulated protein kinase activity, the disease selected from the group consisting of breast carcinoma, colon carcinoma, lung carcinoma, small cell lung cancer, ovary carcinoma, pancreas carcinoma, thyroid carcinoma, prostate carcinoma, leukaemia, myeloma, rhabdomyosarcoma, neuroblastoma, glioma and melanoma, which comprises administering to a mammal in need thereof an effective amount of a compound of formula (I) as defined in claim 1.

9. The method according to claim 8 further comprising subjecting the mammal in need thereof to a radiation therapy or chemotherapy regimen in combination with at least one cytostatic or cytotoxic agent.

10. The method according to claim 8 wherein the mammal in need thereof is a human.

11. An in vitro method for inhibiting PIM-1, PIM-2 and PIM-3 protein kinase activity which comprises contacting said protein kinase with an effective amount of a compound of formula (I) as defined in claim 1.

12. A process for preparing a compound of formula (I) as defined in claim 1 or a pharmaceutically acceptable salt thereof, characterized in that the process comprises the following step:

reacting a compound of formula (VII)

R5R6NH (VII)

wherein R5 and R6 are hydrogen, an optionally substituted group selected from straight or branched $C_1$-$C_6$ alkyl, $C_2$-$C_6$ alkenyl, $C_2$-$C_6$ alkynyl, $C_3$-$C_7$ cycloalkyl, cycloalkyl-alkyl, aryl, arylalkyl, heterocyclyl and heterocyclylalkyl; or R5 and R6 together with the nitrogen atom to which they are bound, form a 5 to 7 membered heterocyclyl group optionally containing one additional heteroatom selected from N, O and S, alternatively with a compound of formula (IV)

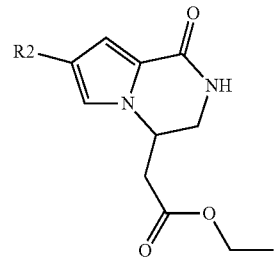

(IV)

wherein R2 is aryl, arylalkyl, heterocyclyl or heterocyclylalkyl;

or a compound of formula (XIV)

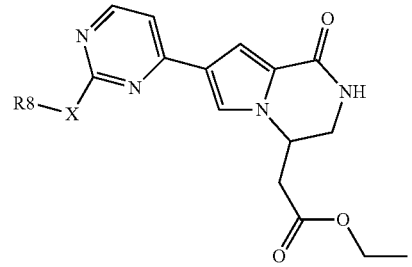

(XIV)

wherein X is a single bond or a divalent radical selected from —NR', —O— and —S, wherein R' is hydrogen or an optionally substituted group selected from straight or branched $C_1$-$C_6$ alkyl, $C_3$-$C_7$ cycloalkyl, cycloalkylalkyl, heterocyclyl and heterocyclylalkyl; and R8 is hydrogen or an optionally substituted group selected from amino, straight or branched $C_1$-$C_6$ alkyl, $C_3$-$C_7$ cycloalkyl, cycloalkyl-alkyl, aryl, arylalkyl, heterocyclyl and heterocyclylalkyl; or a compound of formula (XV)

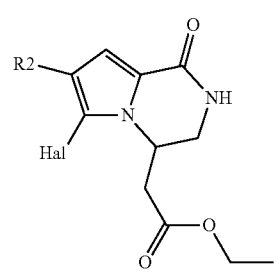

(XV)

wherein R2 is aryl, arylalkyl, heterocyclyl or heterocyclylalkyl and Hal is halogen; or a compound of formula (XVII)

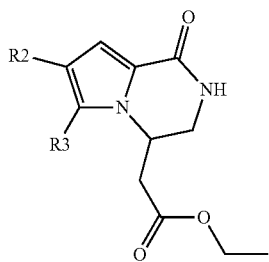

(XVII)

wherein R2 is aryl, arylalkyl, heterocyclyl or heterocyclylalkyl and R3 is an optionally substituted group selected from straight or branched $C_1$-$C_6$ alkyl, $C_2$-$C_6$ alkenyl, $C_2$-$C_6$ alkynyl, $C_3$-$C_7$ cycloalkyl, cycloalkyl-alkyl, aryl, arylalkyl, heterocyclyl and heterocyclylalkyl;
to give a compound of the formula (I)

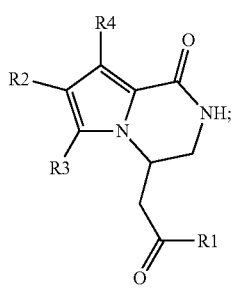

(I)

and (i) optionally converting a compound of the formula (I) into a different compound of the formula (I), (ii) optionally converting a compound of the formula (I) into a pharmaceutically acceptable salt thereof, or (iii) converting a pharmaceutically acceptable salt of the compound of formula (I) to the compound of the formula (I).

13. A process according to claim 12, characterized in that conversion of a compound of formula (I) into a different compound of formula (I) is carried out with one of the following methods:

Conv. a) converting a compound of the formula (I) wherein R3 or R4 is hydrogen into the corresponding compound of the formula (I) wherein R3 or R4 is a halogen

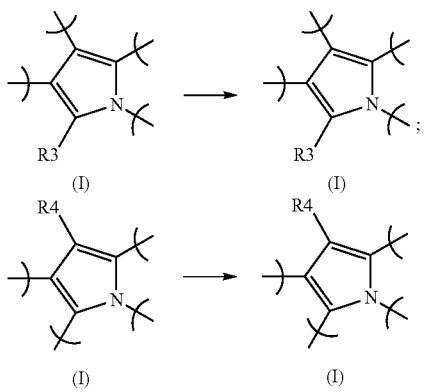

through reaction with an halogenating agent selected from the group consisting of N-chlorosuccinimide, N-bromosuccinimide and N-iodosuccinimide;

Conv. b) converting a compound of formula (I) wherein R3 or R4 is halogen into the corresponding compound of formula (I) wherein R3 or R4 is an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl

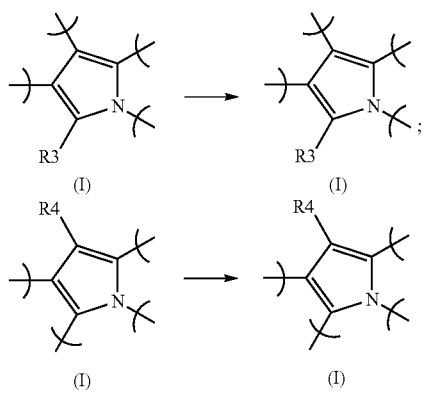

by reaction with a compound of formula (XVIII) or formula (XX) respectively:

R3″-G        (XVIII)

R4′-G        (XX)

wherein R3″ or R4′ is a group selected from straight or branched $C_1$-$C_6$ alkyl, $C_3$-$C_7$ cycloalkyl, cycloalkyl-alkyl, aryl, arylalkyl, heterocyclyl and heterocyclylalkyl, and G is selected from the group consisting of —B(OH)$_2$, —B(OAlk)$_2$, —Sn(Alk)$_4$, ZnCl$_2$ or MgCl$_2$;

Conv. c) converting a compound of formula (I) wherein R3 or R4 is halogen into the corresponding compound of formula (I) wherein R3 or R4 is an alkyne

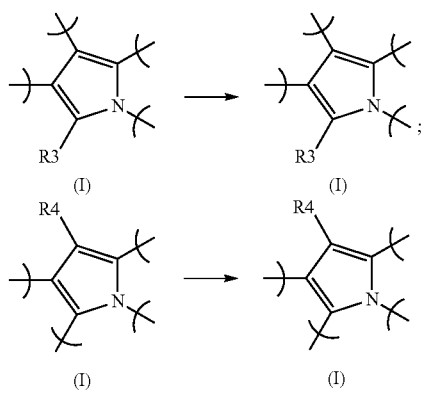

by reaction with a terminal alkyne of formula (XIX):

R$^a$C≡CH        (XIX)

wherein R$^a$ is hydrogen, or a group selected from straight or branched $C_1$-$C_6$ alkyl, $C_2$-$C_6$ alkenyl, $C_2$-$C_6$ alkynyl, $C_3$-$C_7$ cycloalkyl, cycloalkyl-alkyl, aryl, arylalkyl, heterocyclyl and heterocyclylalkyl;

Conv. d) converting a compound of formula (I) wherein R3 or R4 is halogen into the corresponding compound of formula (I) wherein R3 or R4 is cyano
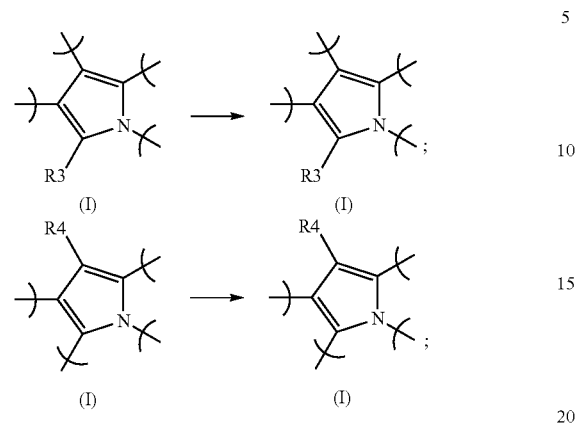
and
Conv. e) removing any protecting group or groups.
* * * * *